United States Patent
Yeung et al.

(10) Patent No.: US 8,777,992 B2
(45) Date of Patent: *Jul. 15, 2014

(54) METHODS FOR ANCHORING SUTURE AND APPROXIMATING TISSUE

(71) Applicant: Neotract, Inc., Pleasanton, CA (US)

(72) Inventors: Jeffrey E. Yeung, San Jose, CA (US); Teresa Yeung, San Jose, CA (US)

(73) Assignee: NeoTract, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/838,500

(22) Filed: Mar. 15, 2013

(65) Prior Publication Data

US 2013/0261665 A1    Oct. 3, 2013

Related U.S. Application Data

(60) Continuation of application No. 12/803,110, filed on Jun. 19, 2010, now Pat. No. 8,454,655, which is a division of application No. 10/914,059, filed on Aug. 5, 2004, now Pat. No. 7,766,939, which is a continuation of application No. PCT/US02/41399, filed on Dec. 24, 2002.

(60) Provisional application No. 60/364,947, filed on Mar. 14, 2002.

(51) Int. Cl.
*A61B 17/04* (2006.01)

(52) U.S. Cl.
USPC .............................................. 606/232

(58) Field of Classification Search
USPC .............................................. 606/232
See application file for complete search history.

(56) References Cited

U.S. PATENT DOCUMENTS

| | | | |
|---|---|---|---|
| 659,422 | A | 10/1900 | Shidler |
| 780,392 | A | 1/1905 | Wanamaker et al. |
| 789,467 | A | 5/1905 | West |
| 2,579,192 | A | 12/1951 | Kohl |
| 2,646,298 | A | 7/1953 | Leary |
| 2,697,624 | A | 12/1954 | Thomas |

(Continued)

FOREIGN PATENT DOCUMENTS

| | | |
|---|---|---|
| DE | 10159470 | 6/2003 |
| EP | 0246836 | 12/1991 |

(Continued)

OTHER PUBLICATIONS

Sharp, Howard T., M.D., et al., "Instruments and Methods—The 4-S Modification of the Roeder Knot: How to Tie It", Obstetrics & Gynecology, p. 1004-1006, vol. 90, No. 6, Dec. 1997.

(Continued)

*Primary Examiner* — Gregory Anderson
(74) *Attorney, Agent, or Firm* — Steptoe & Johnson LLP

(57) ABSTRACT

An elastically curved suture anchor is resiliently straightened and delivered into tissue by a needle. When the needle is withdrawn, resumption of the curvature provides leverage for anchor rotation as the attached suture is pulled to fasten the anchor within the tissue. A fin at the proximal end of the anchor further increases the rotational leverage and expedites anchor fastening. When two or more anchors with connecting suture are delivered in series on a needle, the tension of the suture helps to draw the anchors together and approximates the pierced tissue.

20 Claims, 36 Drawing Sheets

(56) References Cited

U.S. PATENT DOCUMENTS

| | | |
|---|---|---|
| 2,734,299 A | 2/1956 | Masson |
| 2,825,592 A | 3/1958 | Semple |
| 3,326,586 A | 6/1967 | Frost et al. |
| 3,470,834 A | 10/1969 | Bone |
| 3,521,918 A | 7/1970 | Hammond |
| 3,713,680 A | 1/1973 | Pagano |
| 3,716,058 A | 2/1973 | Tanner, Jr. |
| 3,756,638 A | 9/1973 | Stockberger |
| 3,873,140 A | 3/1975 | Bloch |
| 3,875,648 A | 4/1975 | Bone |
| 3,931,667 A | 1/1976 | Merser et al. |
| 3,976,079 A | 8/1976 | Samuels et al. |
| 4,006,747 A | 2/1977 | Kronenthal et al. |
| 4,210,148 A | 7/1980 | Stivala |
| 4,235,238 A | 11/1980 | Ogiu et al. |
| 4,291,698 A | 9/1981 | Fuchs et al. |
| 4,409,974 A | 10/1983 | Freedland |
| 4,493,323 A | 1/1985 | Albright et al. |
| 4,513,746 A | 4/1985 | Aranyi |
| 4,621,640 A | 11/1986 | Mulhollan et al. |
| 4,657,461 A | 4/1987 | Smith |
| 4,669,473 A | 6/1987 | Richards et al. |
| 4,705,040 A | 11/1987 | Mueller et al. |
| 4,714,281 A | 12/1987 | Peck |
| 4,738,255 A | 4/1988 | Goble et al. |
| 4,741,330 A | 5/1988 | Hayhurst |
| 4,744,364 A | 5/1988 | Kensey |
| 4,750,492 A | 6/1988 | Jacobs |
| 4,762,128 A | 8/1988 | Rosenbluth |
| 4,823,794 A | 4/1989 | Pierce |
| 4,899,743 A | 2/1990 | Nicholson et al. |
| 4,926,860 A | 5/1990 | Stice et al. |
| 4,946,468 A | 8/1990 | Li |
| 4,955,913 A | 9/1990 | Robinson |
| 4,968,315 A | 11/1990 | Gatturna et al. |
| 5,002,550 A | 3/1991 | Li |
| 5,041,129 A | 8/1991 | Hayhurst et al. |
| 5,046,513 A | 9/1991 | Gatturna et al. |
| 5,053,046 A | 10/1991 | Janese |
| 5,100,421 A | 3/1992 | Christoudias |
| 5,123,914 A | 6/1992 | Cope |
| 5,129,912 A | 7/1992 | Noda et al. |
| 5,192,303 A | 3/1993 | Gatturna et al. |
| 5,203,787 A | 4/1993 | Noblitt et al. |
| 5,217,470 A | 6/1993 | Weston |
| 5,217,486 A | 6/1993 | Rice et al. |
| 5,234,454 A | 8/1993 | Bangs |
| 5,236,445 A | 8/1993 | Hayhurst et al. |
| 5,258,015 A | 11/1993 | Li et al. |
| 5,269,809 A | 12/1993 | Hayhurst et al. |
| 5,330,488 A | 7/1994 | Goldrath |
| 5,334,200 A | 8/1994 | Johnson |
| 5,336,240 A | 8/1994 | Metzler et al. |
| 5,354,271 A | 10/1994 | Voda |
| 5,358,511 A | 10/1994 | Gatturna et al. |
| 5,364,408 A | 11/1994 | Gordon |
| 5,366,490 A | 11/1994 | Edwards et al. |
| 5,368,599 A | 11/1994 | Hirsch et al. |
| 5,370,646 A | 12/1994 | Reese et al. |
| 5,380,334 A | 1/1995 | Torrie et al. |
| 5,391,182 A | 2/1995 | Chin |
| 5,403,348 A | 4/1995 | Bonutti |
| 5,405,352 A | 4/1995 | Weston |
| 5,411,520 A | 5/1995 | Nash et al. |
| 5,417,691 A | 5/1995 | Hayhurst |
| 5,435,805 A | 7/1995 | Edwards et al. |
| 5,470,337 A | 11/1995 | Moss |
| 5,472,446 A | 12/1995 | De la Torre |
| 5,480,406 A | 1/1996 | Nolan et al. |
| 5,501,690 A | 3/1996 | Measamer et al. |
| 5,507,754 A | 4/1996 | Green et al. |
| 5,522,846 A | 6/1996 | Bonutti |
| 5,531,763 A | 7/1996 | Mastri et al. |
| 5,536,240 A | 7/1996 | Edwards et al. |
| 5,540,704 A | 7/1996 | Gordon et al. |
| 5,545,171 A | 8/1996 | Sharkey et al. |
| 5,545,178 A | 8/1996 | Kensey et al. |
| 5,550,172 A | 8/1996 | Regula et al. |
| 5,554,162 A | 9/1996 | DeLange |
| 5,554,171 A | 9/1996 | Gatturna et al. |
| 5,562,689 A | 10/1996 | Green et al. |
| 5,569,305 A | 10/1996 | Bonutti |
| 5,571,104 A | 11/1996 | Li |
| 5,573,540 A | 11/1996 | Yoon |
| 5,578,044 A | 11/1996 | Gordon et al. |
| 5,591,177 A | 1/1997 | Lehrer |
| 5,593,421 A | 1/1997 | Bauer |
| 5,611,515 A | 3/1997 | Benderev et al. |
| 5,626,614 A | 5/1997 | Hart |
| 5,630,824 A | 5/1997 | Hart |
| 5,647,836 A | 7/1997 | Blake, III et al. |
| 5,665,109 A | 9/1997 | Yoon |
| 5,667,486 A | 9/1997 | Mikulich et al. |
| 5,669,917 A | 9/1997 | Sauer et al. |
| 5,690,649 A | 11/1997 | Li |
| 5,690,677 A | 11/1997 | Schmiedling et al. |
| 5,697,950 A | 12/1997 | Fucci et al. |
| 5,707,394 A | 1/1998 | Miller et al. |
| 5,716,368 A | 2/1998 | De la Torre |
| 5,718,717 A | 2/1998 | Bonutti |
| 5,725,556 A | 3/1998 | Moser et al. |
| 5,725,557 A | 3/1998 | Gatturna et al. |
| 5,733,306 A | 3/1998 | Bonutti |
| 5,741,276 A | 4/1998 | Poloyko et al. |
| 5,746,753 A | 5/1998 | Sullivan et al. |
| 5,749,846 A | 5/1998 | Edwards et al. |
| 5,752,963 A | 5/1998 | Allard et al. |
| 5,782,862 A | 7/1998 | Bonutti |
| 5,782,864 A | 7/1998 | Lizardi |
| 5,800,445 A | 9/1998 | Ratcliff et al. |
| 5,807,403 A | 9/1998 | Beyer et al. |
| 5,810,848 A | 9/1998 | Hayhurst |
| 5,814,072 A | 9/1998 | Bonutti |
| 5,830,221 A | 11/1998 | Stein |
| 5,845,645 A | 12/1998 | Bonutti |
| 5,846,254 A | 12/1998 | Schulze et al. |
| 5,861,002 A | 1/1999 | Desai |
| 5,868,762 A | 2/1999 | Cragg et al. |
| 5,873,891 A | 2/1999 | Sohn |
| 5,897,574 A | 4/1999 | Bonutti |
| 5,899,911 A | 5/1999 | Carter |
| 5,899,921 A | 5/1999 | Caspari et al. |
| 5,904,696 A | 5/1999 | Rosenman |
| 5,908,428 A | 6/1999 | Scirica et al. |
| 5,919,198 A | 7/1999 | Graves, Jr. et al. |
| 5,919,202 A | 7/1999 | Yoon |
| 5,921,986 A | 7/1999 | Bonutti |
| 5,928,252 A | 7/1999 | Steadman et al. |
| 5,931,844 A | 8/1999 | Thompson et al. |
| 5,944,739 A | 8/1999 | Zlock et al. |
| 5,948,001 A | 9/1999 | Larsen |
| 5,948,002 A | 9/1999 | Bonutti |
| 5,954,057 A | 9/1999 | Li |
| 5,954,747 A | 9/1999 | Clark |
| 5,964,732 A | 10/1999 | Wilard |
| 5,971,447 A | 10/1999 | Steck, III |
| 6,010,514 A | 1/2000 | Burney et al. |
| 6,011,525 A | 1/2000 | Piole |
| 6,030,393 A | 2/2000 | Corlew |
| 6,033,430 A | 3/2000 | Bonutti |
| 6,036,701 A | 3/2000 | Rosenman |
| 6,048,351 A | 4/2000 | Gordon et al. |
| 6,053,908 A | 4/2000 | Crainich et al. |
| 6,056,722 A | 5/2000 | Jayaraman |
| 6,056,772 A | 5/2000 | Bonutti |
| 6,068,648 A | 5/2000 | Cole et al. |
| 6,080,167 A | 6/2000 | Lyell |
| 6,086,608 A | 7/2000 | Ek et al. |
| 6,110,183 A | 8/2000 | Cope |
| 6,117,160 A | 9/2000 | Bonutti |
| 6,117,161 A | 9/2000 | Li et al. |
| 6,120,539 A | 9/2000 | Eldridge et al. |
| 6,139,555 A | 10/2000 | Hart et al. |
| RE36,974 E | 11/2000 | Bonutti |

(56) References Cited

U.S. PATENT DOCUMENTS

| | | | |
|---|---|---|---|
| 6,143,006 A | 11/2000 | Chan | |
| 6,159,234 A | 12/2000 | Bonutti et al. | |
| 6,200,329 B1 | 3/2001 | Fung et al. | |
| 6,206,895 B1 | 3/2001 | Levinson | |
| 6,228,096 B1 | 5/2001 | Marchand | |
| 6,258,124 B1 | 7/2001 | Darois et al. | |
| 6,261,302 B1 | 7/2001 | Voegele et al. | |
| 6,270,530 B1 | 8/2001 | Eldridge et al. | |
| 6,280,460 B1 | 8/2001 | Bolduc et al. | |
| 6,290,711 B1 | 9/2001 | Caspari et al. | |
| 6,306,158 B1 * | 10/2001 | Bartlett | 606/232 |
| 6,312,448 B1 | 11/2001 | Bonutti | |
| 6,319,263 B1 | 11/2001 | Levinson | |
| 6,322,112 B1 | 11/2001 | Duncan | |
| 6,332,889 B1 | 12/2001 | Sancoff et al. | |
| 6,398,795 B1 | 6/2002 | McAllister et al. | |
| 6,425,900 B1 | 7/2002 | Knodel et al. | |
| 6,428,562 B2 | 8/2002 | Bonutti | |
| 6,436,107 B1 | 8/2002 | Wang et al. | |
| 6,461,355 B2 | 10/2002 | Svejkovsky et al. | |
| 6,482,235 B1 | 11/2002 | Lambrecht et al. | |
| 6,488,691 B1 | 12/2002 | Carroll et al. | |
| 6,491,707 B2 | 12/2002 | Makower et al. | |
| 6,494,888 B1 | 12/2002 | Laufer et al. | |
| 6,500,195 B2 | 12/2002 | Bonutti | |
| 6,506,190 B1 | 1/2003 | Walshe | |
| 6,506,196 B1 | 1/2003 | Laufer | |
| 6,517,569 B2 | 2/2003 | Mikus et al. | |
| 6,527,702 B2 | 3/2003 | Whalen et al. | |
| 6,527,794 B1 | 3/2003 | McDevitt et al. | |
| 6,530,932 B1 | 3/2003 | Swayze et al. | |
| 6,533,796 B1 | 3/2003 | Sauer et al. | |
| 6,547,725 B1 | 4/2003 | Paolitto et al. | |
| 6,551,328 B2 | 4/2003 | Kortenbach | |
| 6,551,333 B2 | 4/2003 | Kuhns et al. | |
| 6,565,578 B1 | 5/2003 | Peifer et al. | |
| 6,569,187 B1 | 5/2003 | Bonutti et al. | |
| 6,572,626 B1 | 6/2003 | Knodel et al. | |
| 6,572,635 B1 | 6/2003 | Bonutti | |
| 6,572,653 B1 | 6/2003 | Simonson | |
| 6,592,609 B1 | 7/2003 | Bonutti | |
| 6,596,013 B2 | 7/2003 | Yang et al. | |
| 6,626,913 B1 | 9/2003 | McKinnon et al. | |
| 6,626,916 B1 | 9/2003 | Yeung et al. | |
| 6,626,919 B1 | 9/2003 | Swanstrom | |
| 6,629,534 B1 | 10/2003 | St. Goar et al. | |
| 6,641,592 B1 | 11/2003 | Sauer et al. | |
| 6,656,182 B1 | 12/2003 | Hayhurst | |
| 6,660,023 B2 | 12/2003 | McDevitt et al. | |
| 6,663,589 B1 | 12/2003 | Halevy | |
| 6,663,639 B1 | 12/2003 | Laufer et al. | |
| 6,699,263 B2 | 3/2004 | Cope | |
| 6,706,047 B2 | 3/2004 | Trout et al. | |
| 6,709,493 B2 | 3/2004 | DeGuiseppi et al. | |
| 6,715,804 B2 | 4/2004 | Beers | |
| 6,719,709 B2 | 4/2004 | Whalen et al. | |
| 6,730,112 B2 | 5/2004 | Levinson | |
| 6,736,823 B2 | 5/2004 | Darois et al. | |
| 6,736,854 B2 | 5/2004 | Vadurro et al. | |
| 6,740,098 B2 | 5/2004 | Abrams et al. | |
| 6,767,037 B2 | 7/2004 | Wenstrom, Jr. | |
| 6,770,076 B2 | 8/2004 | Foerster | |
| 6,773,438 B1 | 8/2004 | Knodel et al. | |
| 6,773,441 B1 | 8/2004 | Laufer et al. | |
| 6,790,213 B2 | 9/2004 | Cherok et al. | |
| 6,802,846 B2 | 10/2004 | Hauschild et al. | |
| 6,821,282 B2 | 11/2004 | Perry et al. | |
| 6,821,285 B2 | 11/2004 | Laufer et al. | |
| 6,821,291 B2 | 11/2004 | Boleg et al. | |
| 6,835,200 B2 | 12/2004 | Laufer et al. | |
| 6,905,475 B2 | 6/2005 | Hauschild et al. | |
| 6,908,473 B2 | 6/2005 | Skiba et al. | |
| 6,926,732 B2 | 8/2005 | Derus et al. | |
| 6,951,565 B2 | 10/2005 | Keane et al. | |
| 6,986,775 B2 | 1/2006 | Morales et al. | |
| 6,991,596 B2 | 1/2006 | Whalen et al. | |
| 6,991,647 B2 | 1/2006 | Jadhav | |
| 6,997,940 B2 | 2/2006 | Bonutti | |
| 7,001,327 B2 | 2/2006 | Whalen et al. | |
| 7,011,688 B2 | 3/2006 | Gryska et al. | |
| 7,015,253 B2 | 3/2006 | Escandon et al. | |
| 7,048,698 B2 | 5/2006 | Whalen et al. | |
| 7,048,747 B2 | 5/2006 | Arcia et al. | |
| 7,060,077 B2 | 6/2006 | Gordon et al. | |
| 7,081,126 B2 | 7/2006 | McDevitt et al. | |
| 7,083,638 B2 | 8/2006 | Foerster | |
| 7,087,073 B2 | 8/2006 | Bonutti | |
| 7,089,064 B2 | 8/2006 | Manker et al. | |
| 7,090,690 B2 | 8/2006 | Foerster et al. | |
| 7,093,601 B2 | 8/2006 | Manker et al. | |
| 7,105,004 B2 | 9/2006 | Dicesare et al. | |
| 7,108,655 B2 | 9/2006 | Whalen et al. | |
| 7,141,038 B2 | 11/2006 | Whalen et al. | |
| 7,153,314 B2 | 12/2006 | Laufer et al. | |
| 7,179,225 B2 | 2/2007 | Shluzas | |
| 7,226,558 B2 | 6/2007 | Nieman et al. | |
| 7,232,448 B2 | 6/2007 | Battles et al. | |
| 7,288,063 B2 | 10/2007 | Petros et al. | |
| 7,303,108 B2 | 12/2007 | Shelton, IV | |
| 7,320,701 B2 | 1/2008 | Haut et al. | |
| 7,322,974 B2 | 1/2008 | Swoyer et al. | |
| 7,334,822 B1 | 2/2008 | Hines et al. | |
| 7,340,300 B2 | 3/2008 | Christopherson et al. | |
| 7,399,304 B2 | 7/2008 | Gambale et al. | |
| 7,402,166 B2 | 7/2008 | Feigl | |
| 7,416,554 B2 | 8/2008 | Lam et al. | |
| 7,553,317 B2 | 6/2009 | Wesenburgh, II et al. | |
| 7,608,108 B2 | 10/2009 | Bhatnager et al. | |
| 7,658,311 B2 | 2/2010 | Boudreaux | |
| 7,674,275 B2 | 3/2010 | Martin et al. | |
| 7,727,248 B2 | 6/2010 | Smith et al. | |
| 7,887,551 B2 * | 2/2011 | Bojarski et al. | 606/139 |
| 2001/0044639 A1 | 11/2001 | Levinson | |
| 2002/0095154 A1 | 7/2002 | Atkinson et al. | |
| 2002/0128684 A1 | 9/2002 | Foerster | |
| 2002/0161382 A1 | 10/2002 | Neisz et al. | |
| 2002/0193809 A1 | 12/2002 | Meade | |
| 2003/0109769 A1 | 6/2003 | Lowery et al. | |
| 2003/0191497 A1 | 10/2003 | Cope | |
| 2003/0204195 A1 | 10/2003 | Keane et al. | |
| 2004/0030217 A1 | 2/2004 | Yeung et al. | |
| 2004/0043052 A1 | 3/2004 | Hunter et al. | |
| 2004/0078046 A1 | 4/2004 | Barzell et al. | |
| 2004/0193191 A1 | 9/2004 | Starksen et al. | |
| 2004/0193194 A1 | 9/2004 | Laufer et al. | |
| 2004/0194790 A1 | 10/2004 | Laufer et al. | |
| 2004/0243178 A1 | 12/2004 | Haut et al. | |
| 2004/0243179 A1 | 12/2004 | Foerster | |
| 2004/0243180 A1 | 12/2004 | Donnelly | |
| 2004/0243227 A1 | 12/2004 | Starksen et al. | |
| 2004/0260345 A1 | 12/2004 | Foerster | |
| 2005/0055087 A1 | 3/2005 | Starksen | |
| 2005/0065550 A1 | 3/2005 | Starksen et al. | |
| 2005/0107811 A1 | 5/2005 | Starksen et al. | |
| 2005/0107812 A1 | 5/2005 | Starksen et al. | |
| 2005/0154401 A1 | 7/2005 | Weldon et al. | |
| 2005/0177181 A1 | 8/2005 | Kagen et al. | |
| 2005/0203344 A1 | 9/2005 | Orban, III et al. | |
| 2005/0203550 A1 | 9/2005 | Laufer et al. | |
| 2005/0216078 A1 | 9/2005 | Starksen et al. | |
| 2005/0267405 A1 | 12/2005 | Shah | |
| 2005/0273138 A1 | 12/2005 | Starksen et al. | |
| 2006/0025750 A1 | 2/2006 | Starksen et al. | |
| 2006/0025784 A1 | 2/2006 | Starksen et al. | |
| 2006/0025789 A1 | 2/2006 | Laufer et al. | |
| 2006/0025819 A1 | 2/2006 | Nobis et al. | |
| 2006/0030884 A1 | 2/2006 | Yeung et al. | |
| 2006/0058817 A1 | 3/2006 | Starksen et al. | |
| 2006/0089646 A1 | 4/2006 | Bonutti | |
| 2006/0167477 A1 | 7/2006 | Arcia et al. | |
| 2006/0265042 A1 | 11/2006 | Catanese, III et al. | |
| 2006/0282081 A1 | 12/2006 | Fanton et al. | |
| 2007/0049929 A1 | 3/2007 | Catanese, III | |
| 2007/0049970 A1 | 3/2007 | Belef et al. | |

(56) References Cited

U.S. PATENT DOCUMENTS

| | | |
|---|---|---|
| 2007/0060931 A1 | 3/2007 | Hamilton et al. |
| 2007/0088362 A1 | 4/2007 | Bonutti |
| 2007/0112385 A1 | 5/2007 | Conlon |
| 2007/0142846 A1 | 6/2007 | Catanese, III et al. |
| 2007/0173888 A1 | 7/2007 | Gertner et al. |
| 2007/0260259 A1 | 11/2007 | Fanton et al. |
| 2008/0009888 A1 | 1/2008 | Ewers et al. |
| 2008/0021445 A1 | 1/2008 | Elmouelhi et al. |
| 2008/0033488 A1 | 2/2008 | Catanese, III et al. |
| 2008/0039894 A1 | 2/2008 | Catanese, III et al. |
| 2008/0045978 A1 | 2/2008 | Kuhns et al. |
| 2008/0058710 A1 | 3/2008 | Wilk |
| 2008/0065120 A1 | 3/2008 | Zannis et al. |
| 2008/0082113 A1 | 4/2008 | Bishop et al. |
| 2008/0086172 A1 | 4/2008 | Martin et al. |
| 2008/0091220 A1 | 4/2008 | Chu |
| 2008/0091237 A1 | 4/2008 | Schwartz et al. |
| 2008/0119874 A1 | 5/2008 | Merves |
| 2008/0154378 A1 | 6/2008 | Pelo |
| 2008/0195145 A1 | 8/2008 | Bonutti et al. |
| 2008/0208220 A1 | 8/2008 | Shiono et al. |
| 2010/0010631 A1 | 1/2010 | Otte et al. |
| 2010/0114162 A1 | 5/2010 | Bojarski et al. |
| 2010/0286106 A1 | 11/2010 | Gat et al. |
| 2010/0286679 A1 | 11/2010 | Hoey et al. |

FOREIGN PATENT DOCUMENTS

| | | |
|---|---|---|
| EP | 0464480 | 1/1992 |
| EP | 0632999 | 1/1995 |
| EP | 1016377 | 7/2000 |
| EP | 1082941 | 3/2005 |
| EP | 1006909 | 1/2007 |
| EP | 1852071 | 11/2007 |
| EP | 1670361 | 4/2008 |
| EP | 1884198 | 6/2008 |
| EP | 1884199 | 6/2008 |
| EP | 1331886 | 12/2008 |
| FR | 2750031 | 6/1996 |
| JP | 58036559 | 3/1983 |
| JP | 9122134 | 5/1997 |
| JP | 2004344427 | 12/2004 |
| RU | 2062121 | 6/1996 |
| RU | 2112571 | 6/1998 |
| RU | 2128012 | 3/1999 |
| RU | 2221501 | 1/2004 |
| SU | 0825094 | 4/1981 |
| WO | WO9210142 | 6/1992 |
| WO | WO9304727 | 3/1993 |
| WO | WO9315664 | 8/1993 |
| WO | WO0230335 | 4/2002 |
| WO | WO03039334 | 5/2003 |
| WO | WO03077772 | 9/2003 |
| WO | WO2004019787 | 3/2004 |
| WO | WO2004017845 | 4/2004 |
| WO | WO2004030569 | 4/2004 |
| WO | WO2004103189 | 12/2004 |
| WO | WO2007064906 | 6/2007 |
| WO | WO2007053516 | 10/2007 |
| WO | WO2008006084 | 1/2008 |
| WO | WO2008043044 | 4/2008 |
| WO | WO2008043917 | 4/2008 |
| WO | WO2009009617 | 1/2009 |
| WO | WO2010011832 | 1/2010 |

OTHER PUBLICATIONS

P. Schauer et al., "New applications for endoscopy: the emerging field of endoluminal and transgastric bariatric surgery," Surgical Endoscopy, Accepted Jun. 7, 2006.

Richard Berges et al., "Alternative Minimalinvasive Therapien Beim Benignen Prostatasyndrom", medizin, Jg, 104 heft 37, Sep. 14, 2007.

Rudolf Hartung, et al., Instrumentelle Therapie der benegnen Prostatahyperplasie, Medizin, Deutsches Arzteblatt 97, Heft 15, Apr. 14, 2000.

Klaus Hofner, et al., "Operative Therapie des benignen Prostatasyndroms", Medizin, Dtsch Arztebl 2007; 194(36):A2424-9.

R. Hubmann, Geschichte der transurethralen Prostataeingriffe, Geschichte der Medizin, Urologe [B} 2000 40:152-160.

U. Jonas, et al. Benigne Prostatahyperplasie, Der Urologe 2006, [Sonderheft] 45: 134-144.

O.A. Bacharova, et al. "The Effect of Rhodiolae Rosea Extract on Incidence Rate of Superficial Bladder Carcinoma Relapses", Kozin 1995.

S. Kruck, et al., "Aktuelle Therapiemoglichkeiten des Benignen Prostata-Syndroms", J Urol Urogynakol 209; 16 (1):19-22.

Osamu Miyake, "Medical Examination and Treatment for BPH", Pharma Med vol. 22, No. 3, 2004, p. 97-103.

Ohashi Teruhisa, "Urinary Dysfunction by Lower Urinary Tract Obstruction in Male", Pharma Medica vol. 8 No. 8, p. 35-39.

O. Reich, et al., "Benignes Prostatasyndrom (BPS)", er Urologe A Issue vol. 45, No. 6, Jun. 2006, p. 769-782.

Daito Takashi, "Low-Invasive Treatment for BPH", Medico vol. 34, No. 10 p. 366-369.

Trapeznikov et al., "New Technologies in the Treatment of Benign Prostatic Hyperplasia", Urologia Nefrol (Mosk), Jul.-Aug. 1996 (4): 41-47.

Koyanagi Tomohiko, et al., "Surgery View of 21st Century", Urological Surgery, vol. 84, No. 1 p. 47-53.

Borzhievski et al., "Tactics of the Surgical Treatment of Patients With Prostatic Adenoma and Acute Urinary Retention", Urologia Nefrol (Mosk)., Jan.-Feb. 1987 (1): 39-43.

Yeung, Jeff, "Treating Urinary Stress Incontinence Without Incision with Endoscopic Suture Anchor & Approximating Device," Aleeva Medical, Inc., 2007.

* cited by examiner

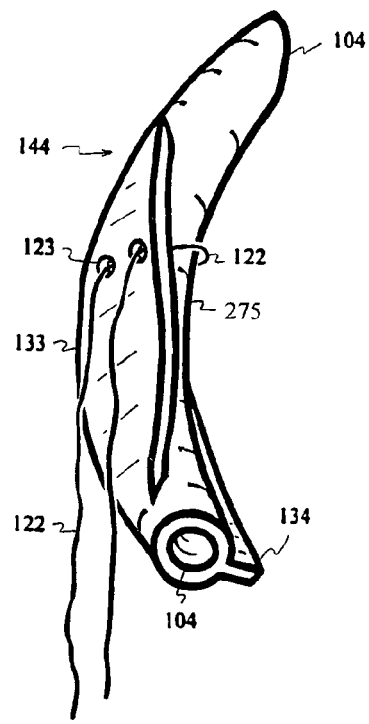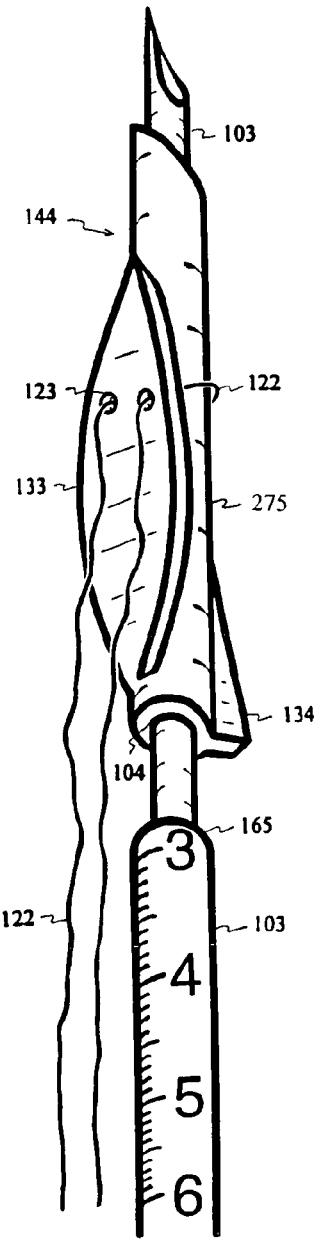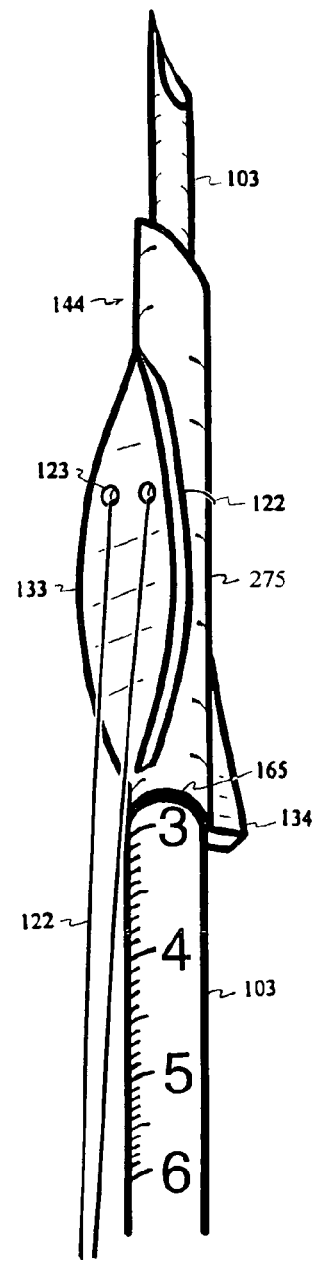
Figure 3
Figure 4
Figure 5

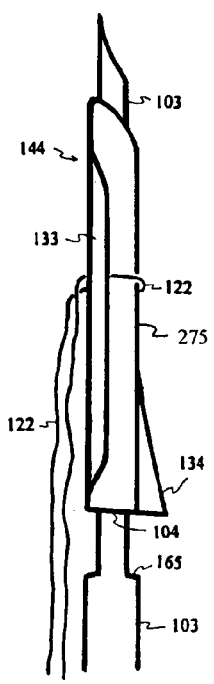 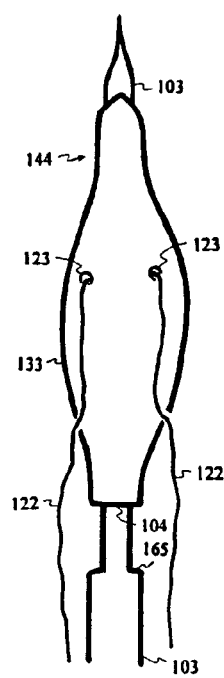 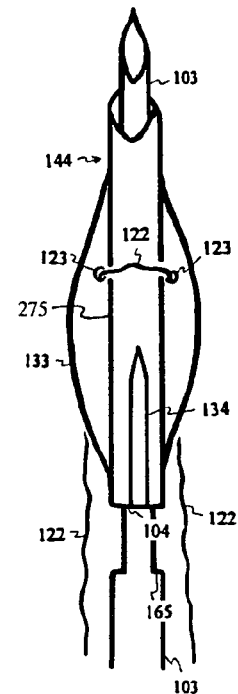
Figure 6　　　　　Figure 7　　　　　Figure 8
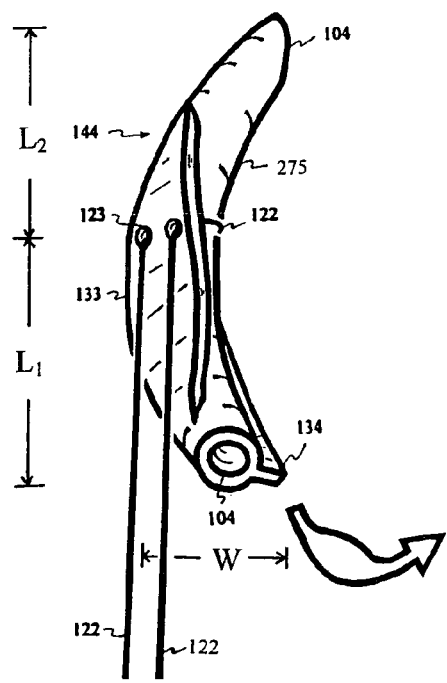
Figure 9

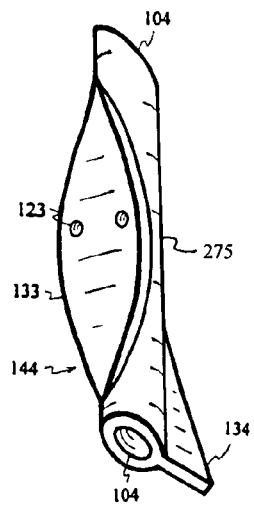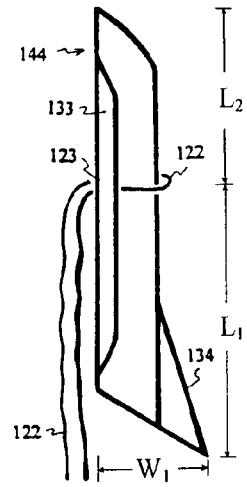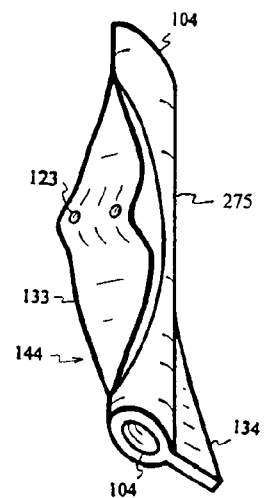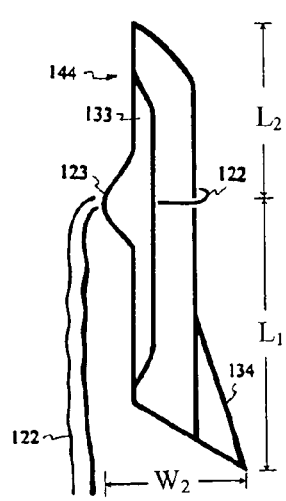
Figure 36  Figure 37  Figure 38  Figure 39
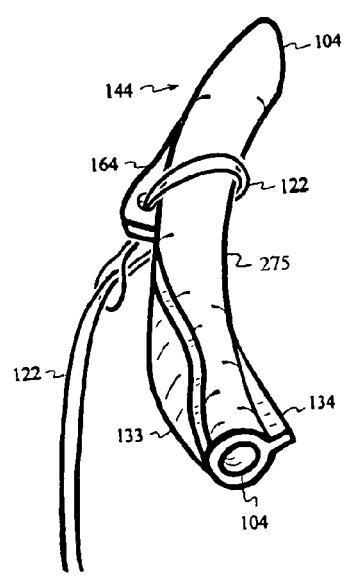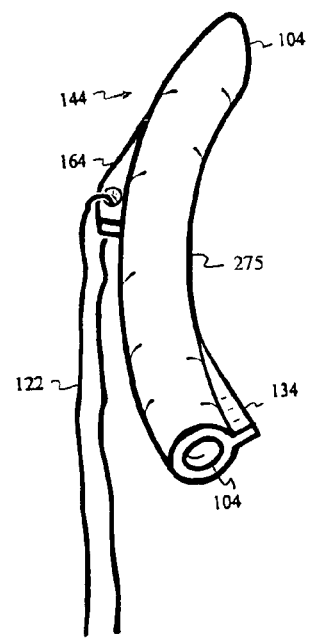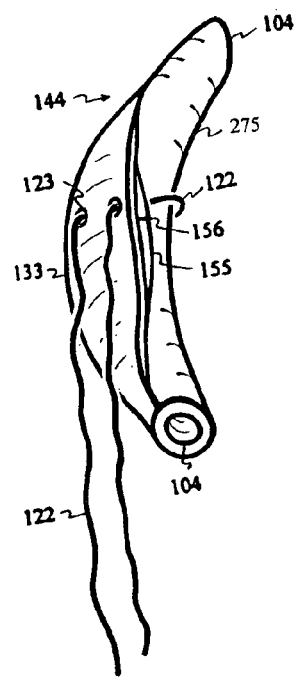
Figure 40  Figure 41  Figure 42

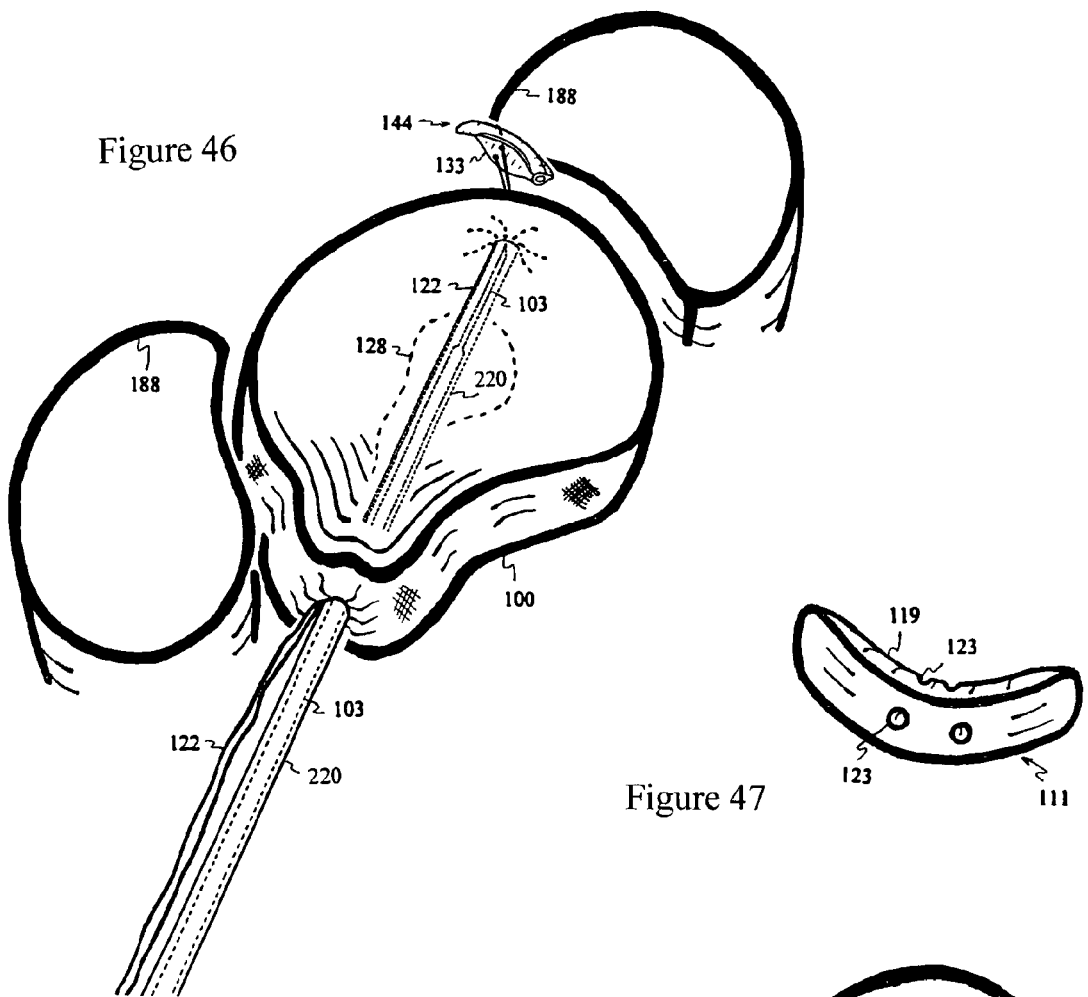
Figure 46
Figure 47
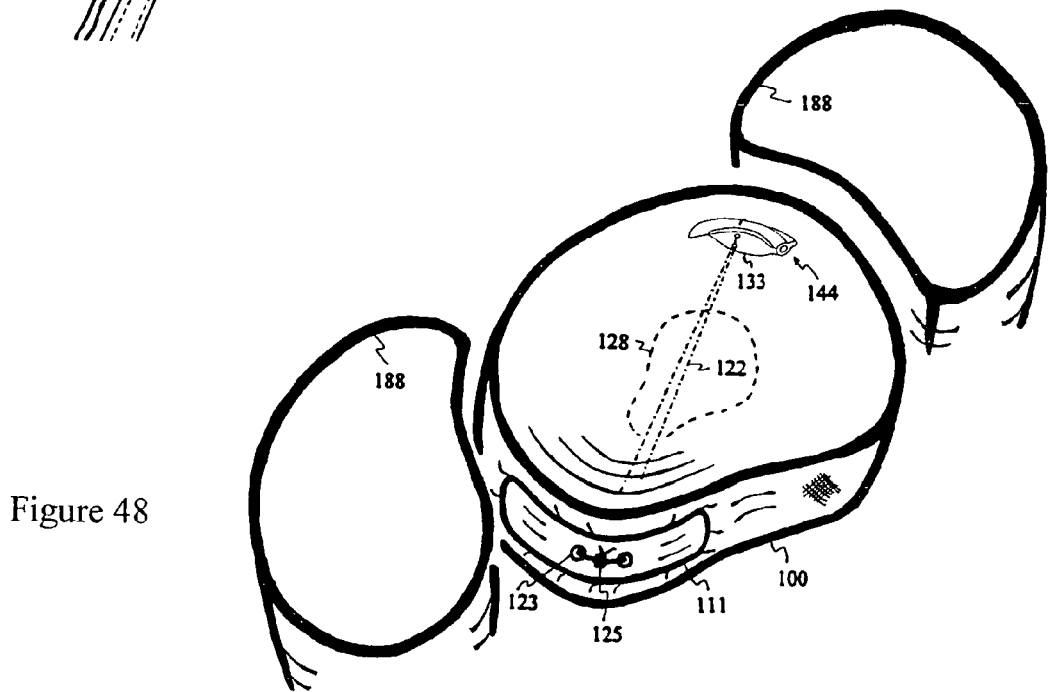
Figure 48

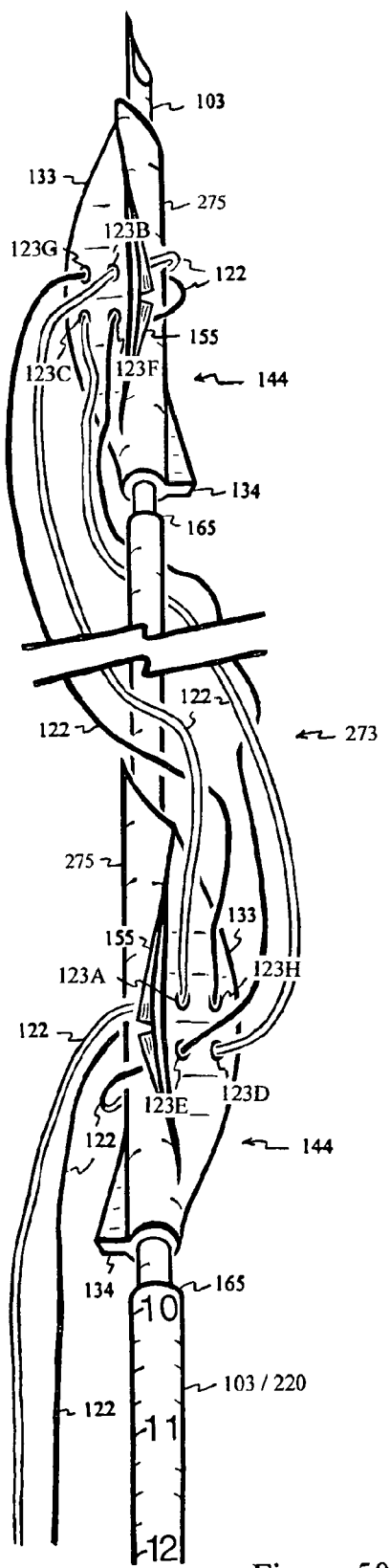
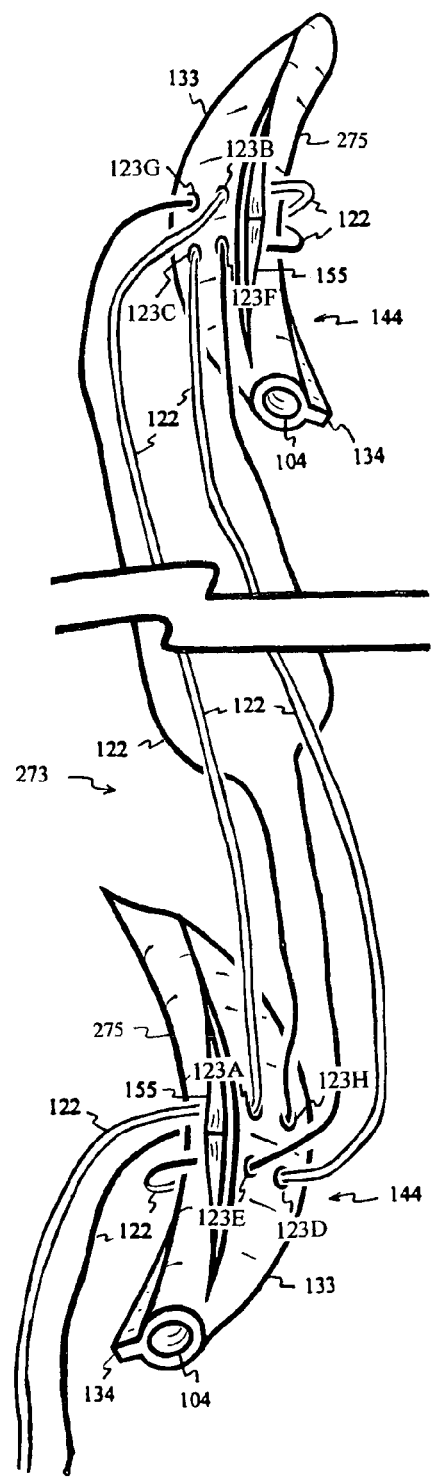
Figure 50
Figure 51

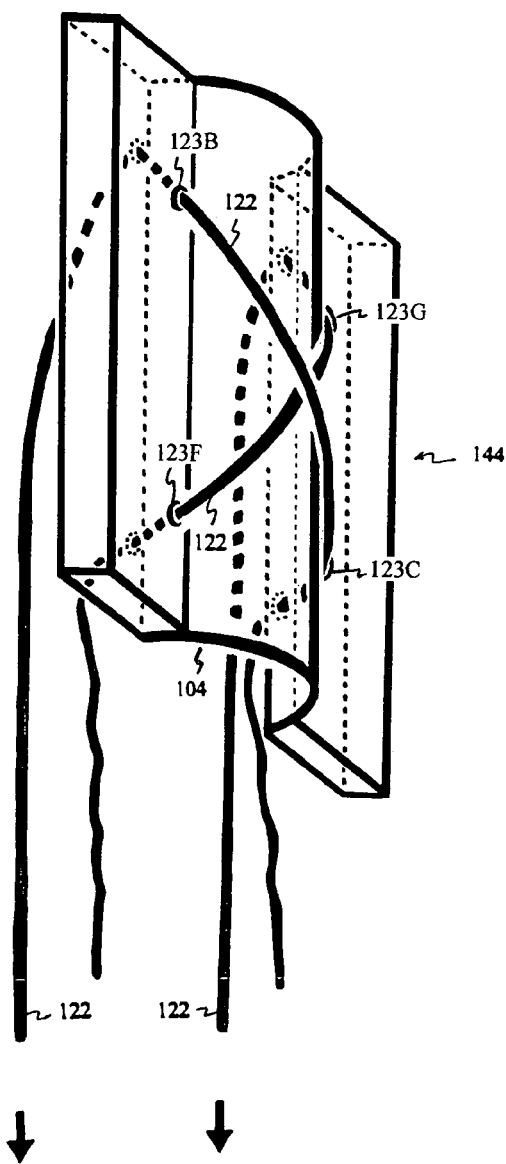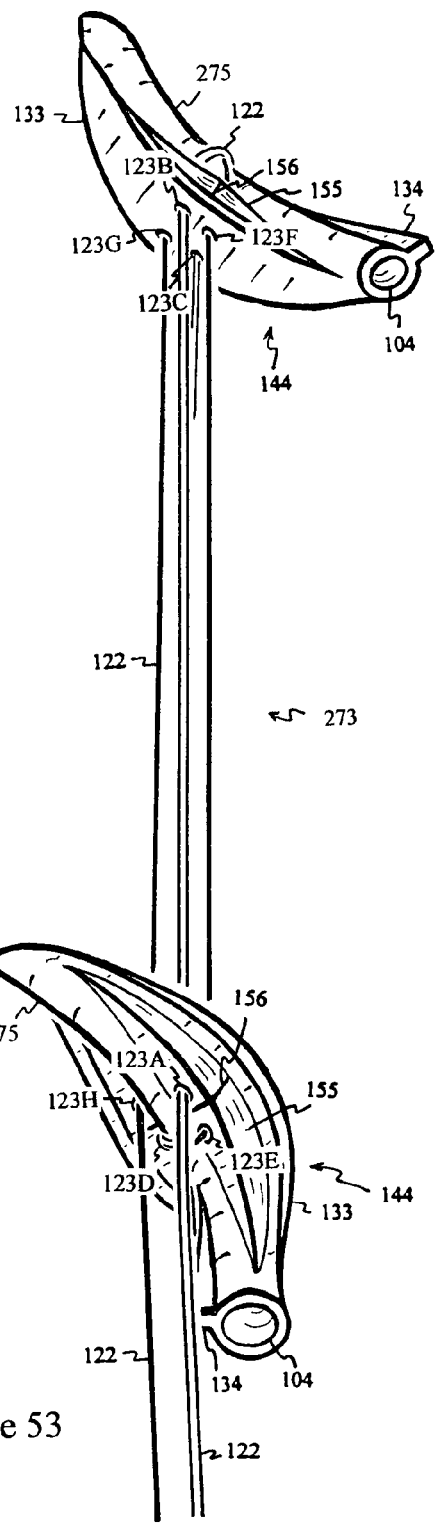
Figure 52
Figure 53

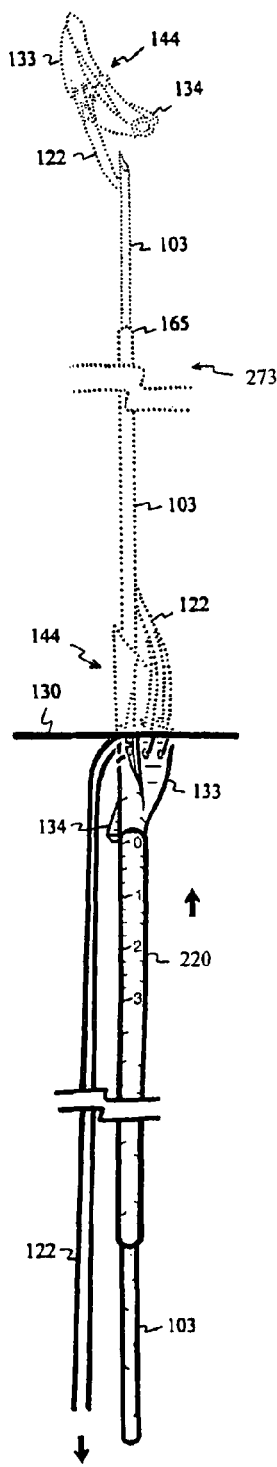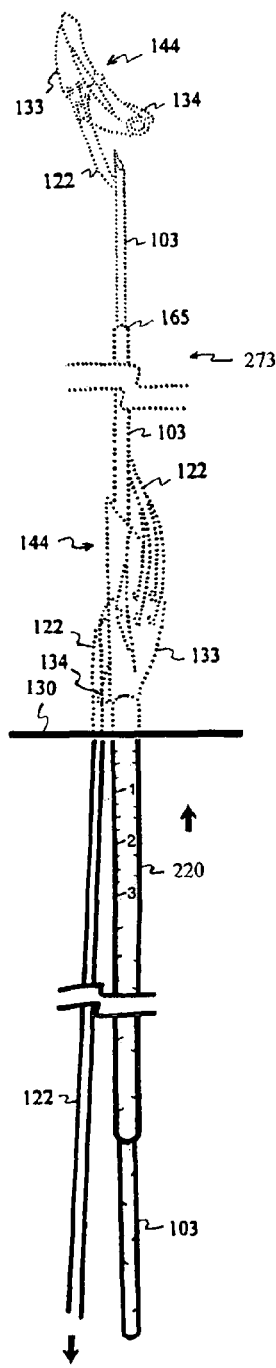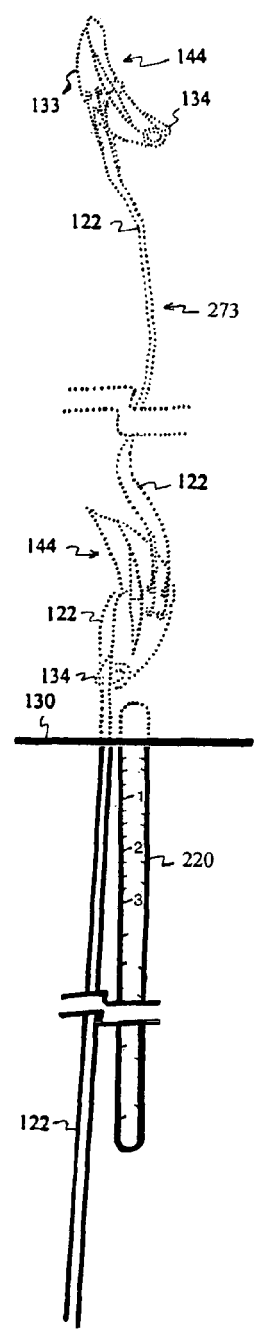
Figure 56
Figure 57
Figure 58

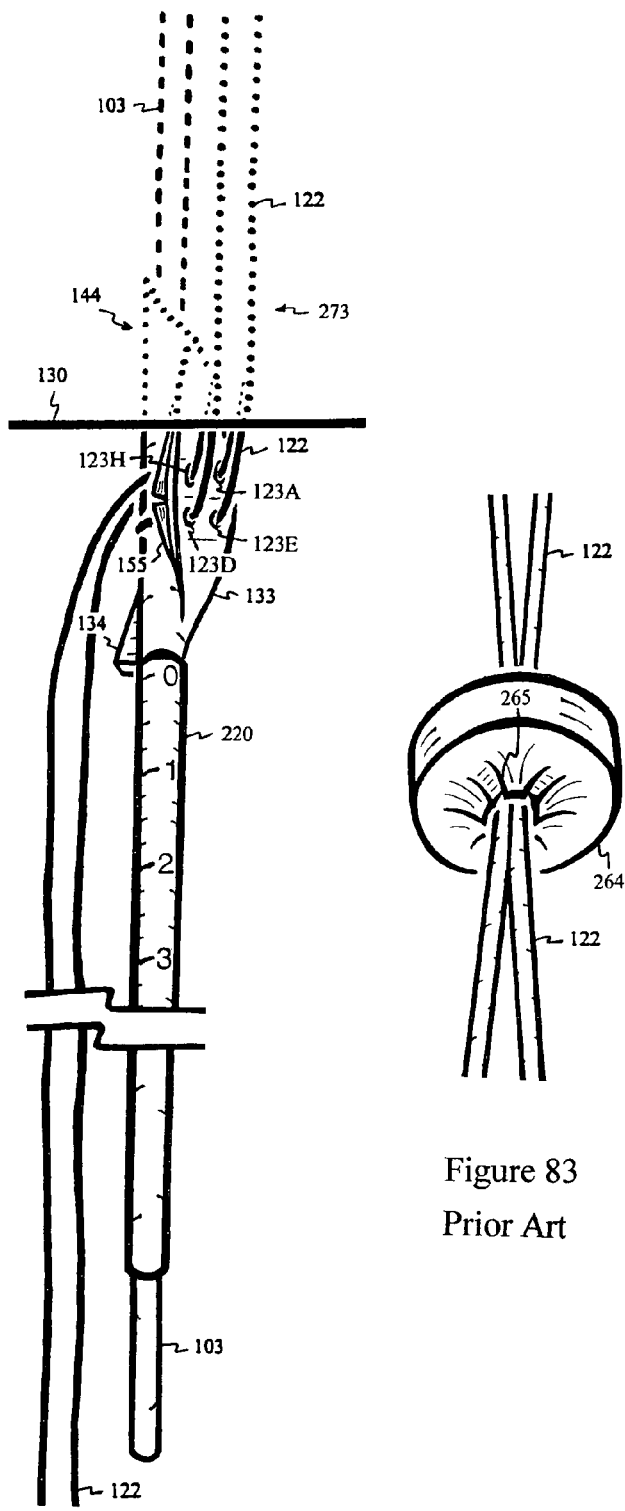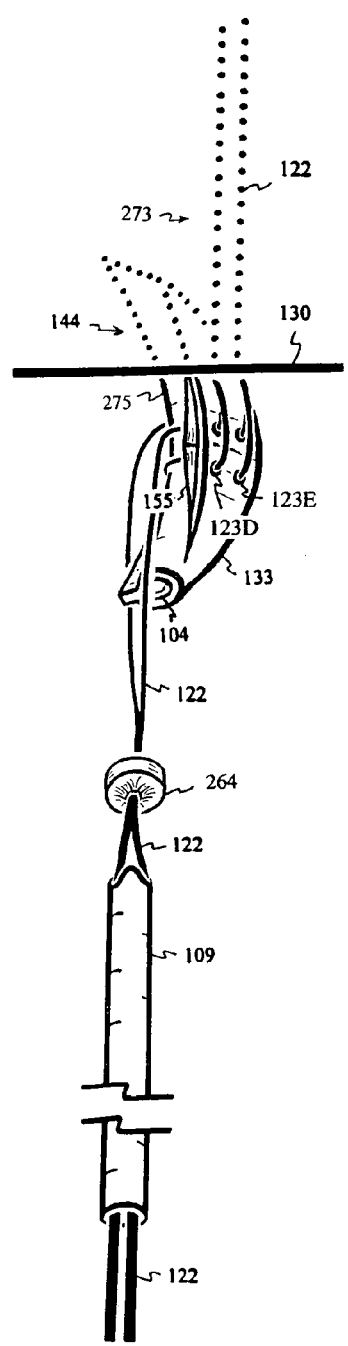
Figure 82
Figure 83
Prior Art
Figure 84

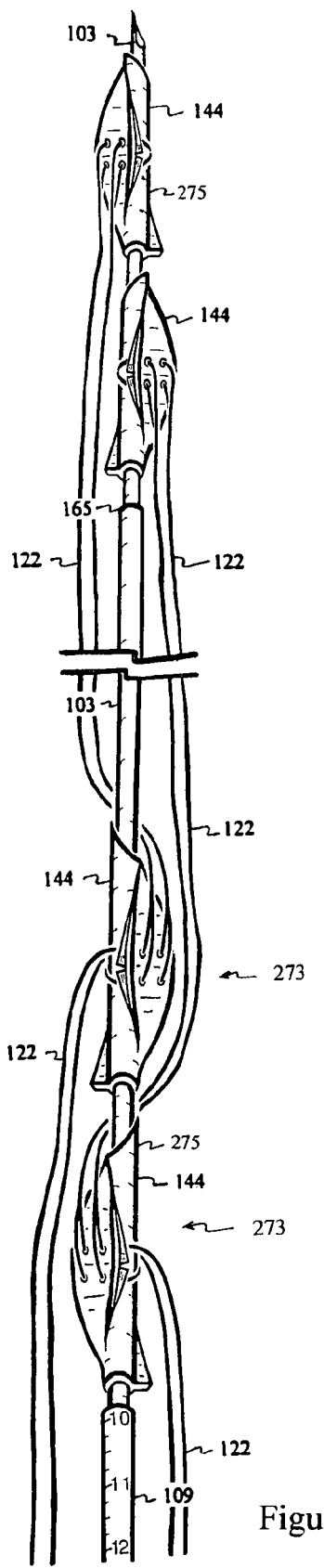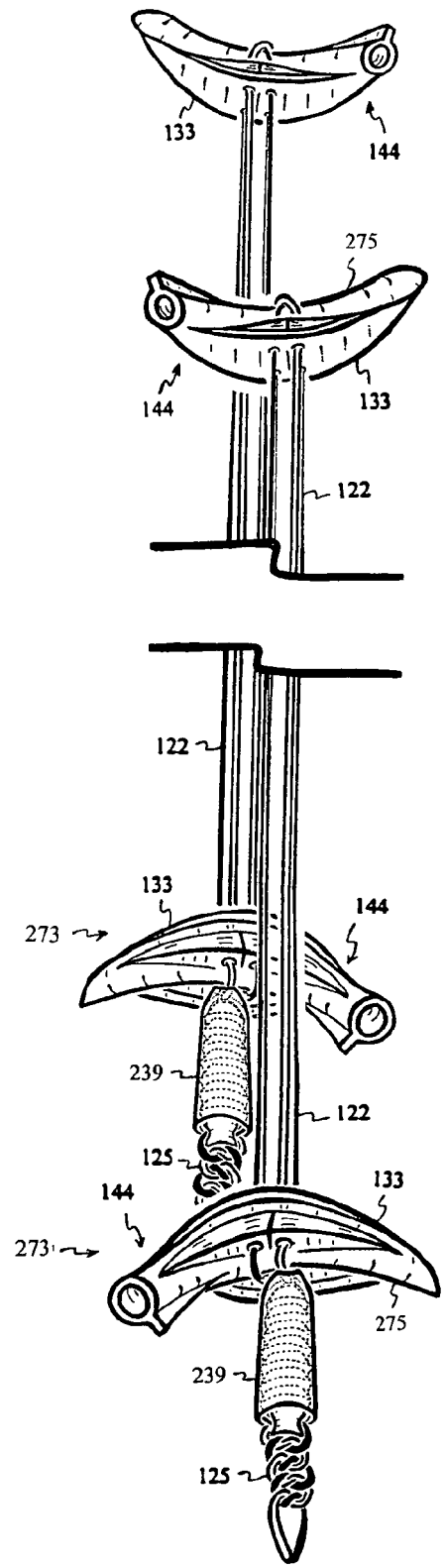
Figure 90
Figure 91

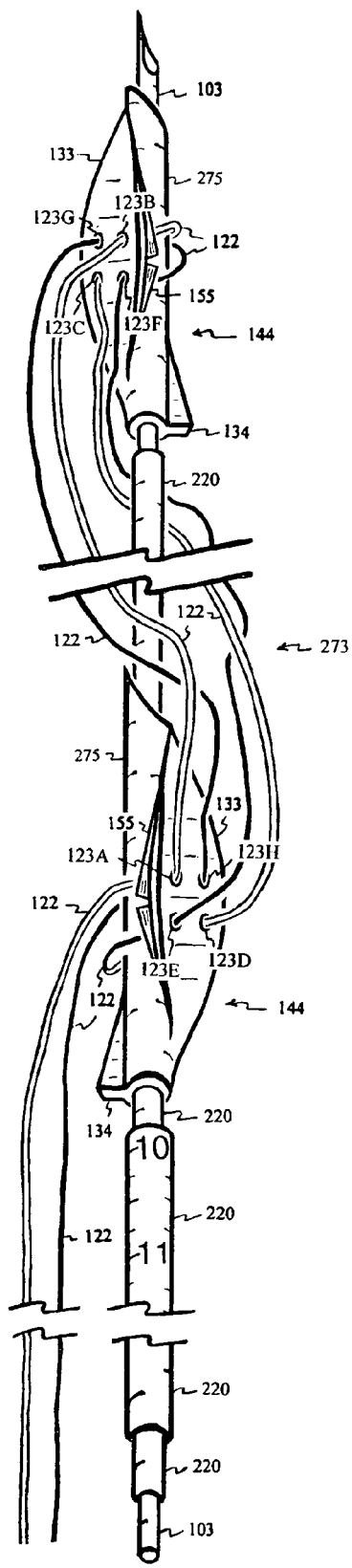
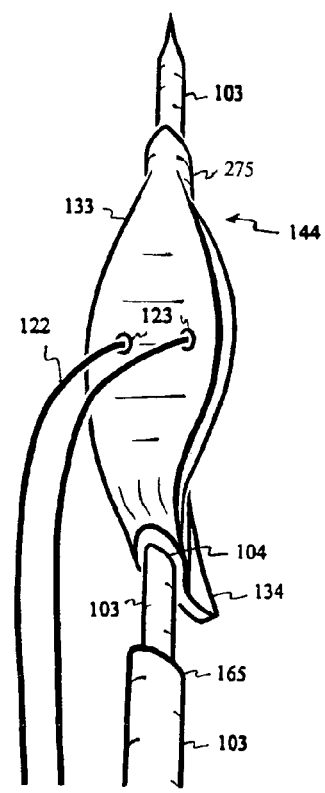
Figure 93
Figure 92
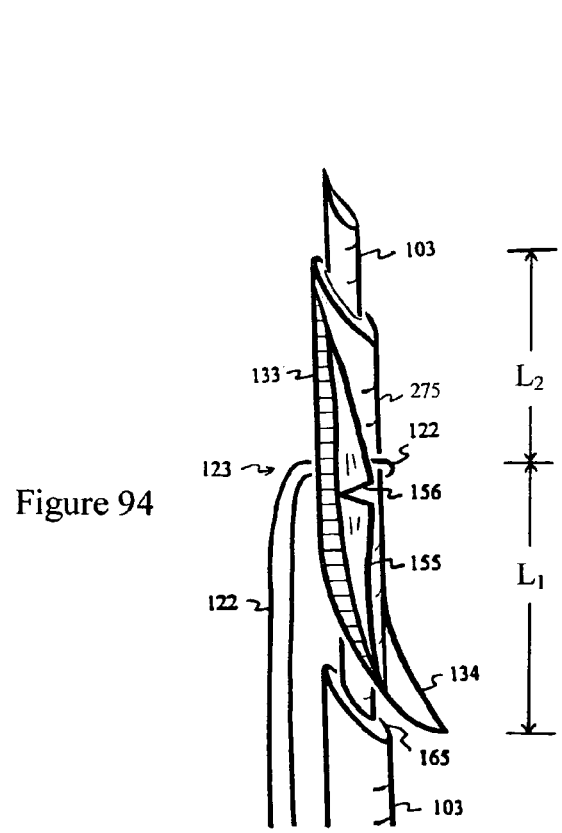
Figure 94

US 8,777,992 B2

METHODS FOR ANCHORING SUTURE AND APPROXIMATING TISSUE

CROSS REFERENCES

This application is a continuation application of pending U.S. Ser. No. 12/803,110, filed Jun. 19, 2010, which is a divisional application of U.S. Ser. No. 10/914,059, now U.S. Pat. No. 7,766,939, filed on Aug. 5, 2004, which is a continuation of PCT Application serial number PCT/US02/41399 filed Dec. 24, 2002, which claimed priority of U.S. Application 60/364,947 filed on Mar. 14, 2002.

FIELD OF INVENTION

This invention relates to minimally invasive methods for inserting suture anchors and approximating tissues.

BACKGROUND

Suture anchors have been developed for anchoring sutures in endoscopic or arthroscopic surgery through single sided access. Most prior art suture anchors are delivered from a lumen of a needle or a tubular device. Prior art include U.S. Pat. No. 4,235,238 by H. Ogiu et al., issued on Nov. 25, 1980, U.S. Pat. No. 4,741,330 by J. Hayhurst, issued on May 3, 1988, U.S. Pat. No. 4,669,473 by W. Richards et al., issued on Jun. 2, 1987, U.S. Pat. No. 5,800,445 by K. Ratcliff et al., issued on Sep. 1, 1998, U.S. Pat. No. 5,041,129 by J. Hayhurst et al., issued on Aug. 20, 1991, U.S. Pat. No. 5,845,645 by P. Bonutti, issued on Dec. 8, 1998, U.S. Pat. RE36,974, reissued on Nov. 28, 2000, and U.S. Pat. No. 6,312,448 by P. Bonutti, issued on Nov. 6, 2001. Since the anchors reside within the lumen of the delivery device, the size of the needles or tubular members is correspondingly larger, making tissue penetration more difficult and traumatic.

Several prior art anchors reside outside and around a needle. For delivery, a push rod is used to push along one side of the suture anchor, sliding along the needle into the tissue. A suture connected at the opposite side of the push rod is used to pull the anchor as the anchor is being pushed by the push rod. A series of patents by P. Bonutti, U.S. Pat. No. 5,814,072, issued on Sep. 29, 1998, U.S. Pat. No. 5,948,002, issued on Sep. 7, 1999, U.S. Pat. No. 6,033,430, issued on Mar. 7, 2000 and US patent application publication number US2001/0002440, publication date: May 31, 2001, proposed the push and pull method to pivot the anchor within tissue. Pivoting of an anchor within tissue is classified as partial-thickness suture fastening. To facilitate instant pivoting, the suture is connected close to both distal and proximal ends of the anchor to provide favorable leverage for anchor rotation. FIG. 1 depicts the prior art 235, which has completed the rotation within tissue. The suture 122 is looped near or at both ends of the anchor 235, as depicted in the prior art patents. For favorable leverage, the strands of suture 122 connected to the anchor 235 are widely spaced apart. As tension is applied to the suture 122, the strands of suture 122 spread open, as indicated by the shaded area 236, opening or pushing out the tissue 130 along the path of anchor 235 entry. Especially within soft tissue, the widely spaced sutures 122 wedge open the tissue directly above the anchor 235. As a result, the pullout strength of the anchor 235 is likely to be low. The probable mode of failure is likely to be anchor 235 pullout, as depicted in FIG. 2, rather than suture 122 breakage. While the widely spaced suture 122 provides favorable leverage for rapid rotation, it appears to sacrifice the strength of tissue anchoring.

Another prior art suture anchor, U.S. Pat. No. 5,626,614 by C. Hart, issued on May 6, 1997, also resides outside and around a needle. Hart's invention is designed for fastening or proximating tissues separated by two distinct walls, such as the stomach and abdominal walls, using full-thickness fastening. Unfortunately, most tissue within the body adheres to adjacent tissue with no clear separation, space or cavity. Therefore, full-thickness anchor pivoting to fasten or proximate two tissues has limited use.

SUMMARY OF INVENTION

Organs and/or tissues, especially in urology, are virtually adhere to each other. This invention is capable of anchoring a suture in either partial- or full-tissue thickness fastening, without the cumbersome manipulations of the suture or delivery device as described in prior art. In addition, the suture anchor contains a platform designed to improve anchoring strength within tissue.

A curved anchor made with elastic material contains a lumen for the needle. A fin protrudes from one side and a platform covers the opposite side of the anchor. The fin is on the concave side and at the proximal end, while the platform is on the convex side of the curved anchor. A suture passes through an opening in the platform, loops around the concave side of the anchor, and exits through another opening in the platform. As a result, both strands of the suture can be pulled from the convex side of the anchor.

The suture anchor is resiliently straightened by a rigid needle inserted through the lumen of the anchor. The needle contains a widened portion or a step to prevent the anchor from sliding up the needle. The needle is used to deliver the anchor by puncturing into tissue. At a proper depth, the needle can then be withdrawn. The protruded fin is tapered for tissue insertion, but behaves as a tissue snagging barb, hooking onto the tissue and resisting pullout. As a result, the needle withdrawal strips the anchor off the needle, and at the same time deploys the anchor within the tissue at the proper depth.

The anchor resumes the elastic curvature within the tissue after withdrawal of the rigid needle. The fin at the proximal end of the concave curvature is laterally pressed into the adjacent tissue, while the central portion of the convex curvature connecting to the suture is pushed in the opposite direction further away from the fin. In essence, curvature resumption within tissue increases the distance between the fin and the openings for the suture, as the fin is pressed laterally into the tissue. When the strands of suture are pulled on the convex side of the anchor, the curved anchor begins to rotate within tissue from a vertical, or inserting position, to a horizontal, or fastening position. The platform is also repositioned from vertical to horizontal to greatly resist pullout during tissue fastening and repair.

Multiple anchors can be linked by a suture and delivered in series into tissue. When the suture is pulled, the anchors draw close to each other to shorten or approximate the pierced tissue.

REFERENCE NUMBER

| | |
|---|---|
| 100 | Intervertebral disc |
| 101 | Urethra |
| 102 | Urethropelvic ligament |
| 103 | Stepped or smooth needle |
| 104 | Lumen of suture anchor |
| 109 | Plunger |

| | |
|---|---|
| 111 | Disc compressor |
| 112 | Bladder neck |
| 113 | Mucosa |
| 114 | Vagina |
| 115 | Pubic symphysis |
| 117 | Urine |
| 118 | Cancellous bone |
| 119 | Annular contact surface |
| 122 | Suture |
| 123 | Opening for suture |
| 125 | Suture knot |
| 126 | Cortical bone |
| 127 | Bladder |
| 128 | Nucleus pulposus |
| 130 | Soft tissue |
| 131 | Lateral wall of urethra |
| 132 | Rectum |
| 133 | Platform of anchor |
| 134 | Fin of anchor |
| 138 | Tendon or ligament |
| 144 | Suture anchor |
| 150 | Lumen of urethra |
| 151 | Posterior wall of urethra |
| 152 | Anterior wall of urethra |
| 153 | Needle indentation |
| 154 | Catheter |
| 155 | Bend stop |
| 156 | Gap of bend stop |
| 157 | Incision |
| 159 | Handle of positioning device |
| 160 | Lifting hand piece |
| 161 | Uterus |
| 163 | Uterus positioning tool |
| 164 | Suture attachment |
| 165 | Step of trocar or needle |
| 171 | Distal round end |
| 172 | Shaft of positioning device |
| 185 | Trocar guide |
| 188 | Psoas major muscle |
| 196 | Retractor |
| 220 | Sleeve of trocar or needle |
| 221 | Grippers on the sleeve |
| 235 | Prior art suture anchor |
| 236 | Area of suture spread |
| 237 | One-way grip |
| 238 | Suture passage of the grip |
| 239 | Suture lock |
| 240 | Cone hole |
| 241 | Gripper |
| 245 | Knot pusher |
| 246 | Inner tube |
| 247 | Outer tube |
| 248 | Side window |
| 249 | Sharp edge |
| 250 | Suture cutting device |
| 251 | External sphincter |
| 252 | Internal sphincter |
| 253 | Cardinal ligament |
| 254 | Sacrouterine ligament |
| 255 | Fascia |
| 256 | Ovary |
| 257 | Round ligament |
| 258 | Fallopion tube |
| 259 | Grasping device |
| 260 | Guide arm |
| 261 | Pointer |
| 262 | Glide track |
| 263 | Endoscope |
| 264 | Suture gripping device |
| 265 | Flap |
| 266 | Cone |
| 267 | Loop |
| 268 | Scar tissue |
| 269 | Lumen of needle |
| 270 | Collagen bundles |
| 271 | Cervix |
| 272 | Adipose tissue |
| 273 | Approximating device |
| 274 | Retropubic space |
| 275 | Body of anchor |

BRIEF DESCRIPTION OF THE DRAWINGS

FIG. 3 depicts a suture anchor 144 with an elastically curved body 275, lumen 104, a fin 134, a relatively flat platform 133 and two openings 123 for a suture 122.

FIG. 4 depicts the elastic body 275 being resiliently straightened by a trocar or needle 103 inserted through the lumen 104 of the anchor 144.

FIG. 5 depicts the resiliently straightened anchor 144 resting on a step 165 of the needle 103.

FIG. 6 shows a side view of the anchor 144 with the stepped needle 103. The distal tip of the anchor 144 is beveled. The platform 133 and fin 134 are tapered for tissue penetration.

FIG. 7 depicts the top view of the anchor 144 with suture 122 exiting from openings 123 on the elliptical platform 133 tapered at both distal and proximal ends.

FIG. 8 shows the bottom view of the anchor 144, indicating the tapered distal tip, and looping of the suture 122 under the anchor 144 to distribute suture 122 tension.

FIG. 9 depicts the rotational direction of the curved suture anchor 144 within tissue, as tension is applied to suture 122.

FIG. 36 shows a straight anchor 144 with a large fin 134 and a tapered proximal end.

FIG. 37 shows a side view of the straight anchor 144, as shown in FIG. 36, with dimensions $W_1$, $L_1$ and $L_2$.

FIG. 38 shows another straight anchor 144 with elevated suture openings 123.

FIG. 39 shows a side view of the anchor 144 with elevated suture openings 123, as shown in FIG. 38, with dimensions $W_2$, $L_1$ and $L_2$.

FIG. 40 depicts a curved suture anchor 144 with a protruded suture attachment 164, a fin 134 and a small platform 133.

FIG. 41 depicts another curved suture anchor 144 with the protruded suture attachment 164 but without a platform.

FIG. 42 shows a curved suture anchor 144 without a fin.

FIG. 46 depicts pushing of the anchor 144 by the sliding sleeve 220 to expel the suture anchor 144 beyond the distal edge of the disc 100.

FIG. 47 depicts a disc compressor 111 with two openings 123 for a suture 122 and a cylindrical or blunt region 119 to compress the disc 100.

FIG. 48 depicts bulge compression by fastening the disc compressor 111 with a suture 122 secured by the anchor 144 outside the disc 100.

FIG. 50 shows a double-stepped 165 needle 103 resiliently straightening two anchors 144 with a suture 122 arrangement similar to FIG. 49.

FIG. 51 indicates deployment of the anchors 144 within tissue after withdrawal of the needle 103.

FIG. 52 shows orientation of the suture 122 designed to resist sliding through holes 123B and 123G when the anchor 144 is in a vertical or inserting position.

FIG. 53 depicts anchors 144 pivoting within tissue as the suture 122 is pulled.

FIG. 56 depicts proximal anchor 144 insertion by pushing the sleeve 220, and distal anchor 144 pivoting by pulling on the suture 122.

FIG. 57 shows complete insertion of the proximal anchor 144 into the tissue 130 by pushing the sleeve 220 and pulling suture 122.

FIG. 58 indicates withdrawal of the needle and curvature resumption of the proximal anchor 144 within tissue 130.

FIG. 82 depicts partial insertion of the proximal anchor 144 of the approximating device 273 into tissue 130 by advancing the sleeve 220.

FIG. 83 shows a prior art suture-gripping device 264 with flaps 265 biased against the upward tensile force applied to the suture 122.

FIG. 84 indicates the suture gripping device 264 and plunger 109 positioned to tighten the anchors 144 of the approximating device 273 after withdrawal of the needle.

FIG. 90 depicts double approximating devices 273 loaded on a single needle 103.

FIG. 91 shows fastening of the double approximating devices 273 after insertion of a single needle 103.

FIG. 92 shows an inner sleeve 220 for deploying the distal anchor 144 and an outer sleeve 220 for deploying the proximal anchor 144 from the needle 103.

FIG. 93 depicts the proximal end of a platform 133 tapered over the proximal end of the body 275 to facilitate pivoting and rotation within tissue.

FIG. 94 shows the side view of the tapered platform 133 over the proximal end of the body 275 supported by a shape-matching step 165.

DETAILED DESCRIPTION OF THE EMBODIMENTS

Figure 1:
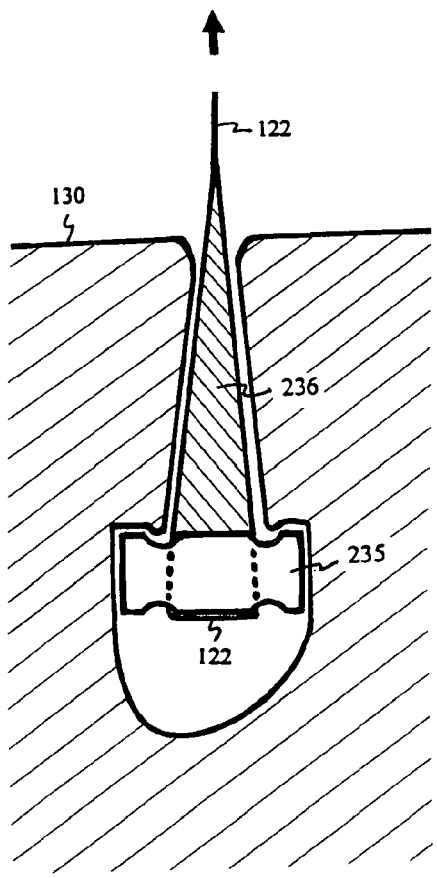
FIG. 1 depicts the tissue 130 opening above the prior art anchor 235, caused by spreading 236 of the sutures 122 as tension is applied.
Figure 2:
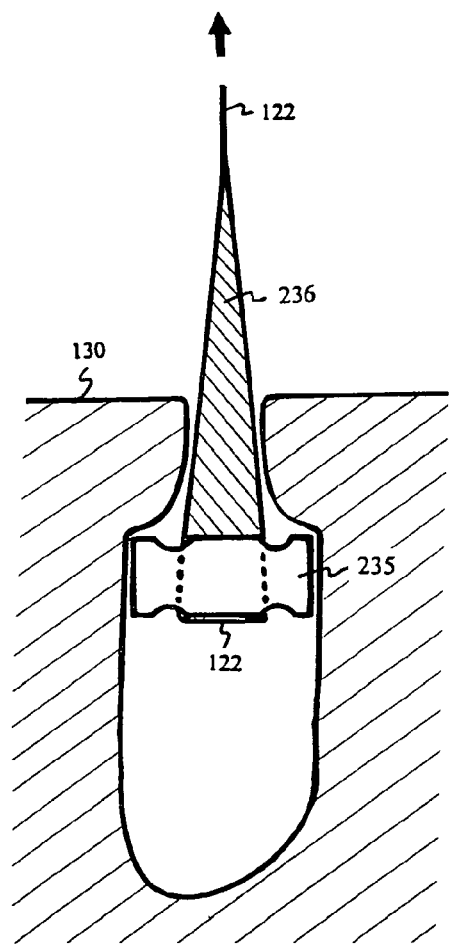
FIG. 2 depicts prior art anchor 235 pullout as a probable result of the tissue 130 opening directly above the prior art anchor 235.

A curved anchor 144 is made with elastic material containing a longitudinal lumen or passage 104, a fin 134 at or near the proximal end, and a relatively flat platform 133 on the convex side of the curvature with two openings 123 for a suture 122, as shown in FIG. 3. Through the openings 123 on the platform 133, the suture 122 is looped around the concave side of the curved anchor 144 for tension distribution. FIG. 4 depicts a relatively rigid trocar or needle 103 inserted through the lumen 104 to resiliently straighten the elastic anchor 144. The needle 103 is marked with measuring units, visible under endoscope, to indicate depth of needle 103 penetration into tissue. The distal portion of the needle 103 is sized and configured to fit into the lumen 104 of the anchor 144. To prevent the anchor 144 from sliding up the needle 103 during tissue penetration, the cross-sectional diameter of the needle 103 is not uniform. A step 165 on the needle 103, as shown in FIGS. 4 and 5, blocks the anchor 144 from sliding upward, over the needle 103. FIG. 5 depicts the proximal end of the resiliently straightened anchor 144 resting on the step 165 of the needle 103, with the fin 134 protruding over or above the step 165. In essence, the elastic suture anchor 144 has a curved position and a straightened position.

FIG. 6 depicts a side view of the curved anchor 144 straightened by the rigid stepped needle 103. The distal tips of the anchor 144, platform 133 and fin 134 are tapered and/or beveled to accommodate tissue penetration. The proximal end of the fin 134 is designed to resist anchor 144 pull out during withdrawal of the stepped needle 103. FIG. 7 depicts the top view of the anchor 144 with an elliptical platform 133 tapered at both distal and proximal ends. The tapered distal end of the platform 133 is designed for tissue penetration spearheaded by the stepped needle 103. FIG. 8 depicts the bottom view with tapered distal ends of the anchor 144 and the fin 134 for ease of tissue penetration. The suture 122 passes through the openings 123 on the platform 133 and loops under the straightened anchor 144 to distribute tension of the suture 122. Since the suture 122 is not tied to the anchor 144, the suture 122 can slide freely, even after the anchor 144 is fastened within tissue. A sliding suture 144 can be useful, sometimes essential in tissue reattachment or other surgical manipulations.

The fin 134 serves as a reversed barb or a snag, favoring tissue penetration but resisting anchor 144 pullout. The anchor 144 is delivered by tissue piercing with the stepped needle 103, as shown in FIG. 5. The depth of anchor 144 insertion is known by the measuring units on the stepped needle 103, as shown in FIGS. 4 and 5. As the stepped needle 103 is withdrawn, the barb-like fin 134 catches, hooks or snags onto the surround tissue, allowing the anchor 144 to slide off the withdrawn stepped needle 103. The anchor 144 remains in the tissue with the suture 122 attached. In essence, the anchor 144 is delivered in the tissue simply by inserting and withdrawing the stepped needle 103.

Driven by suture 122 tension, the delivered anchor 144 is designed to rotate and fasten within tissue. After withdrawal of the stepped needle 103, the anchor 144 resumes the curved configuration, laterally pressing the pointed proximal end of the fin 134 into the tissue. Three points curved anchor 144: the suture openings 123 on top of the platform 133, the fin 134 and the distal end of the anchor 144, form a triangle. In essence, the lateral separation between the protruded fin 134 and the suture 122 connecting points or openings 123 increases with resumption of the anchor 144 curvature. The distance, W, between the suture openings 123 and the proximal end of the fin 134, as shown in FIG. 9, provides initial rotational torque, when tension is applied to the suture 122 by the surgeon. The tapered proximal end of the platform 133 is shaped for lateral tissue penetration when the anchor 144 is pulled by the suture 122. The curved arrow in FIG. 9 indicates the rotational direction of the anchor 144 within the tissue from vertical to near horizontal, about 90°, as a direct response to suture 122 tension, shown as a straight arrow. The fin 134 guides, spearheads and/or prevents the anchor 144 from twisting during rotation or pivoting within tissue, repositioning the platform 133 from being parallel with the suture 122, as shown in FIG. 5, to being near perpendicular with the suture 122 for maximum anchoring power. Anchor 144 rotation within the tissue may also be favored if $L_1$ is longer than $L_2$, where $L_1$ is the distance between the proximal end of the anchor 144 to suture openings 123, and $L_2$ is the distance between the distal end of the anchor 144 to suture openings 123. However, depending on the size and shape of the platform 133, if $L_1$ is significantly longer than $L_2$, the anchor 144 may over rotate, beyond 90°. As a result, the suture 122 would no longer be perpendicular to the platform 133, and the anchoring strength could possibly weaken.

Partial thickness suturing is common in open surgery, and rotation of the curved anchor 144 within the tissue allows the surgeon to obtain partial thickness suturing in endoscopic, arthroscopic or laparoscopic procedures. The curved suture anchor 144 is designed for: (1) elastically straightening with the stepped needle 103, (2) tissue penetration with tapered distal portions, (3) dislodging with the barb-like fin 134, (4) curvature resumption following needle 103 withdrawal, (5) rotation within the tissue driven by suture 122 tension, and (6) anchoring strength with the large platform 133.

Figure 10:
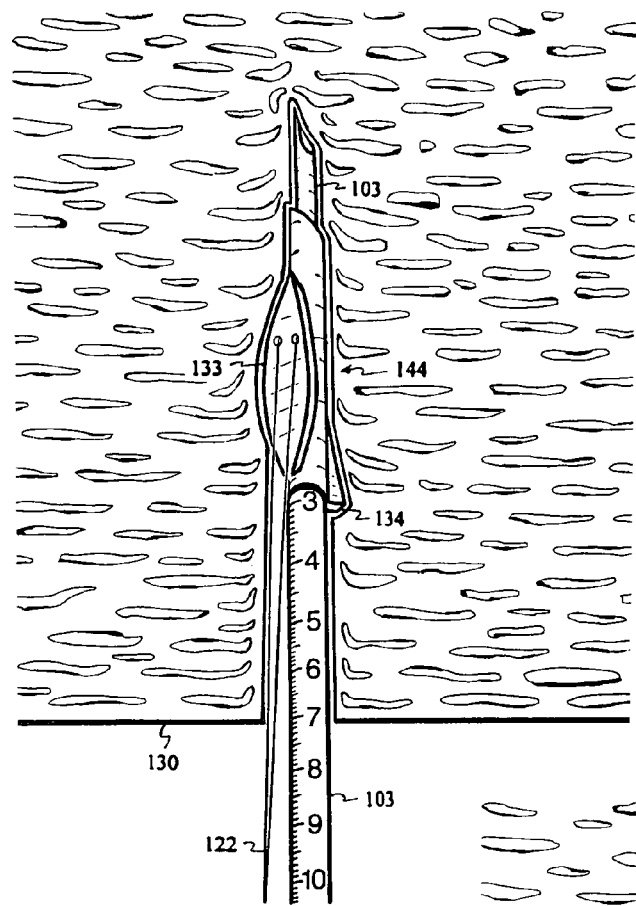
FIG. 10 depicts penetration of the stepped needle 103 loaded with the suture anchor 144 into soft tissue 130.
Figure 11:
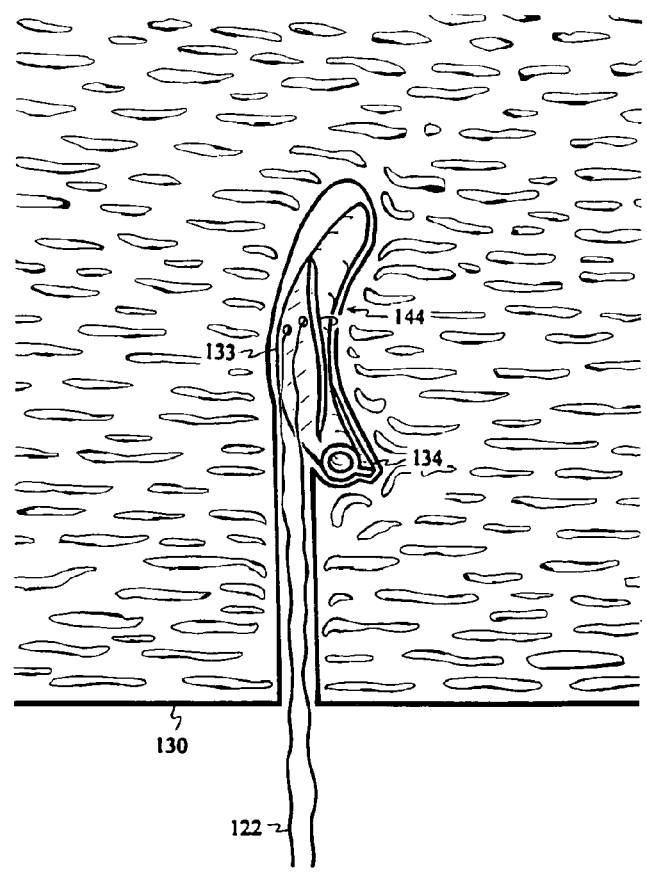
FIG. 11 depicts the anchor 144 resuming the curved configuration and pressing the fin 134 laterally into the tissue 130 after the withdrawal of the stepped needle 103.
Figure 12:
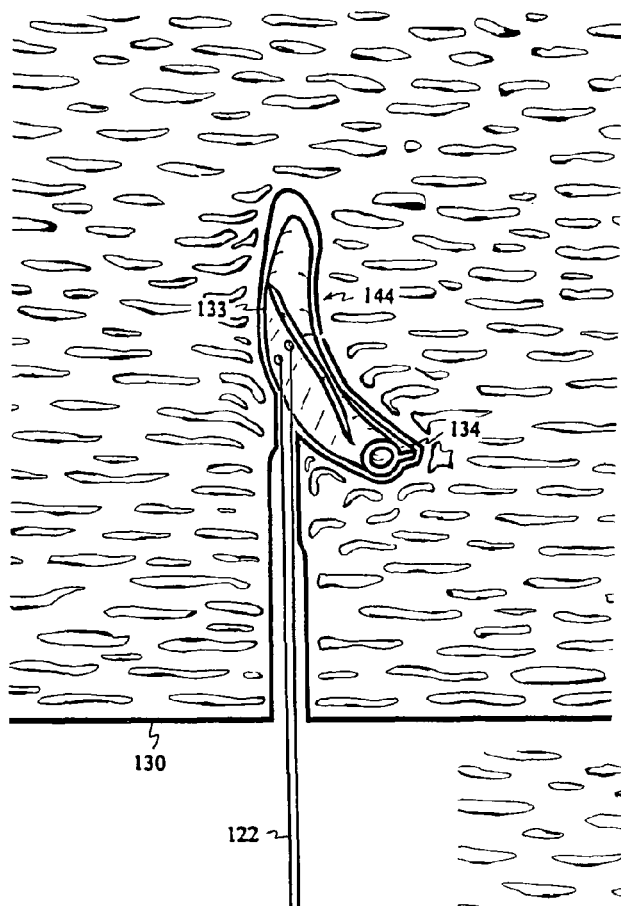
FIG. 12 depicts tension applied to the suture 122 pulling on the curved anchor 144 and driving the fin 134 further laterally.
Figure 13:
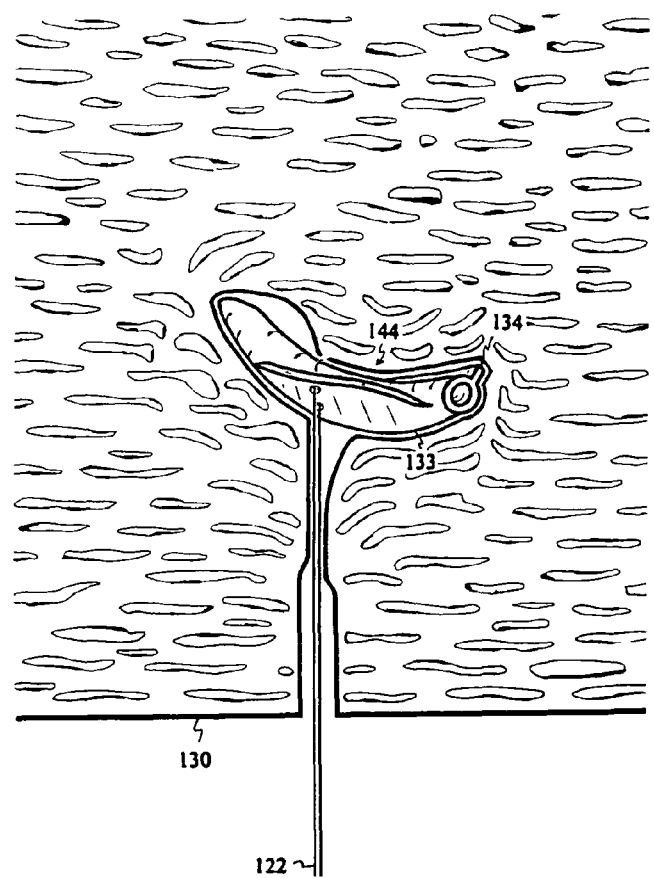
FIG. 13 depicts the tension driven rotation of the anchor 144, orienting the large and relatively flat platform 133 from a vertical to a horizontal position to resist anchor 144 pullout.

FIG. 10 depicts penetration of the stepped needle 103 loaded with the suture anchor 144 into soft tissue 130. A scale on the stepped needle 103 visible to the surgeon measures the depth of anchor 144 insertion. The fin 134 of the anchor 144 protrudes outwardly, catching the tissue 130 and preventing the anchor 144 from pulling out as the stepped needle 103 is withdrawn. In essence, withdrawal of the stepped needle 103 dislodges or strips off the anchor 144, allowing the suture anchor 144 to remain at or near the intended depth of insertion. FIG. 11 depicts resumption of the curved configuration of the anchor 144 after withdrawal of the stepped needle 103. The curvature also provides compression on the fin 134, embedding the fin 134 laterally into tissue 130. FIG. 12 depicts tension applied to the suture 122 to pull and rotate the anchor 144 from an insertion or vertical position to an anchoring or horizontal position. The initial lateral mobility is favored by (1) the curvature of the suture anchor 144, and (2) protrusion of the fin 134. During rotation, twisting of the anchor 144 along the longitudinal axis is prevented by the fin 134 and the platform 133 as both laterally penetrate into tissue 130. FIG. 13 depicts further tension applied to the suture 122, orienting the platform 133 to nearly perpendicular to the suture 122 under tension. With the large surface area of the platform 133 pressing against the tissue 130, the suture 122 is secured with good anchoring strength for surgical repair. The rotation of the anchor 144 within the tissue provides partial thickness suturing with endoscopic, arthroscopic or laparoscopic capability.

Figure 14:
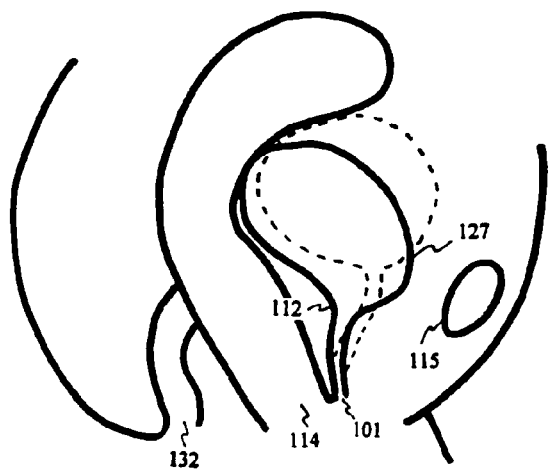
FIG. 14 indicates a normal, well-supported bladder 127 in dashed lines and a descended bladder 127 with a widened bladder neck 112 in solid lines.
Figure 15:
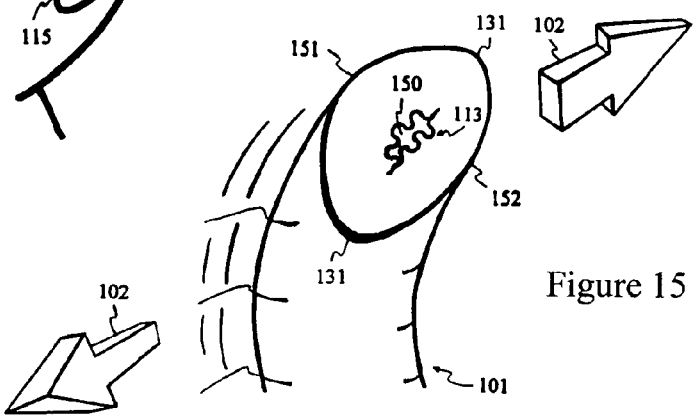
FIG. 15 shows a failed lumen 100 closure and hypermobility under stress with the urethropelvic ligament 102 pulling the lateral walls 131 of the poorly supported urethra 101.
Figure 16:
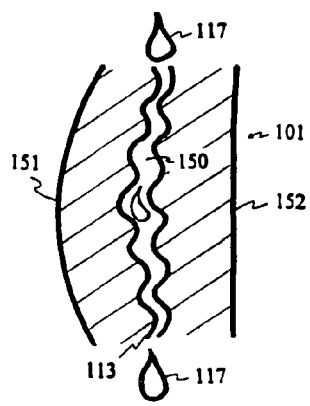
FIG. 16 indicates a mid-longitudinal view of FIG. 15 and urine 117 leakage during stress with urethropelvic ligaments pulling perpendicularly above and below the plane of the page.

It is widely believed that most of the urinary incontinence in women is related to a descended position of the bladder 127, the funneling of the bladder neck 112 and/or diminished posterior 151 urethral support. The dashed line of FIG. 14 indicates the normal position and the solid line depicts a descended position of the bladder 127 with its funnel-shaped bladder neck 112. FIG. 15 shows a failed lumen 100 closure and hypermobility under stress with the urethropelvic ligaments 102 pulling the lateral walls 131 of the poorly supported urethra 101. FIG. 16 shows the mid-sagittal view of FIG. 15 during stress, with urethropelvic ligaments pulling perpendicularly above and below the plane of the page. FIG. 16 also indicates that the section of poorly supported posterior wall 151 withdraws from mucosal 113 coaptation, leading to urine 117 leakage.

Figure 17:
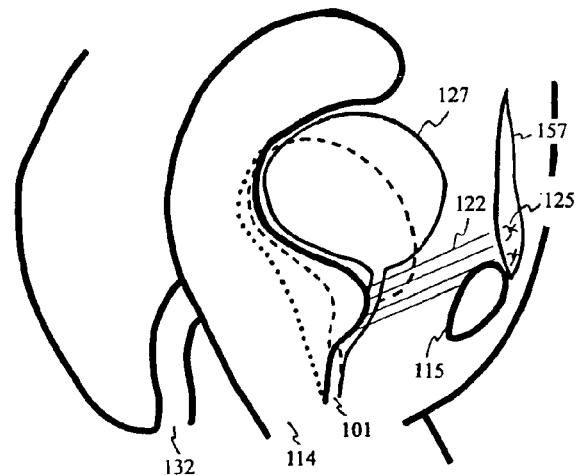
FIG. 17 shows a prior art procedure for treating urinary incontinence through a large incision 157 for passing sutures 122 and pulling the vagina 114 forward to support or compress the posterior wall of the urethra 101.
Figure 18:
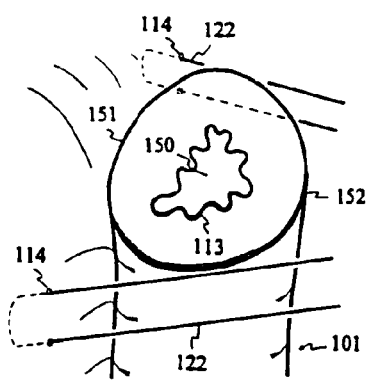
FIG. 18 depicts a section of the surgically corrected urethra 101 with sutures 122 pulling the vaginal 114 tissue to support and gently compress the urethral posterior wall 151.
Figure 19:
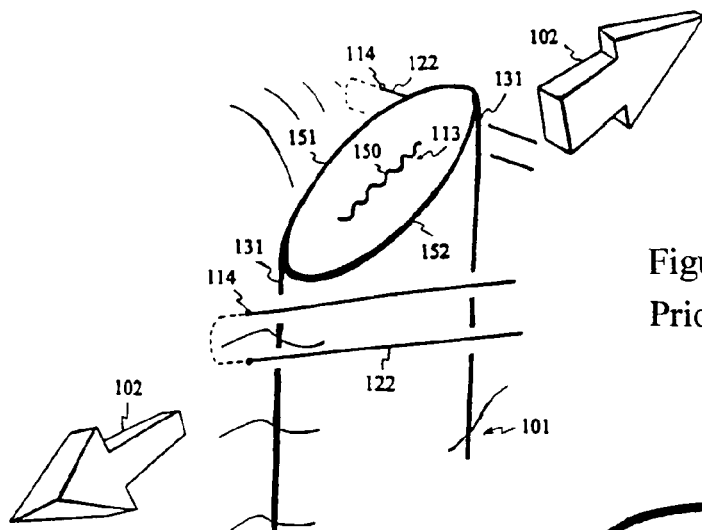
FIG. 19 indicates lumen 150 closure of the surgically corrected urethra 101 under stress, with urethropelvic ligaments 102 pulling the lateral walls 131 of the supported urethra 101.

Numerous existing surgical procedures are designed to treat urinary incontinence. The traditional surgical treatment for urinary incontinence is to add backboard support to the urethral posterior wall 151, usually by repositioning the vagina 114 with sutures 122. FIG. 17 indicates the pre-surgical position of the vagina 114 with a dotted line, and that of the urethra 101 and bladder with dashed lines. FIG. 17 also shows a large incision 157 required for repositioning and suturing both the vagina 114 and urethra 101 toward the abdominal wall. The post-surgical positions of the vagina 114 and backboard-supported urethra 101 are depicted with solid lines. The sutures 122 are knotted 125 to fascia or ligament on the abdominal wall. FIG. 18 indicates a section of the backboard-supported posterior wall 151. This significantly invasive procedure provides the backboard support needed for lumen 150 closure during stress with concurrent pulling of the urethropelvic ligaments 102 to prevent urine leakage, as shown in FIG. 19.

Figure 20:
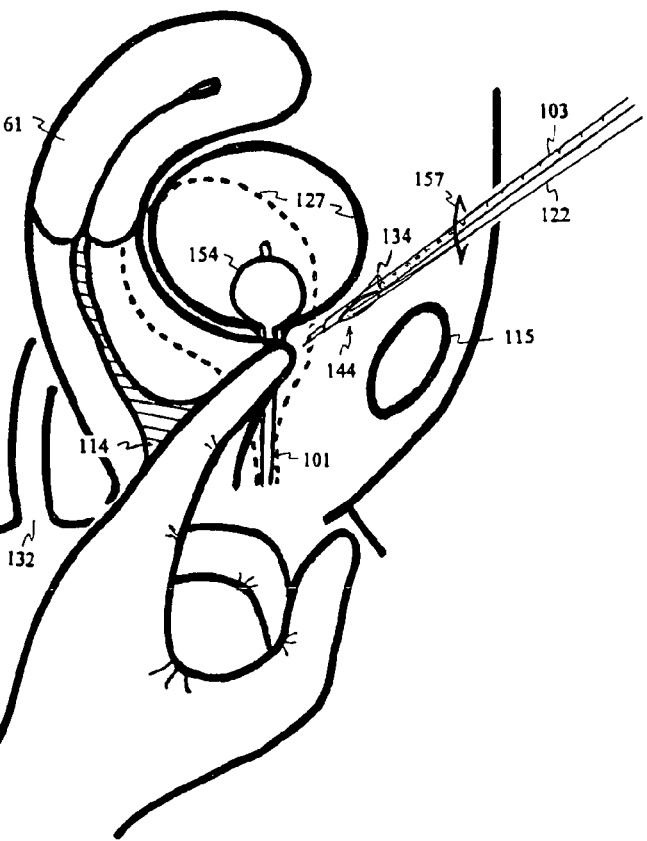
FIG. 20 shows a small incision 157 for inserting the stepped needle 103 with the suture anchor 144 into the vaginal wall.
Figure 21:
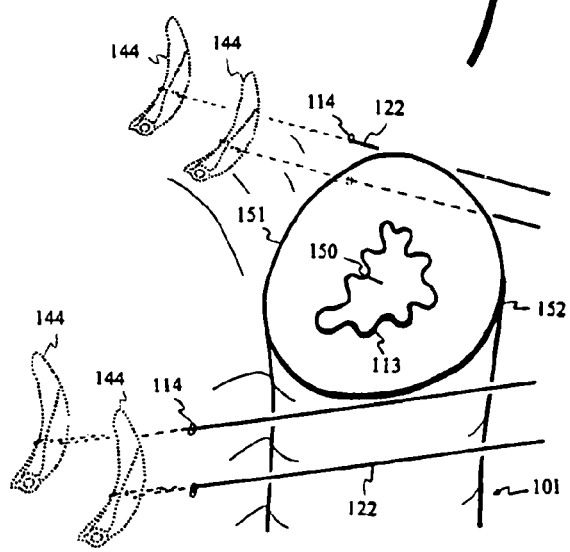
FIG. 21 depicts the urethral posterior wall 151 supported by sutures 122 and anchors 144 within the vagina 114.

Through a much smaller incision 157, the suture anchor 144 system can provide similar backboard support to the posterior wall 151 of the urethra 101. A catheter 154 is introduced through the urethra 101 into the bladder 127. The descended bladder 127, depicted in dotted lines, is lifted by the pressure against the wall of the vagina 144. Through the vagina 114, the surgeon can also feel the catheter 154 within the urethra 101 to guide the needle/anchor 103/144 insertion lateral to the urethra 101, as shown in FIG. 20, into the vaginal 114 wall. As the stepped needle 103 is withdrawn, the fin 134 hooks onto the vaginal 114 tissue, stripping the anchor 144 off the withdrawing needle 103. The method of guiding the needle 103 with the surgeon's finger is currently being used with the Stamey needle, a prior art device, for repairing stress urinary incontinence. Unlike the Stamey needle, the needle/anchor 103/144 system does not require passing the suture 122 back and forth from the vagina 114 cavity to the abdominal wall. Furthermore, the suture 122 introduced by the Stamey needle is exposed within the vagina, which increases the risk of infection. The suture anchor 144 on the other hand, can be deployed within the vaginal 114 wall, as partial thickness suturing in open surgery. The suture anchor 144 can also be delivered and deployed in the vaginal 114 cavity, as full thickness suturing. FIG. 21 depicts four suture anchors 144 fastened within the anterior vaginal 114 wall, providing backboard support to the posterior wall 151 of the urethra 101. The sutures 122 from the anchors 144 are knotted to fascia or ligament, similar to FIG. 17, but requiring only a much smaller incision 157. The orientation of the anchor 144 within tissue can be significant. For example, the anchors 144 deployed perpendicular to the urethra 101, as depicted in FIG. 21, may provide a more firm backboard support than the anchors 144 deployed parallel to the urethra 101.

Figure 22:
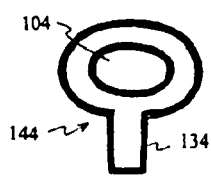
FIG. 22 indicates a proximal end of a suture anchor 144 with an elliptical lumen 104, sized and configured to fit over a stepped needle 103 with an elliptical cross-section.
Figure 23:
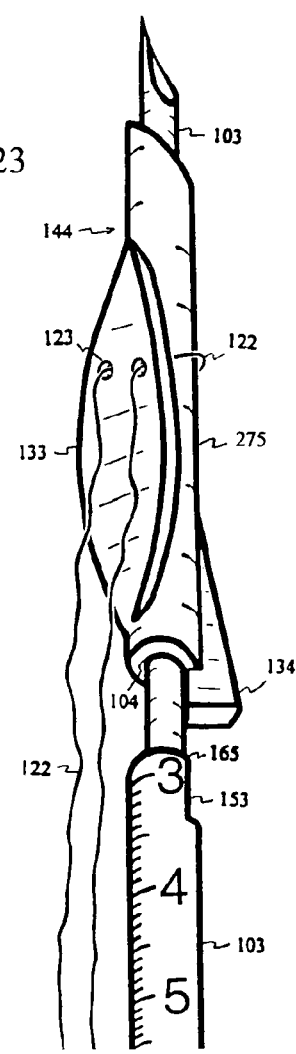
FIG. 23 shows a lengthened fin 134, sized and configured to fit into an indentation 153 on a stepped needle 103.

To prevent twisting between the anchor 144 and needle 103, the lumen 104 of the anchor 144 can be made non-round, elliptical for example, as shown in FIG. 22, with the stepped needle 103 sized and configured to fit the lumen 104. FIG. 23 shows an extended fin 134 sized and configured to fit into an indentation 153 on the stepped needle 103. Similarly, an extended portion from the stepped needle 103 can fit into an indentation in the anchor 144 to prevent the anchor 144 from spinning on the stepped needle 103.

Figure 24:
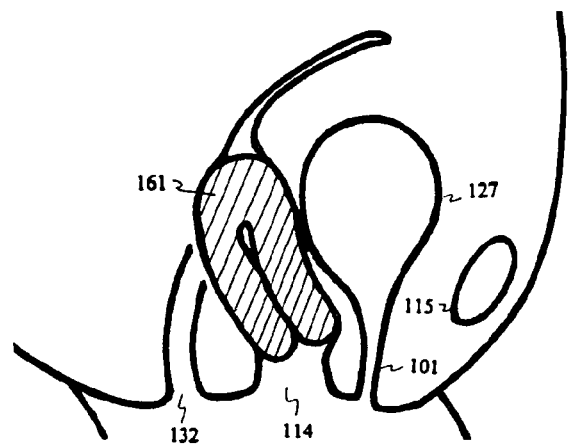
FIG. 24 depicts a uterine 161 prolapse.
Figure 25:
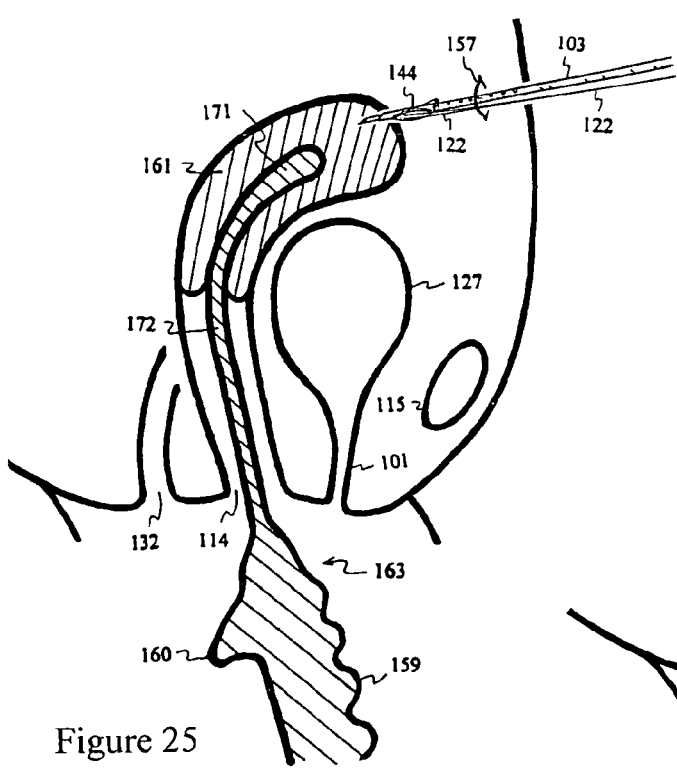
FIG. 25 depicts a repositioned uterus 161 pierced with the stepped needle 103 through a small incision 157.
Figure 26:
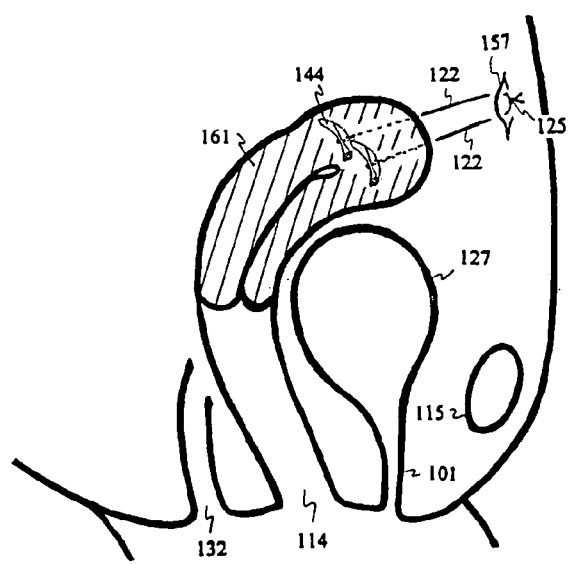
FIG. 26 depicts uterus 161 fastening with sutures 122 and anchors 144. The suture 122 is knotted 125 onto the ligament or fascia on the abdominal wall.

FIG. 24 depicts a patient with uterine 161 prolapse, a common problem in women. Uterine 161 prolapse is normally surgically treated with hysterectomy, removal of the uterus 161, either through vaginal or abdominal incision. The following procedure is ideally used in conjunction with the ligament-tightening procedure described in FIGS. 80 and 81. FIG. 25 depicts lifting and repositioning of the uterus 161 with a uterine tool 163 containing a blunt distal end 171, a shaft 172, a handle 159 and a lift 160. The stepped needle 103 with the suture anchor 144 is then inserted through a small incision 157, guided by an endoscope, into the repositioned uterus 161. As the stepped needle 103 is withdrawn, the fin 134 hooks onto the uterine 161 tissue, dislodging the anchor 144 from the withdrawn needle 103. The needle 103 and anchor 144 insertion procedure is repeated, and the sutures 122 are knotted 125 on the fascia or a ligament on the abdominal wall, as shown in FIG. 26, similar to the suture 122 tying for correcting urinary incontinence. Other supporting structures, such as the round ligament and broad ligament of the uterus, may also be suitable for fastening the suture 122 to and supporting the repositioned uterus 161.

Figure 27:
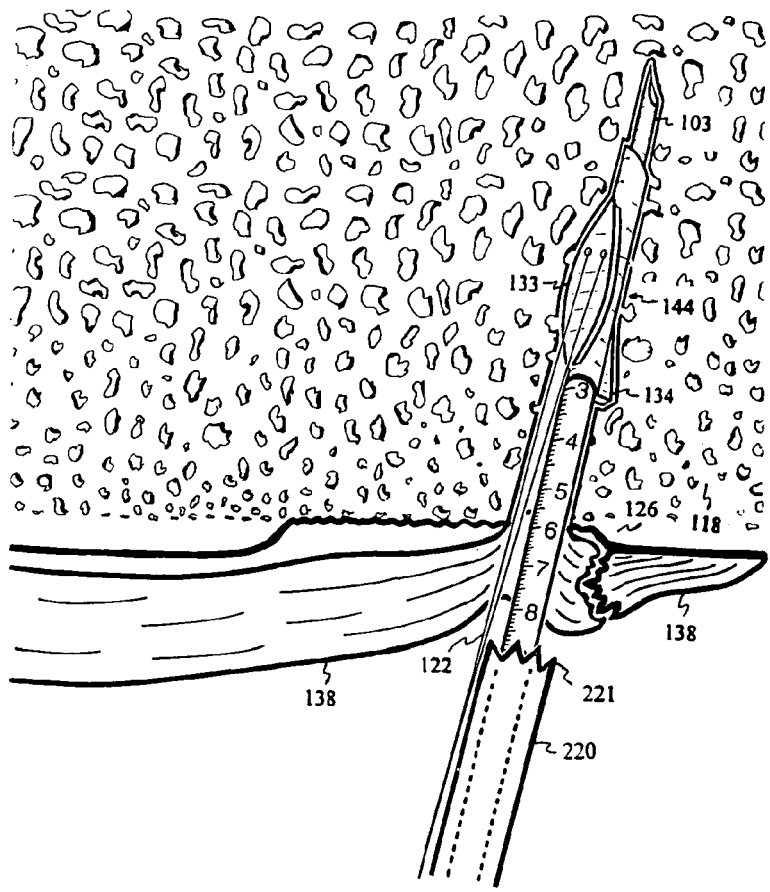
FIG. 27 depicts penetration of the stepped needle 103 with the suture anchor 144 through a torn ligament 138 into decorticated bone 118.
Figure 28:
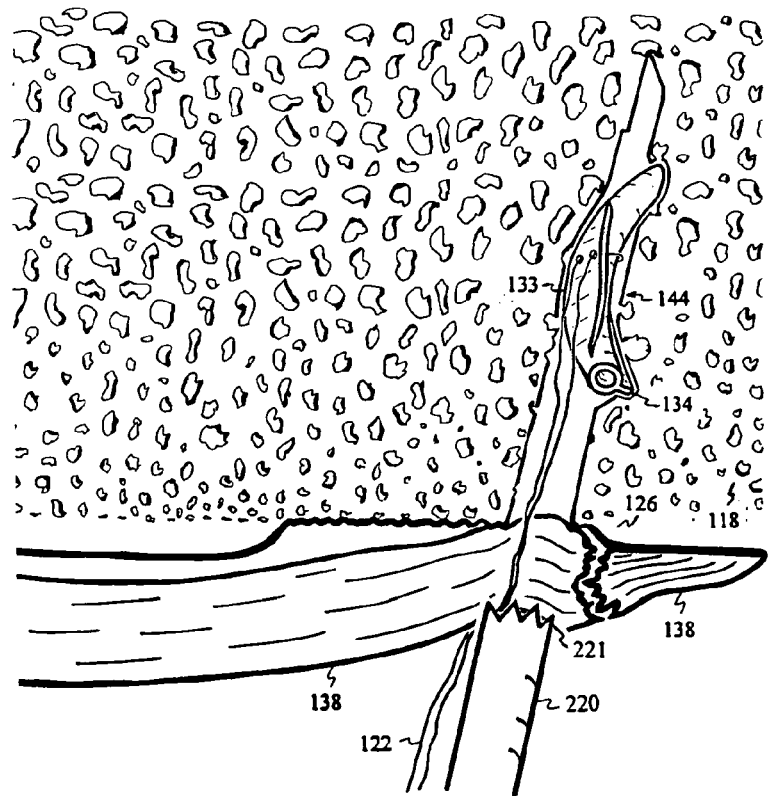
FIG. 28 depicts the suture anchor 144 resuming some of the curved configuration within the bone 118 after being dislodged from the withdrawn stepped needle 103.
Figure 29:
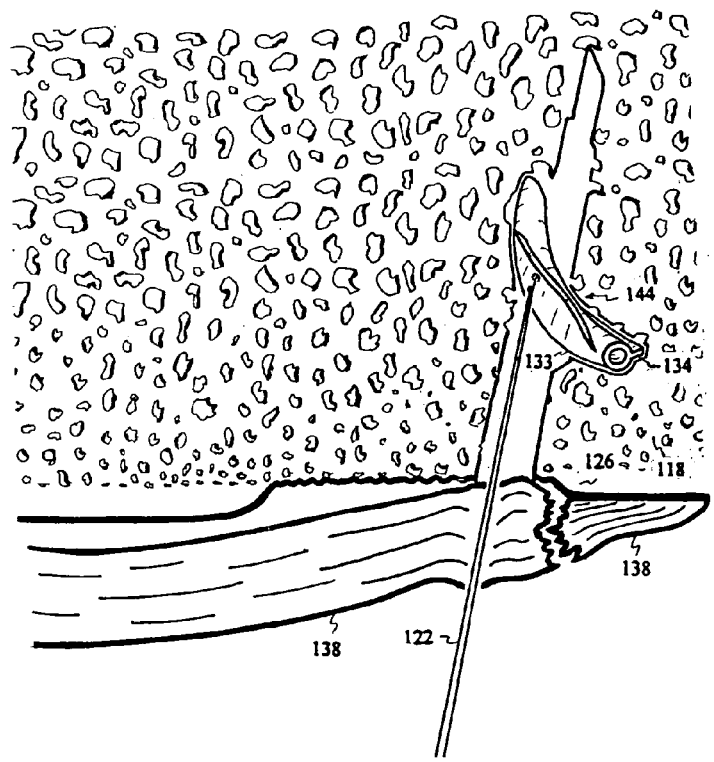
FIG. 29 depicts suture 122 tension driving the fin 134 further laterally into the bone 118.
Figure 30:
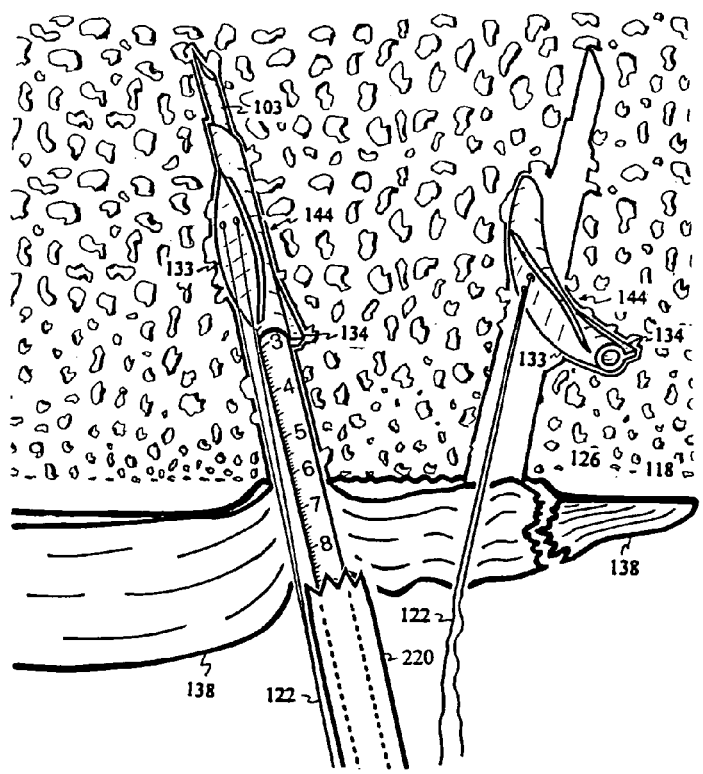
FIG. 30 depicts another anchor 114 delivered by the stepped needle 103 through the torn ligament 138 into cancellous bone 118.
Figure 31:
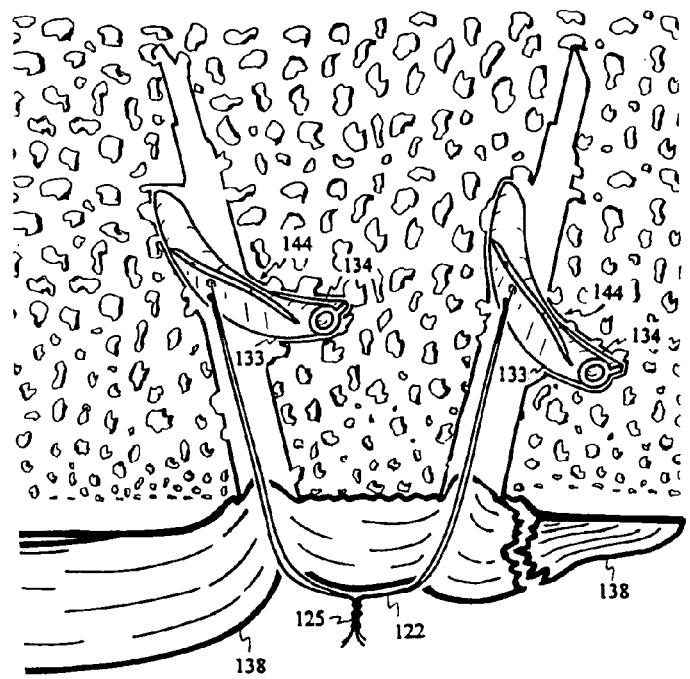
FIG. 31 depicts a suture knot 125 tied to fasten the torn ligament 138 onto the bone.

The suture anchor 144 can also be used in orthopaedic repairs. FIG. 27 depicts penetration of the stepped needle 103 and anchor 144 through a torn ligament 138 into freshly decorticated cancellous bone 118. The stepped needle 103 also contains a sleeve 220, freely sliding over the stepped needle 103. The position of the ligament 138 can be manipulated and maintained with grippers 221 on the distal end of the sleeve 220, as the stepped needle 103 is withdrawn. During needle 103 withdrawal, the fin 134 acts as a barb, hooking onto the cancellous bone 118, and stripping the anchor 144 off the withdrawing needle 103. FIG. 28 depicts curvature resumption of the suture anchor 144 within the porous cancellous bone 118 after having slid off the withdrawn stepped needle 103. FIG. 29 depicts tension applied to the suture 122, pulling on the curved anchor 144 and driving the fin 134 further laterally. The platform 133 of the anchor 144 provides a large surface area to press against the bone 118 and resist pull out. FIG. 30 depicts another anchor 114 delivered by the stepped needle 103 through the torn ligament 138 into the cancellous bone 118. The stepped needle 103 is then withdrawn with the second anchor 114 also fastened within bone 118. FIG. 31 depicts suture knot 125 tying to fasten the torn ligament 138 onto the bone. In arthroscopic surgery, slip knots 125 are most frequently tied and delivered to the surgical site with a knot 125 pushing device. The fastened ligament 138 will eventually heal and reattach onto the cancellous bone 118. In essence, the sutures 122 and anchors 114 are merely used to maintain the position of the torn ligament 138; reattachment and healing occur naturally with the surgically inflicted bleeding bone 118. Therefore, both the anchors 144 and sutures 122 can be made with biodegradable materials to prevent device migration with time.

Figure 32:
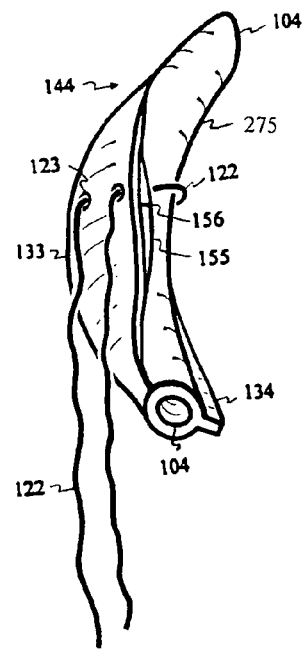
FIG. 32 shows a bend stop 155 with a closed gap 156 beneath the platform 133 to prevent excessive anchor 144 bending under significant suture 122 tension.
Figure 33:
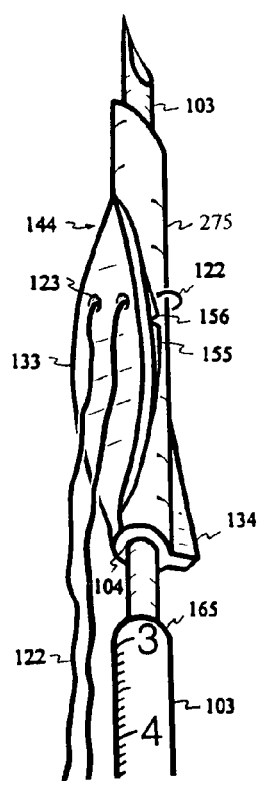
FIG. 33 shows a stepped needle 103 resiliently straightening the anchor 144 with the bend stop 155. In the straightened position, the gap 156 is open.
Figure 34:
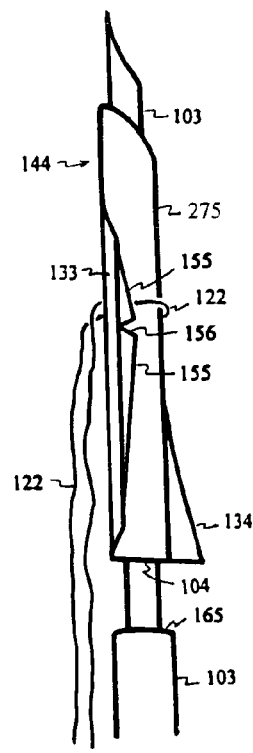
FIG. 34 depicts a side view of the straightened anchor 144 with an open gap 156 beneath the platform 133.
Figure 35:
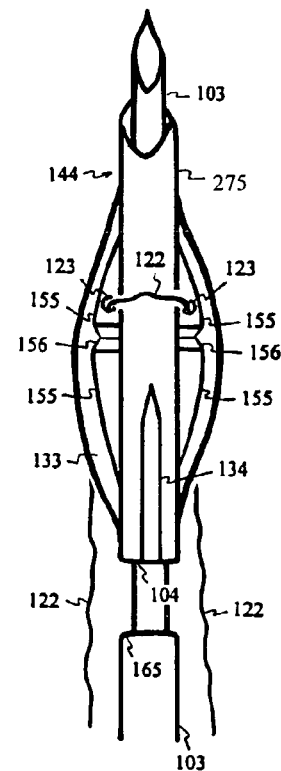
FIG. 35 indicates a bottom view of the straightened anchor 144 showing bend stops 155 with open gaps 156 beneath the platform 133.

The anchoring strength of the suture anchor 144 can be further improved. The anchor 144 reaches full anchoring strength as the anchor 144 forms almost a T-configuration or is perpendicular with the suture 122, as shown in FIG. 13. With excessive tension on the suture 122, the elastic anchor 144 may curve further, or even fold into a V-configuration. As a result, the anchoring strength would greatly decrease. To prevent the anchor 144 from excessive bending or folding, bend stops 155 can be added along both sides of the anchor 144 to increase rigidity and anchoring strength of the anchor 144. FIG. 32 depicts the bend stop 155 with a gap or V-groove 156 beneath the platform 133. When the suture anchor 144 is in the curved configuration, the gap 156 is closed to resist further bending of the anchor 144, as depicted in FIG. 32. As the elastic anchor 144 is resiliently straightened by the stepped needle 103, the gap 156 is opened, as shown in FIG. 33. FIG. 34 depicts the side view of the resiliently straightened anchor 144, showing the open gap 156 of the bend stop 155 beneath the platform 133. FIG. 35 depicts the bottom or belly view of the resiliently straightened anchor 144, showing the bilateral bend stops 155 and open gaps 156. The bend stops 155 are designed and positioned to limit or resist excessive anchor 144 bending to maximize anchoring strength.

A straight and rigid anchor 144 with the fin 134 can also rotate within tissue by utilizing the tension applied to the suture 122. As mentioned, the curvature of the anchor 144, as shown in FIG. 9, increases the distance, W, to provide additional torque for lateral rotation. For a rigid anchor 144, as shown in FIG. 36, a larger and more protruded fin 134 may adequately provide torque for the anchor 144 rotation within the tissue. FIG. 37 depicts the side view of the rigid anchor 144 showing a distance, $W_1$, measured from the proximal tip of the fin 134 to the suture opening 123. The distance, $W_1$, provides the initial rotational torque as tension is applied to the suture 122 by the surgeon. By elevating the suture openings 123 from a protrusion, a rigid anchor 144, shown in FIG. 38 with side view in FIG. 39, provides an even greater distance, $W_2$, for greater initial rotational torque. The fin 134 can be made pointed or angled, as shown in FIGS. 36 to 39 to facilitate lateral tissue penetration and anchor 144 rotation. Rotation of the anchor 144 within tissue is also favored when $L_1 > L_2$, where $L_1$ is the distance between the proximal tip of the fin 134 and the suture openings 123, and $L_2$ is the distance between the distal end of the anchor 144 and the suture openings 123. The tapered proximal ends, as shown in FIGS. 36 and 38, also help to facilitate lateral insertion into tissue during anchors 144 rotation.

Several derivatives may provide adequate anchoring strength for the suture 122. FIG. 40 depicts a suture attachment 164 without threading through the platform 133. For light duty suture 122 anchoring, the platform 133 may not be necessary. FIG. 41 shows an anchor 144 with the fin 134 but without a platform. FIG. 42 shows a curved anchor 144 without a fin. With a curvature built into the anchor 144, it may be sufficient to provide initial torque to rotate the anchor 144 within tissue when tension is applied to the suture 122.

Figure 43:
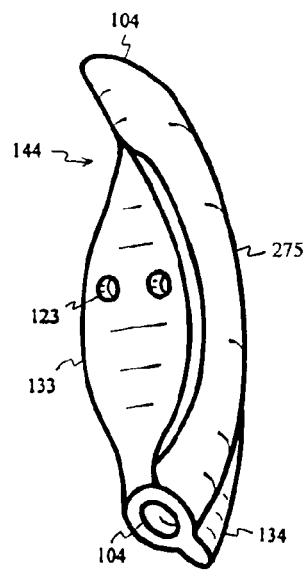
FIG. 43 depicts a curved suture anchor 144 with a platform 133 on the concave side of the curvature. The fin 134 is made blunt.
Figure 44:
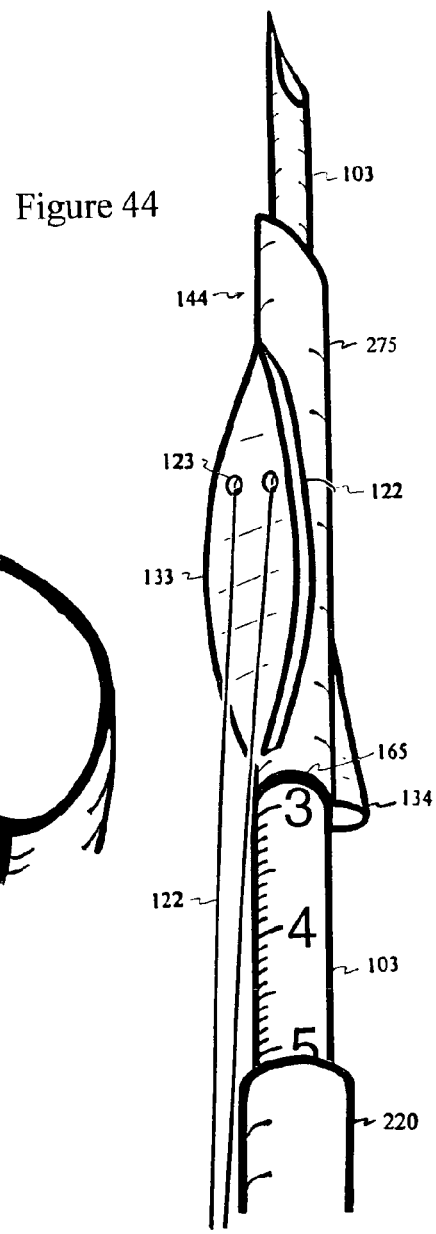
FIG. 44 shows the suture anchor 144 of FIG. 43 resiliently straightened by a needle 103 with a sliding sleeve 220.
Figure 45:
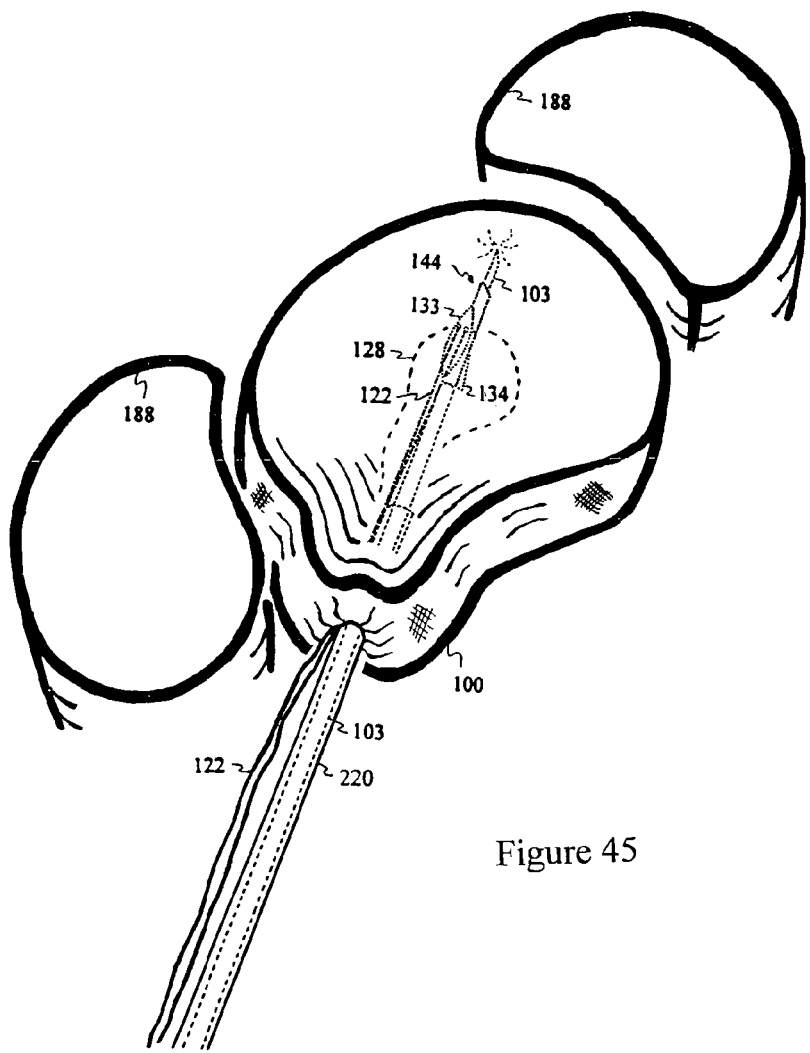
FIG. 45 depicts penetration of the stepped needle 103 with the sleeve 220 to deliver a suture anchor 144 through a bulging intervertebral disc 100.

The suture anchor 144 may also be used for full thickness anchoring. FIG. 43 depicts a curved suture anchor 144 with a platform 133 on the concave side of the curvature. The fin 134 is made blunt to avoid damage to adjacent tissue. The anchor 144 is loaded onto the stepped needle 103 with a sleeve 220 capable of sliding over the stepped needle 103, as shown in FIG. 44. The sleeve 220 is similar to that shown in FIG. 28 for holding and manipulating tissue. For full thickness suture 122 anchoring, the sleeve 220 can also be used to push the anchor 144 off the stepped needle 103 and deploy the anchor 144 outside the tissue. The protruded fin 134 can provide an additional function, as a contact point for the sleeve 220. FIG. 45 depicts a cross section of a bulging L4-5 intervertebral disc 100 located between psoas major muscles 188. Under fluoroscopic guidance or other means, the stepped needle 103 carrying the anchor 144, as shown in FIG. 44, is delivered through a small posteriolateral incision, into the bulging annulus and nucleus pulposus 128, as shown in FIG. 45. The advancement of the stepped needle 103 stops as the distal tip of the stepped needle 103 exits the disc 100. The sliding sleeve 220 is used to push and expel the anchor 144 with the attached suture 122 out of the disc 100. Especially with a radiopaque coating on the anchor 144, it is possible to see the orientation of the anchor 144. When tension is applied to the suture 122, the platform 133 of the anchor 144 is likely to conform and press against the outer surface of the disc 100, as shown in FIG. 46. Otherwise, the orientation of the anchor 144 can be corrected by advancing the distal tip of the sleeve 220 to manipulate the anchor 144 and pull on the suture 122 until the suture anchor 144 is properly positioned. Both the stepped needle 103 and sleeve 220 are withdrawn after proper deployment of the anchor 144.

FIG. 47 depicts a curved disc compressor 111 with two openings 123 for the suture 122 and a round or blunt annular compressing region 119. FIG. 48 depicts knot 125 tying and bulge compression of the fastened disc compressor 111. The suture 122 is secured with full thickness anchoring by the anchor 144 and compressor 111. The bulge is compressed and fastened to alleviate pain from nerve impingement.

Figure 49:
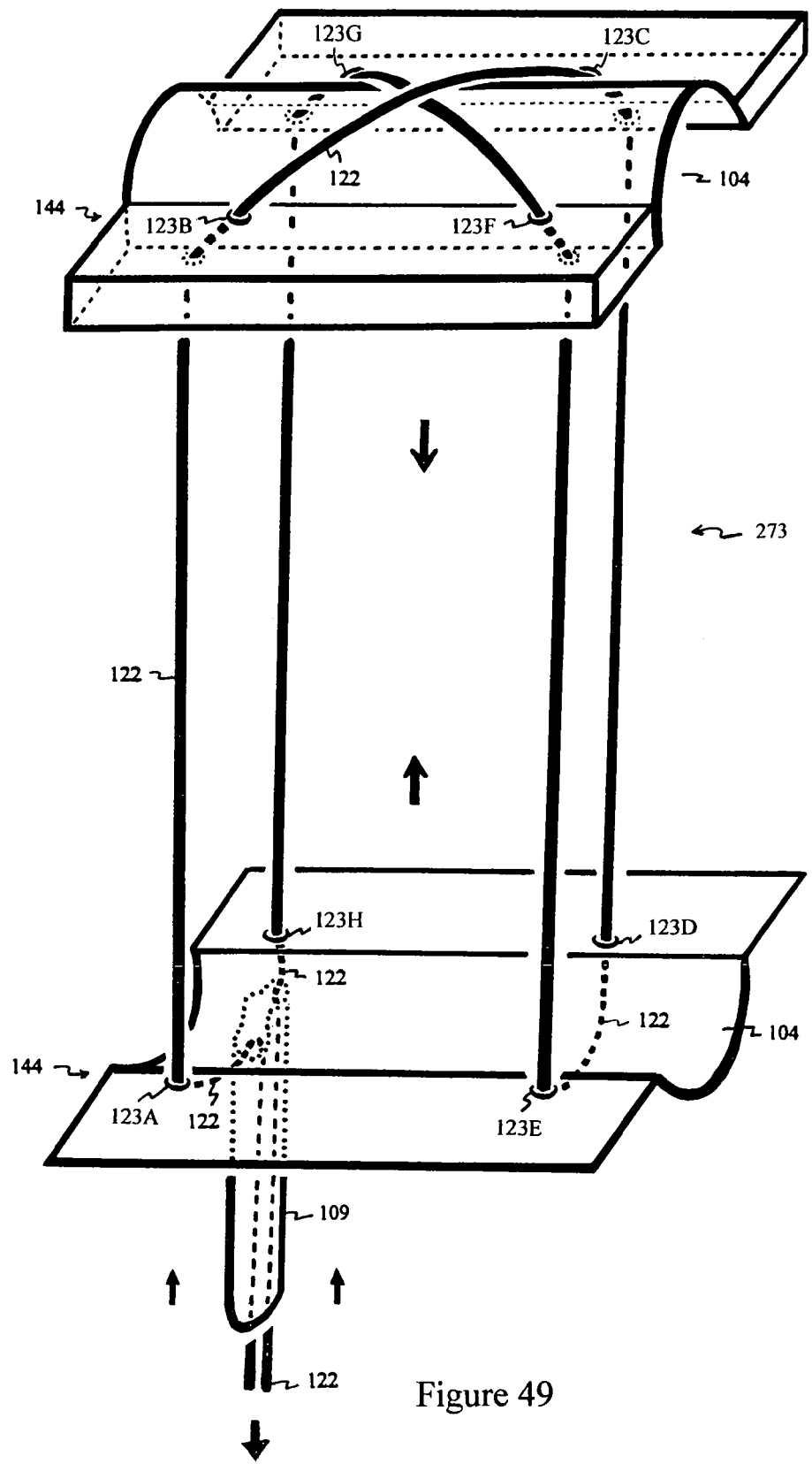
FIG. 49 depicts portions of two anchors 144 connected by a suture 122 to form an approximating device 273 for tightening or shortening tissue.

Two suture anchors 144 with unique suture 122 arrangement between them can be loaded in series on a stepped needle 103 to be deployed within tissue. As the suture 122 is pulled by the surgeon, the anchors 144 draw close to each other, pulling in or approximating the inserted tissue. FIG. 49 depicts portions of two anchors 144 connected by a suture 122 through holes 123A, 123B, 123C, 123D, 123E, 123F, 123G then 123H. Proximal ends of the suture 122 are threaded through a plunger 109. The holes 123B, 123C, 123F and 123G are angled to facilitate sliding of the suture 122 after anchor 144 rotation. The suture 122 between the holes 123D and 123E forms a stationary loop beneath the proximal anchor 144. As the suture 122 is being pulled and the plunger 109 is being pushed against the proximal anchor 144, the strands of suture 122 will slide from 123F to 123G and from 123C to 123B. With the stationary loop beneath the proximal anchor 144, the anchors 144 will draw close to each other to approximate, compress or plicate (fold) the inserted tissue. The distal and proximal suture anchors 144 with the suture 122 form an approximating device 273 designed for minimally invasive use.

Two resiliently straightened anchors 144 are loaded in series on a double-stepped 165 needle 103, as indicated in FIG. 50. Similar to FIG. 49, the suture 122 is threaded through holes 123A, 123B, 123C, 123D, 123E, 123F, 123G then 123H. For clarification, the suture 122 from holes 123A to 123D is white and from holes 123E to 123H is black. Both white and black sutures 122 are slack to clarify points of origin. The distal end of the proximal anchor 144 is tapered for lateral tissue penetration. The lumen 104 of the distal anchor 144 is smaller than the lumen 104 of the proximal anchor 144, each corresponding to the sizes of the distal and proximal steps 165 of the needle 103. The distance between the steps 165 can be pre-set or fixed to deliver the anchors 144.

As the fins 134 of the distal and proximal anchors 144 snag into tissue, the needle 103 is withdrawn to deposit both anchors 144 with the connecting suture 122, as shown in FIG. 51. Both anchors 144 resume their curved configuration. In vertical or insertion position, the angled suture holes 123B and 123G of the distal anchor 144 are designed to resist suture 122 sliding and to favor pivoting of the distal anchor 144, as shown in FIG. 52. The rotation of the distal anchor 144 creates tension on the suture 122 connecting holes 123C to 123D and 123F to 123E, as shown in FIGS. 49 and 53. The tension of the sutures 122 lifts the proximal anchor 144 by the loop beneath holes 123D to 123E, as shown in FIGS. 53 and 49. As a result, the proximal anchor 144 also rotates, laterally pressing the pointed distal end into the tissue, with the fin 134 behaving like a rudder to direct rotation.

Figure 54:
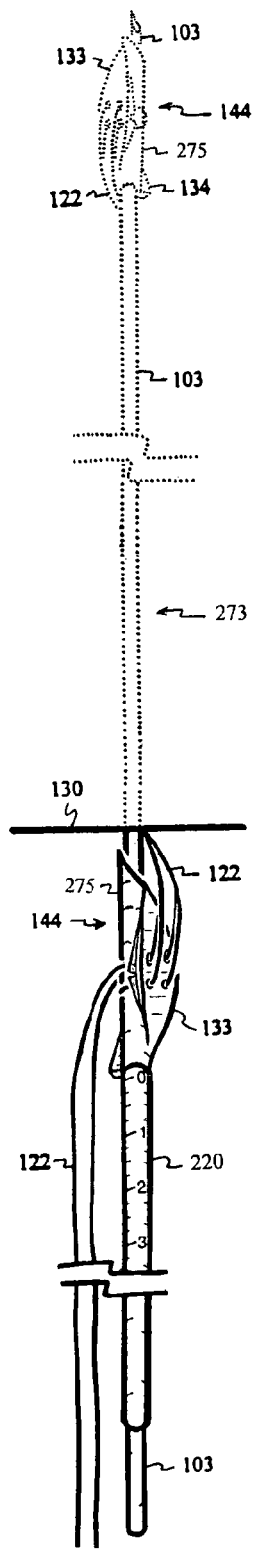
FIG. 54 shows anchor 144 insertion into tissue 130 with the needle 103, as the initial step for deploying the approximating device 273.
Figure 55:
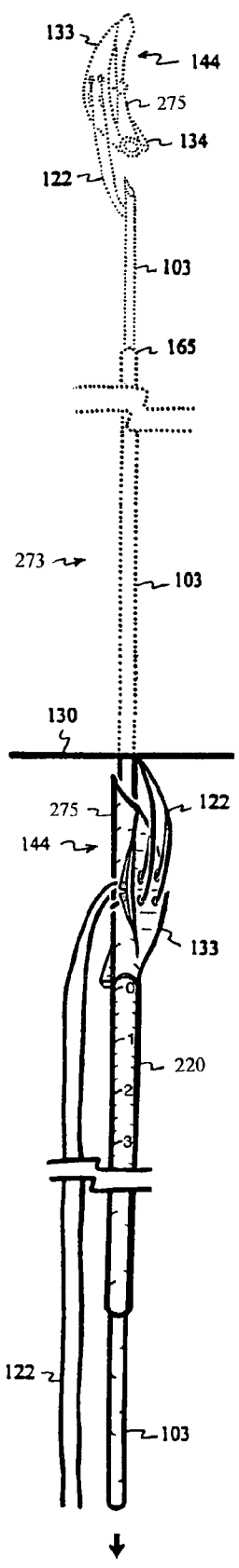
FIG. 55 indicates partial withdrawal of the needle 103 to deploy the distal anchor 144 within tissue 130.

The proximal anchor 144 can also be inserted by a sliding sleeve 220, rather than by the stationary second step 165 of the needle 103. FIG. 54 shows a stepped needle 103 insertion to deliver the distal anchor 144 into the tissue 130. As the tissue 130 is snagged by the fin 134, partial withdrawal of the needle 103 deposits the distal anchor 144 within tissue 130, as indicated in FIG. 55. The proximal anchor 144 is delivered by pushing the sleeve 220 and pulling the suture 122, as shown in FIG. 56. Suture 122 pulling also initiates pivoting of the distal anchor 144. FIG. 57 shows complete insertion of the proximal anchor 144 into the tissue 130. The needle 103 is then withdrawn to deposit the proximal anchor 144, as shown in FIG. 58, to complete the installation of the approximating device 273.

Figure 59:
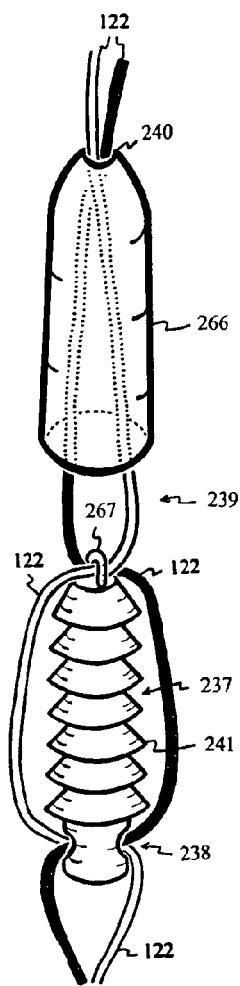
FIG. 59 depicts composition of a suture lock 239 with sutures 122 passing through a cone 266 over a one-way grip 237 with individual grippers 241.
Figure 60:
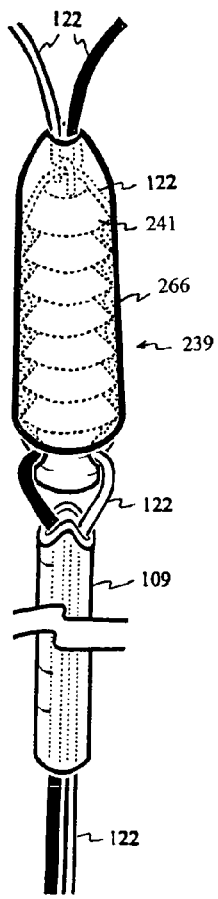
FIG. 60 shows the lock 239 assembly with the suture 122 fastened between the cone 266 and grippers 241. A plunger 109 is used to advance the suture lock 239.
Figure 61:
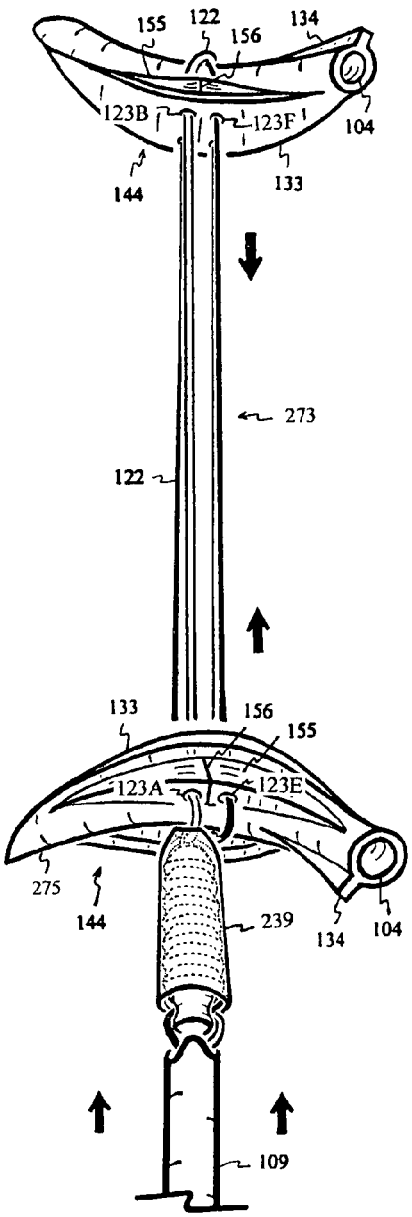
FIG. 61 indicates pulling on the sutures 122 and pushing on the plunger 109 against and lock 239 to draw the anchors 144 together as an approximating device 273 within tissue.
Figure 61:
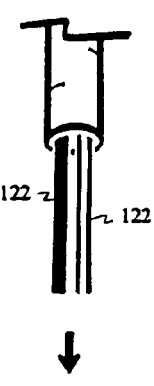
Figure 62:
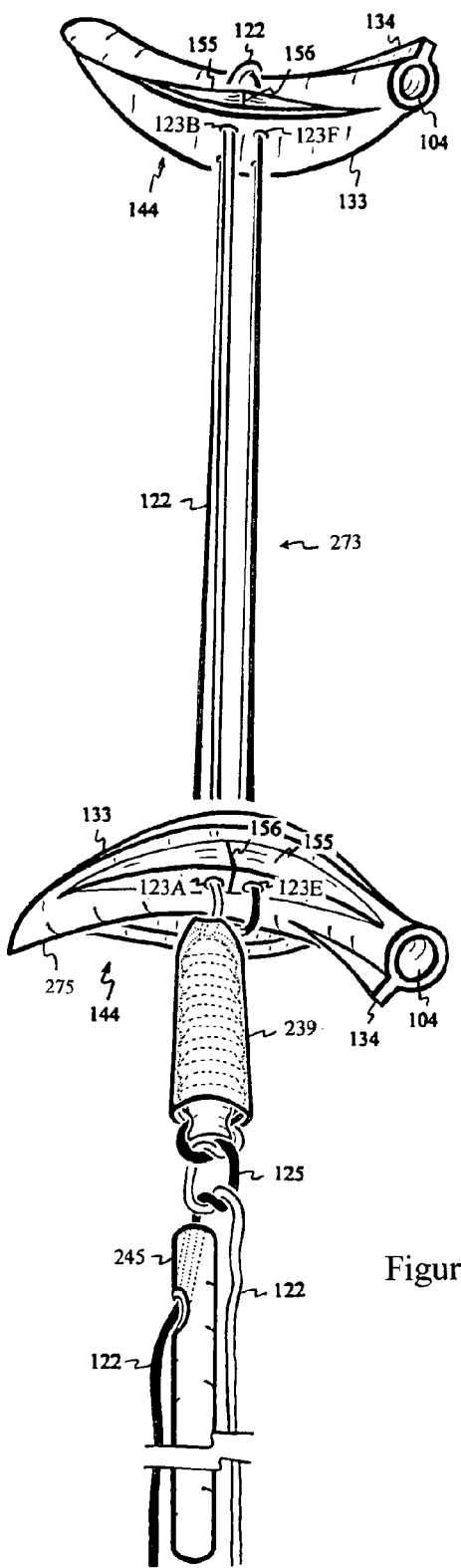
FIG. 62 depicts knot 125 tying within tissue using a knot pusher 245.

The approximating device 273 can be tightened and maintained under tension. A one-way suture lock 239 prevents backsliding during tying and allows further tightening of the suture 122 to fasten the approximating device 273. FIG. 59 depicts the composition of a suture lock 239 with a pair of sutures 122 passing through a hole 240 of a cone 266 into a loop 267 of an one-way grip 237 with individual grippers 241, then threaded through a passage 238 at the proximal end of the grip 237. The suture 122 passed through the loop 267 helps to direct the one-way grip 237 into the cone 266. The passage 238 of the grip 237 provides a foundation for suture knot 125 tying. The loop 267 and passage 238 also keep the pair of sutures 122 apart to obtain maximum locking strength within the cone 266. The cylindrical grippers 241 are arranged in angle, layers, sized and configured to fit within the cone 266. Each layer of the grippers 241 are tapered, narrow at the top and widened at the base, biased against backsliding of the suture 122 but allowing further suture 122 tightening. FIG. 60 shows the lock 239 assembly with the pair of sutures 122 fastened between the cone 266 and biased grippers 241. The pair of sutures 122 is inserted into a plunger 109. The plunger 109 is bilaterally tapered at the distal end, as shown in FIG. 60, for pushing against the proximal end of the one-way grip 237 without interfering with the pulling of the suture 122 to tighten the approximating device, as shown in FIG. 61. As an optional procedure, slipknots 125 can be tied then delivered by a knot pusher 245 onto the proximal end of the one-way grip 237, as shown in FIG. 62.

Figure 63:
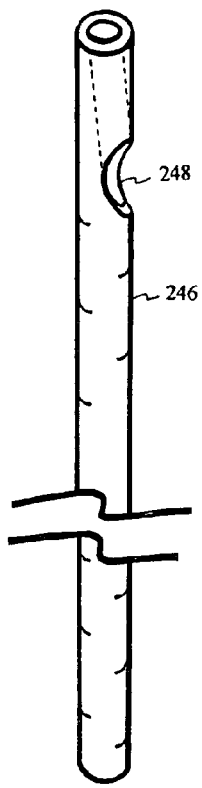
FIG. 63 shows an inner tube 246 containing a channel opening from the distal end to a side window 248.
Figure 64:
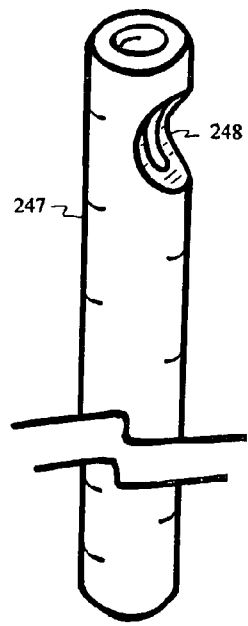
FIG. 64 shows an outer tube 247 also containing a channel opening from the distal end to a side window 248.
Figure 65:
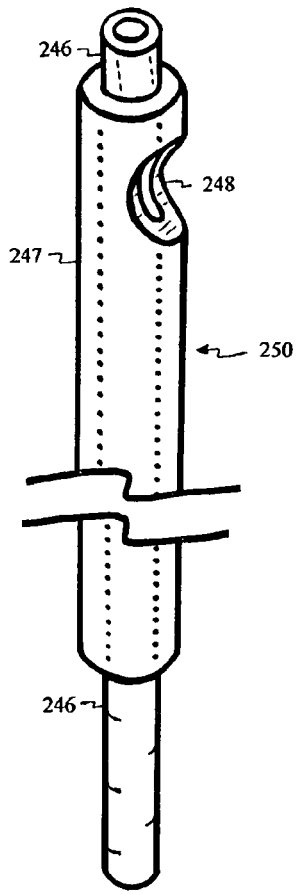
FIG. 65 depicts a suture cutter 250 assembled by fitting the inner tube 246 into the outer tube 247 with overlapping side windows 248.
Figure 66:
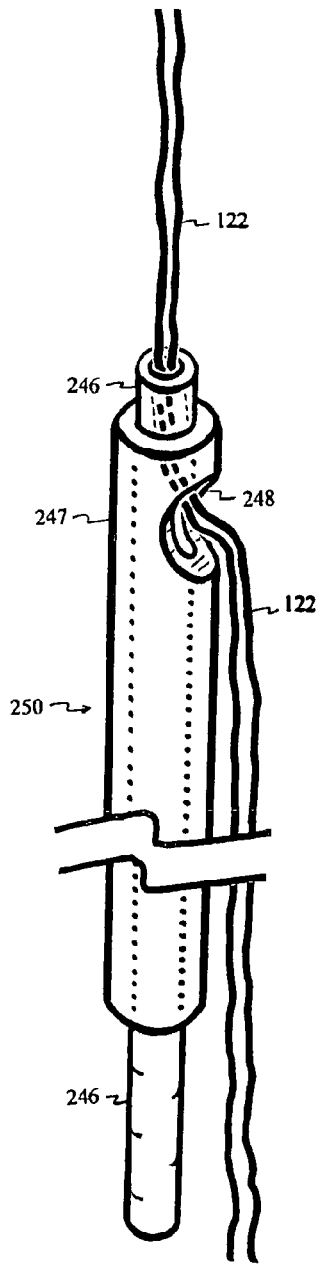
FIG. 66 indicates threading a pair of sutures 122 through the distal opening, out the overlapping side windows 248 of the inner tube 246 and outer 247 tube.
Figure 67:
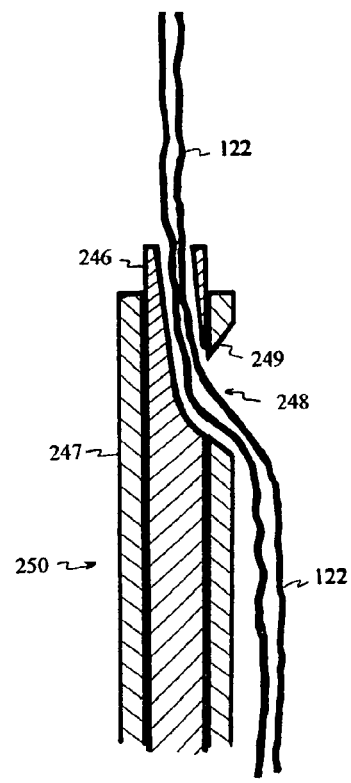
FIG. 67 shows a mid-longitudinal view of the suture cutter 250 with sharp edges 249 at the side windows 248.
Figure 68:
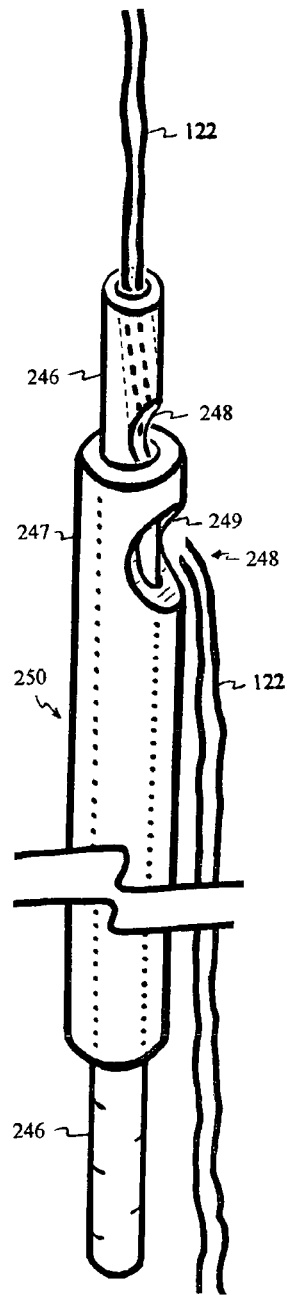
FIG. 68 depicts cutting of the suture 122 by the sharp edges 249 as the outer tube 247 slides over the inner tube 246.
Figure 69:
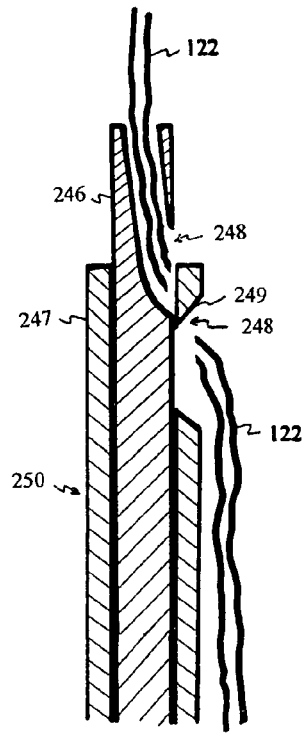
FIG. 69 shows a mid-longitudinal view of FIG. 68.
Figure 70:
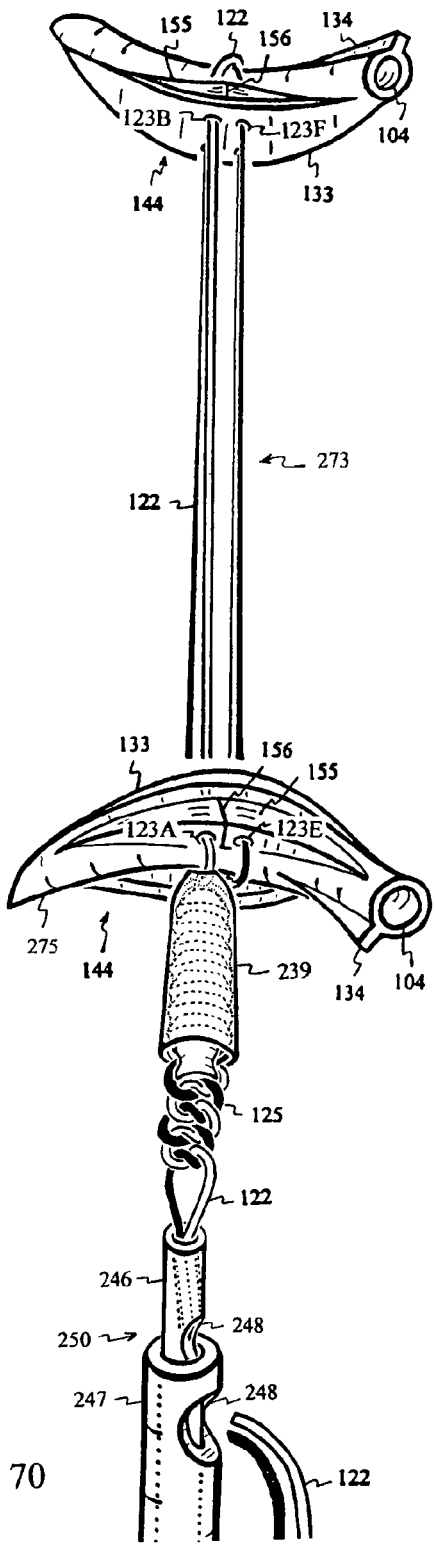
FIG. 70 depicts suture 122 cutting with the cutter 250 after knots 125 are tied.

Cutting the excess suture 122 beneath the tissue helps to conceal the entire approximating device 273, which may be advantageous since exposure of the non-degradable suture 122 can promote infection. A suture 122 cutting device 250 contains an inner tube 246 and outer tube 247. FIG. 63 shows a channel open from the distal end of the inner tube 246 to a side window 248 of the suture cutter 250. FIG. 64 shows the outer tube 247 also containing a side window 248. The inner tube 246 is tightly fitted inside the outer tube 247 with overlapping side windows 248, as shown in FIG. 65, to form the suture cutter 250. The suture cutter 250 is a relatively thin tubular device. The excess suture 122 is threaded through the distal opening and out the overlapping side windows 248 of the inner tube 246 and outer tube 247, as shown in FIG. 66. By straightening and holding onto the proximal ends of the excess suture 122, the cutter 250 can slide along the suture 122 into tissue through the entry punctured by needle 103 and anchors 144. FIG. 67 shows a mid-longitudinal view of the suture cutter 250 with sharp edges 249 at the side windows 248. As the outer tube 247 slides against the inner tube 246 or vice versa, the sharp edges 249 behave like scissors, cutting the sutures 122 extending out of the side windows 248, as shown in FIG. 68. FIG. 69 shows a mid-longitudinal view of suture 122 cutting by sliding the outer 247 and inner tube 246 against each other. FIG. 70 depicts suture 122 cutting with the device 250 after knot 125 tying. The cutter 250 is then withdrawn from tissue. As a result, all components are concealed within the tissue to complete the installation of the minimally invasive approximating device.

Figure 71:
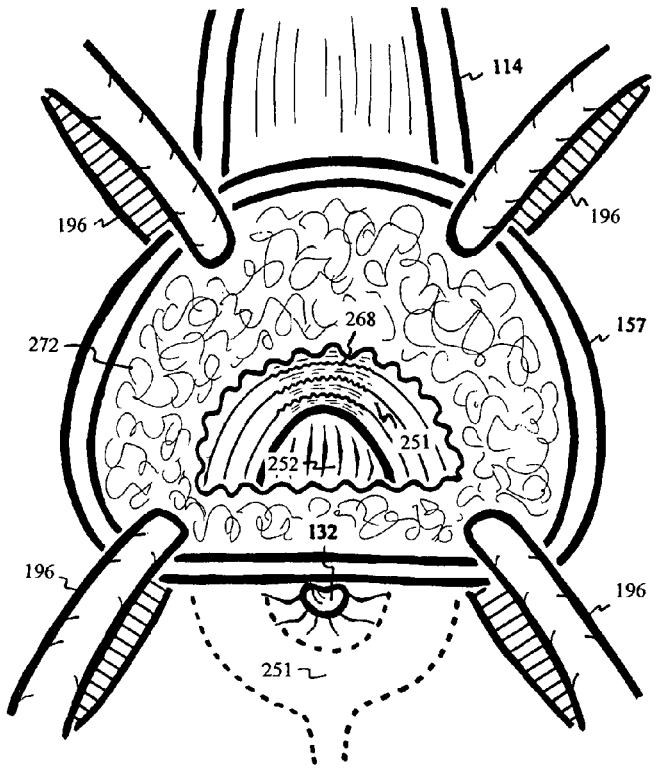
FIG. 71 indicates retraction of an incision 157 to expose a scarred 268 external sphincter 251, a common cause of anal incontinence.
Figure 72:
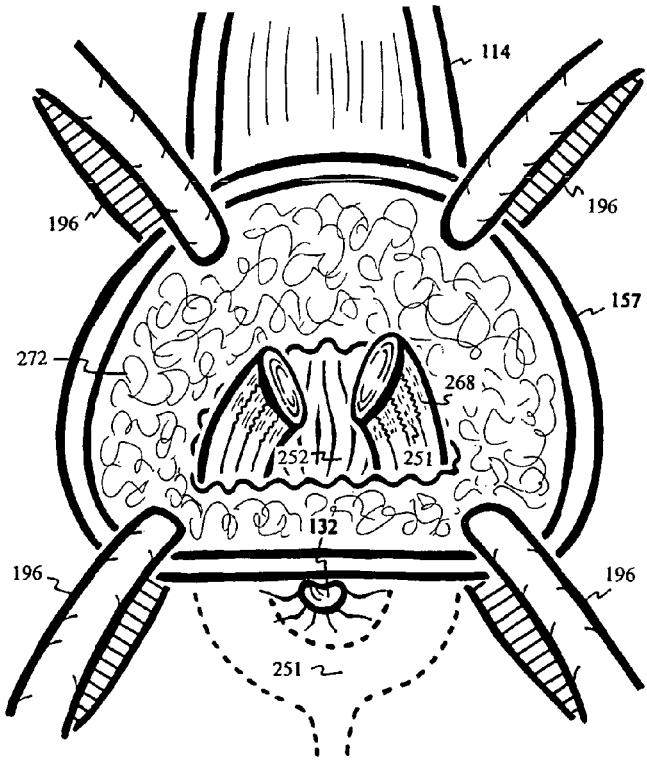
FIG. 72 shows cutting of the sphincter 251 in a prior art surgical procedure.
Figure 73:
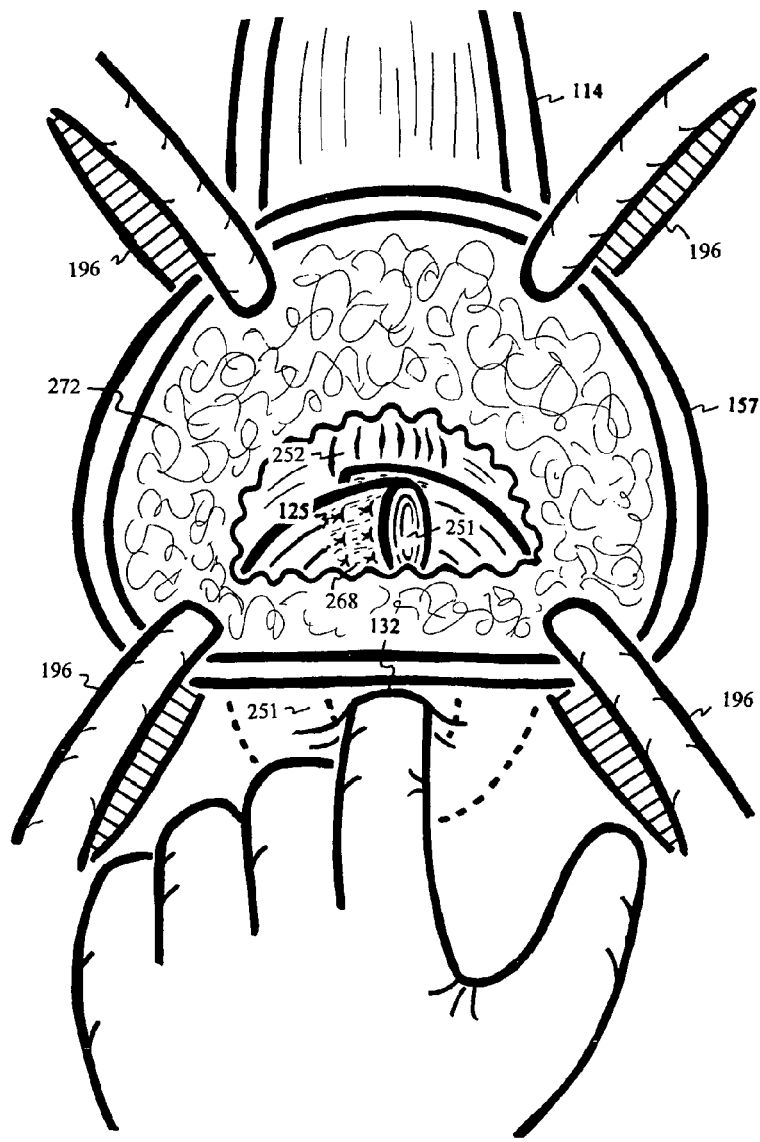
FIG. 73 depicts overlapping and suturing the external sphincter 251 to tighten the internal sphincteric muscle 252.

One of the most common causes of anal incontinence is scarring of the external sphincter from childbirth. The scarred tissue 268 of the external sphincter 251 can be revealed beneath adipose tissue 272 with retractors 196 opening a semi-circular incision between the vagina 114 and the rectum 132, as shown in FIG. 71. Currently, the scarred sphincter 251 is cut, as shown in FIG. 72. Then the scarred tissue 268 is overlapped, sutured and knotted 125 to tighten around the internal sphincter 252 beneath, as indicated in FIG. 73. The tightness of the sphincteric repair is judged by the feel of the surgeon's finger. After surgical repair of the sphincter 251, painful defecation is inevitable. Infection is also common.

Figure 74:
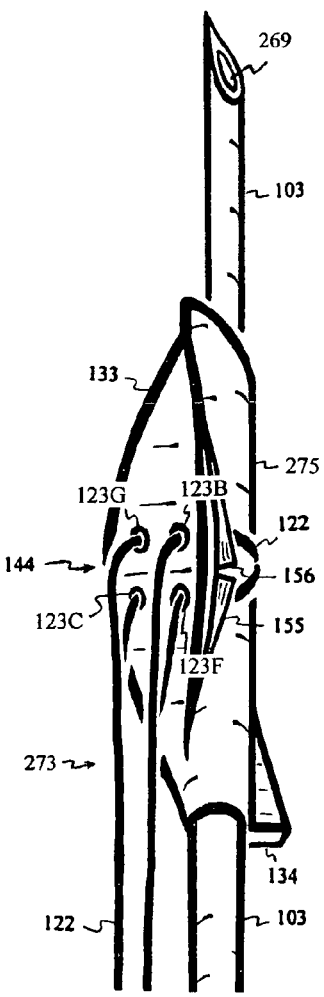
FIG. 74 shows a lumen 269 in the needle 103 for delivering radiopaque, echogenic or other tracing agent to guide needle 103 insertion.

Sphincter 251 repair can be minimally invasive using the approximating devices 273. To guide the needle 103 into the proper location, radiopaque, echogenic or other tracing agents can be injected through a lumen 269, as shown in FIG. 74, as the needle 103 advances into the body. Within the loosely packed adipose tissue 272, the injected tracing agent is likely to diffuse quickly. However, within highly structured and relatively dense tissue, such as muscle, tendon, ligament or organ, diffusion of the tracing agent is limited, so it might be possible to indicate the shape of the tissue, an important criterion for verifying the target site for suture 122 anchoring.

Figure 75:
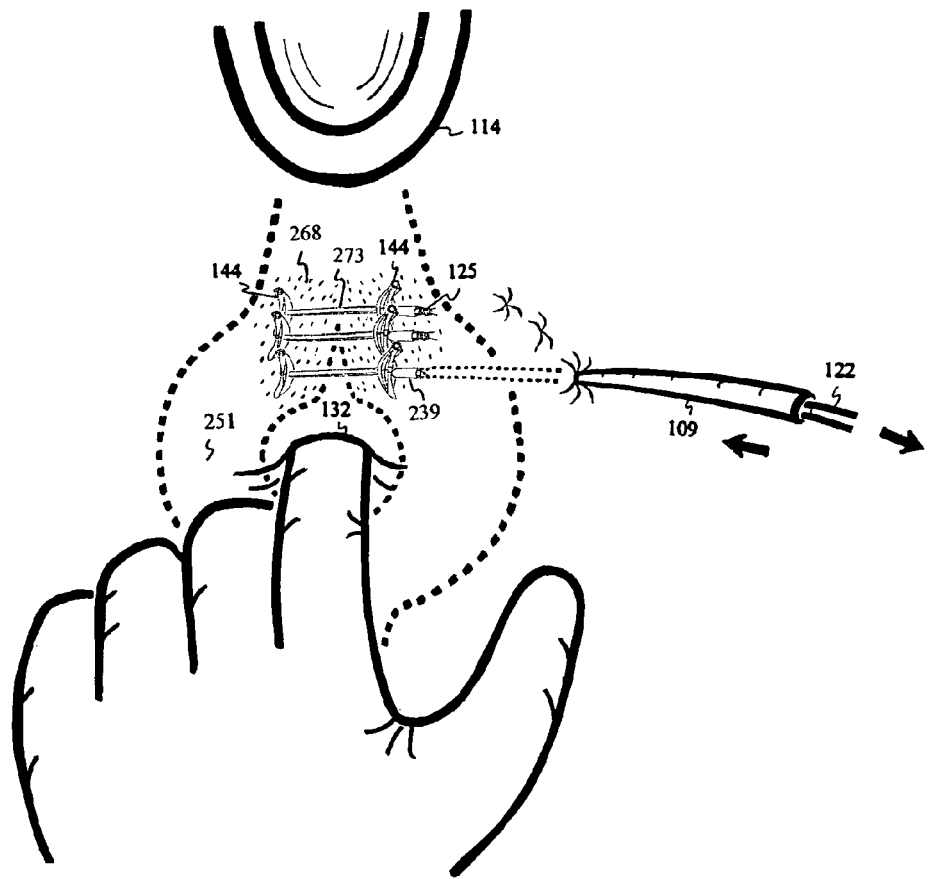
FIG. 75 shows tightening of the scarred 268 external sphincter 251 with multiple approximating devices 273.

The muscular external sphincter 251 encircles the rectum 132 beneath the adipose tissue 272, as shown in FIGS. 71 and 75. With guidance, the needle 103 is laterally inserted between the vagina 114 and rectum 132 to bridge both sides of the loose external sphincter 251. The needle 103 can be made with a slight curvature for puncturing through skin and adipose tissue 272, then into both sides of the loose sphincter 251. The anchors 144 can be inserted with the procedures similar to FIGS. 54 to 58, positioning the pair of anchors 144 into opposite sides of the loose sphincter 251. FIG. 75 depicts tightening of the external sphincter 251 by pulling the suture 122 and pushing the plunger 109 against the proximal end of the suture lock 239 at the same time, as shown in FIG. 61. As a result, the approximating device 273 restricts and narrows the circular external sphincter 251 by taking up the scarred 268 and loose tissue, as shown in FIG. 75. The sutures 122 can then be knotted 125 and cut beneath the skin, as shown in FIGS. 62, 70 and 75. The suture 122, anchors 144 and lock 239 can be made with biodegradable materials. Oozing from the sphincteric 251 muscle traumatized by insertions of needles 103 and suture anchors 144 can initiate permanent tissue adhesion, holding and keeping the sphincter 251 in the approximated position even after degradation of the suture 122 and the anchors 144.

Figure 76:
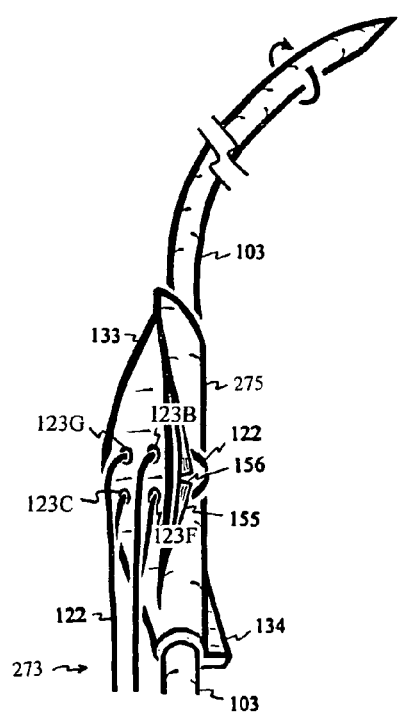
FIG. 76 depicts a flexible needle 103 with a tapered tip, as a sewing needle, for delivering the approximating device 273.
Figure 77:
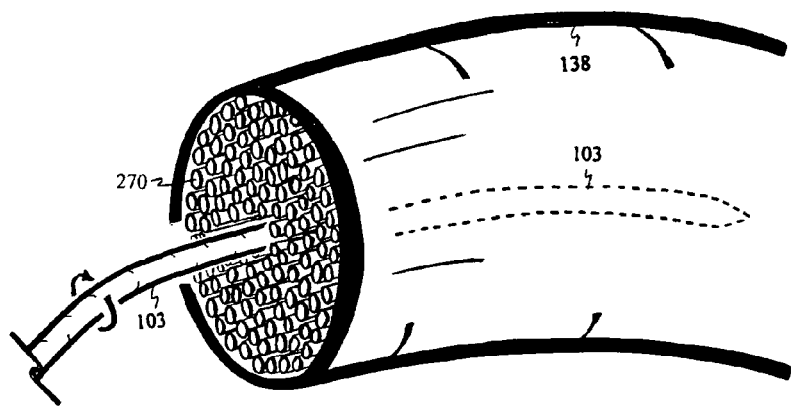
FIG. 77 depicts rotational advancement of the flexible needle 103 between collagen bundles 270 of tendon or ligament 138.
Figure 78:
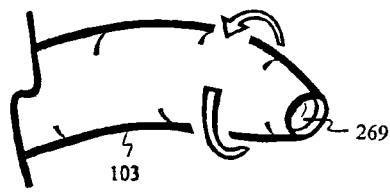
FIG. 78 depicts a lumen 269 in the rotational needle 103 for delivering radiopaque, echogenic or other tracing agent to guide needle 103 insertion.

The tips of most surgical needles are designed to cut as well as puncture into tissue. On the other hand, for delivering the approximating device 273 along a slender tissue, a tip without cutting edges, similar to a sewing needle shown in FIG. 76, is preferred. The tip with non-cutting edges is more likely to advance within a tissue with longitudinally oriented fibers, especially accompany with rotation during advancement. The slender tissue can be a tendon or a ligament with collagen bundles 270 formed lengthwise along the tissue. FIG. 77 depicts the needle 103 with non-cutting edges being advanced along a ligament 138 using rotational motion to drill and split a path between collagen bundles 270. The needle 103 can also be made with flexible or shape memory material, such as nickel-titanium alloy, to conform within the tendon or ligament 138. When the appropriate depth of the needle 103 is reached, both the distal and proximal anchors 144 can then be individually delivered with sleeves 220. To guide the rotational needle 103 into tissue, radiopaque, echogenic or other tracing agents can also be injected through a lumen 269, as shown in FIG. 78.

Figure 79:
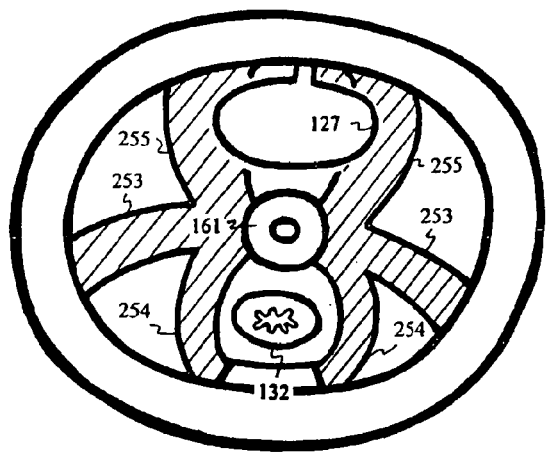
FIG. 79 indicates a cross-sectional view of the uterine 161 supportive structure, cardinal 253 and sacrouterine 254 ligaments, and fascia 255.

Uterine prolapse is commonly caused by sagging ligaments. The current treatment is hysterectomy. FIG. 79 indicates a cross-sectional view of uterine 161 supports. The cardinal ligament 253 provides for lateral support, sacrouterine ligament 254 for posterior support and fascia 255 for anterior support to the uterus 161.

Figure 80:
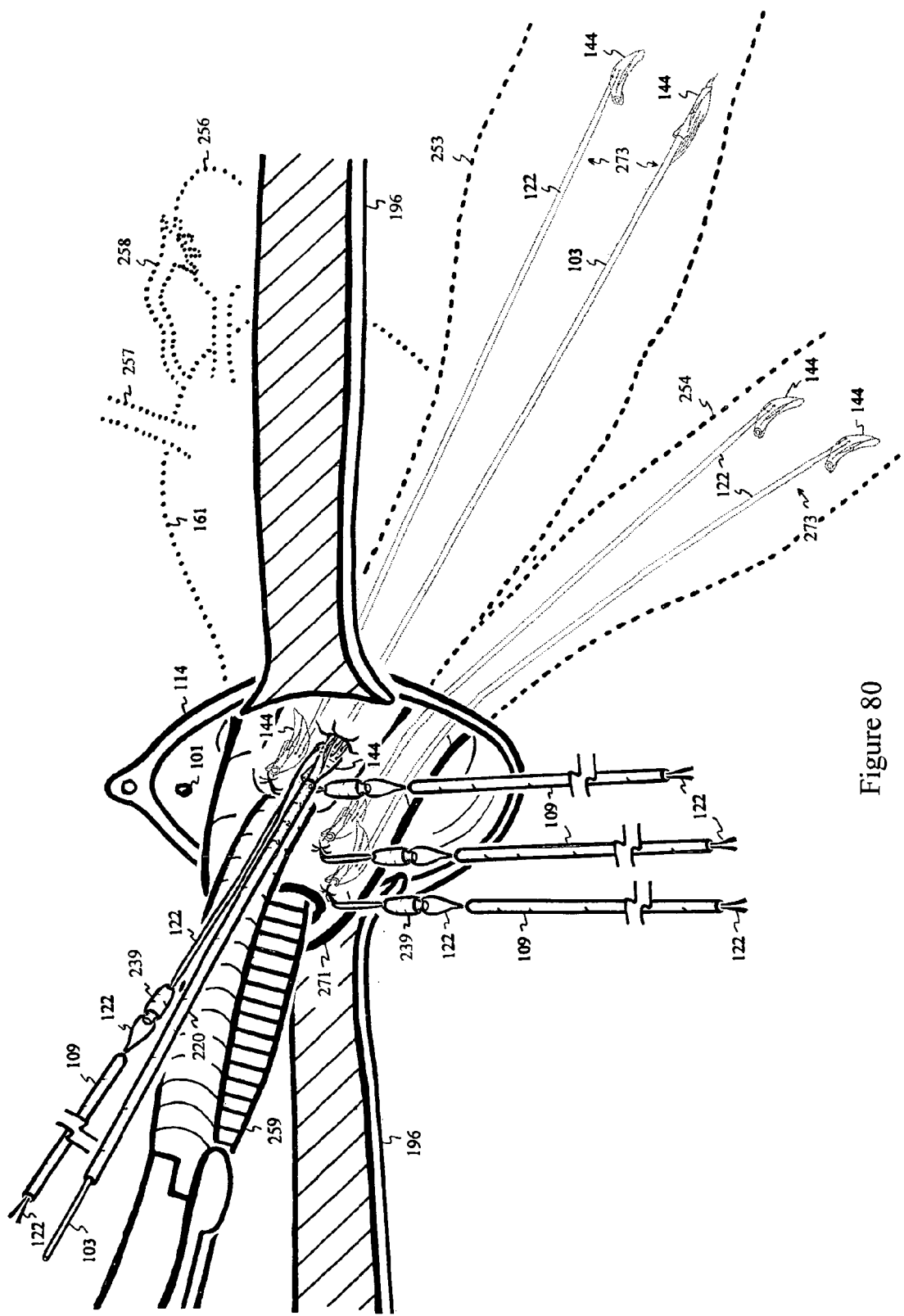
FIG. 80 shows insertions of multiple approximating devices 273 into cardinal 253 and sacrouterine 254 ligaments supporting the uterus 161.
Figure 81:
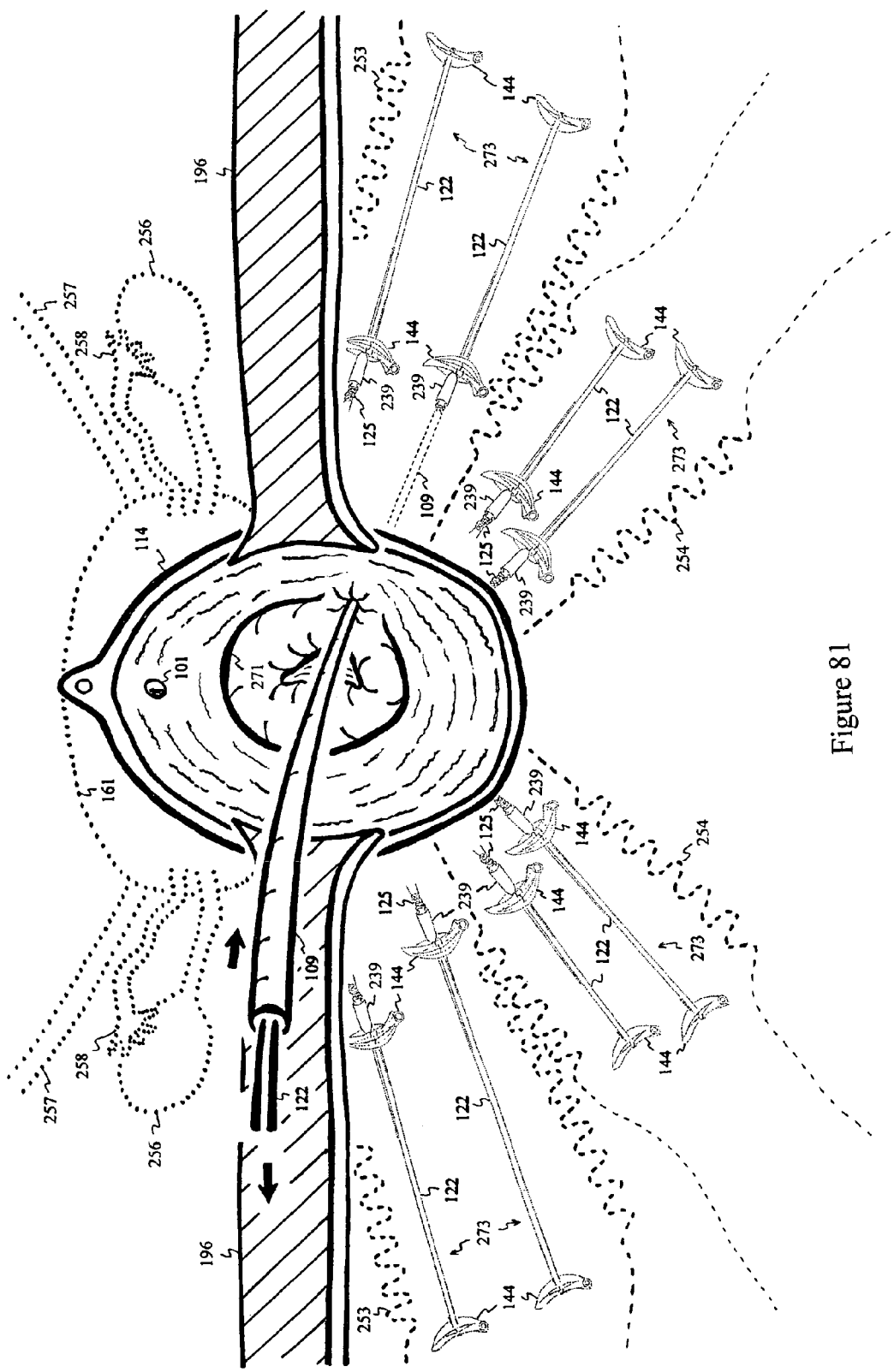
FIG. 81 indicates the ascendant cervix 271 as the result of sutures 122 tightening to plicate the cardinal 253 and sacrouterine 254 ligaments.

Similar to the hysterectomy procedure through the vagina 114 under general anesthesia, the muscles and ligaments are relaxed. The uterus 161 is pulled down from the vagina 114 by a grasping device 259 to expose the cardinal 253 and sacrouterine 254 ligaments, as shown in FIG. 80, with ovaries 256, fallopian tubes 258 and round ligaments 257 within the abdomen. Using various guiding and insertion techniques, the needle 103 is advanced along the ligament 253 or 254 to deliver the anchors 144, as shown in FIG. 80. The sutures 122 are loaded with suture locks 239 and plungers 109. The approximating devices 273 are then individually tightened by advancing the plungers 109 against the suture locks 239, while the sutures 122 are being pulled to plicate and shorten the ligament 253 and/or 254, as shown in FIG. 81. In essence, the ligament 253 and/or 254 is folded, crinkled or bunched together under the tension of the approximating devices 273. As a result, the cervix 271 and the entire uterus 161 are lifted by the shortened cardinal 253 and/or sacrouterine 254 ligaments.

The shortened ligament can be permanently maintained to uphold the uterus 161. As the ligament 253 and/or 254 are traumatized by insertions of needles 103 and anchors 144, oozing from the traumatized tissue can initiate tissue adhesion to hold and keep the ligament 253 and/or 254 in the plicated position even after degradation of the suture 122 and the anchors 144. The plicated ligament 253 and/or 254 also undergo tissue remodeling, including collagen crosslinking, which may also result in permanent shortening of the ligament 253 and/or 254.

Figure 85:
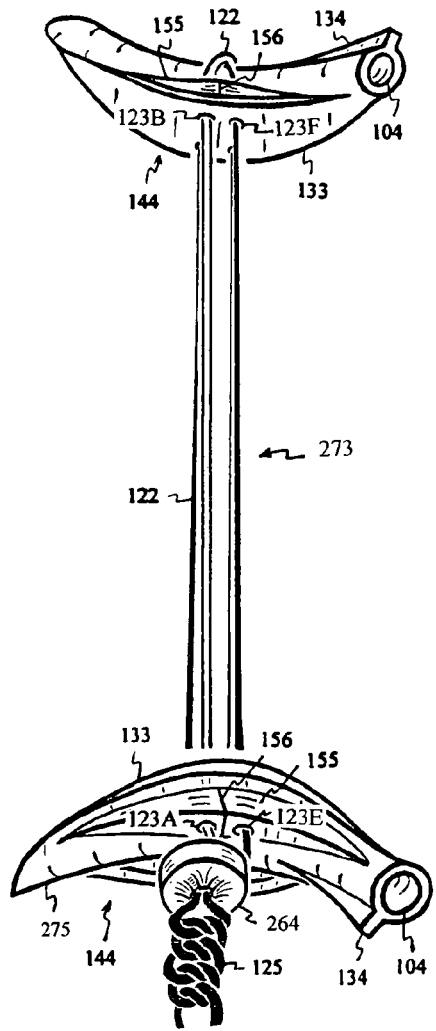
FIG. 85 depicts fastening of the approximating device 273 by tying knots 125 beneath the suture-gripping device 264.

A modified procedure and a suture-gripping device are designed for fastening an anchor 144 within thin tissue. FIG. 82 depicts partial insertion of the proximal anchor 144 of the approximating device 273 into a thin tissue 130. FIG. 83 shows a prior art suture-gripping device 264, with jutted flaps 265 biting and resisting upward slippage of the suture 122. The suture-gripping device 264 loaded on the suture 122 is followed by the plunger 109, as indicated in FIG. 84. The needle 103 and sleeve 220 are then withdrawn from tissue 130. Similar to the procedure depicted in FIG. 61, the sutures 122 are pulled, and the plunger 109 is pushed against the suture gripping device 264 to draw the proximal anchor 144 into the tissue 130 and tighten the approximating device 273. Then, knots 125 are tied beneath the gripping device 264 to secure the sutures 122, as shown in FIG. 85.

Figure 86:
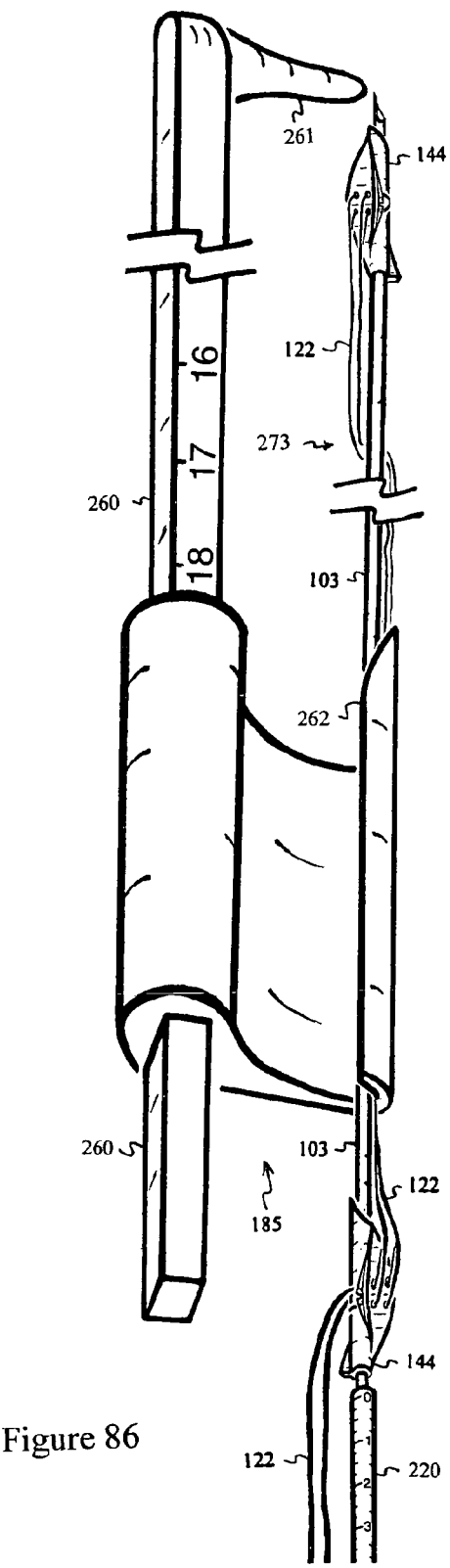
FIG. 86 shows a guide 185 to direct needle 103 insertion along a track 262, with an extendible arm 260 and a pointer 261 to indicate the destination of the needle 103.

Accuracy of needle 103 insertion of the approximating device 273 can be improved with a guide 185, as shown in FIG. 86. The guide 185 contains a track 262 for the needle 103 to slide along, an extendible arm 260 to align with the needle 103, and a pointer 261 to indicate the target site. In addition, measuring units on the arm 260 indicate depth of needle 103 penetration.

Figure 87:
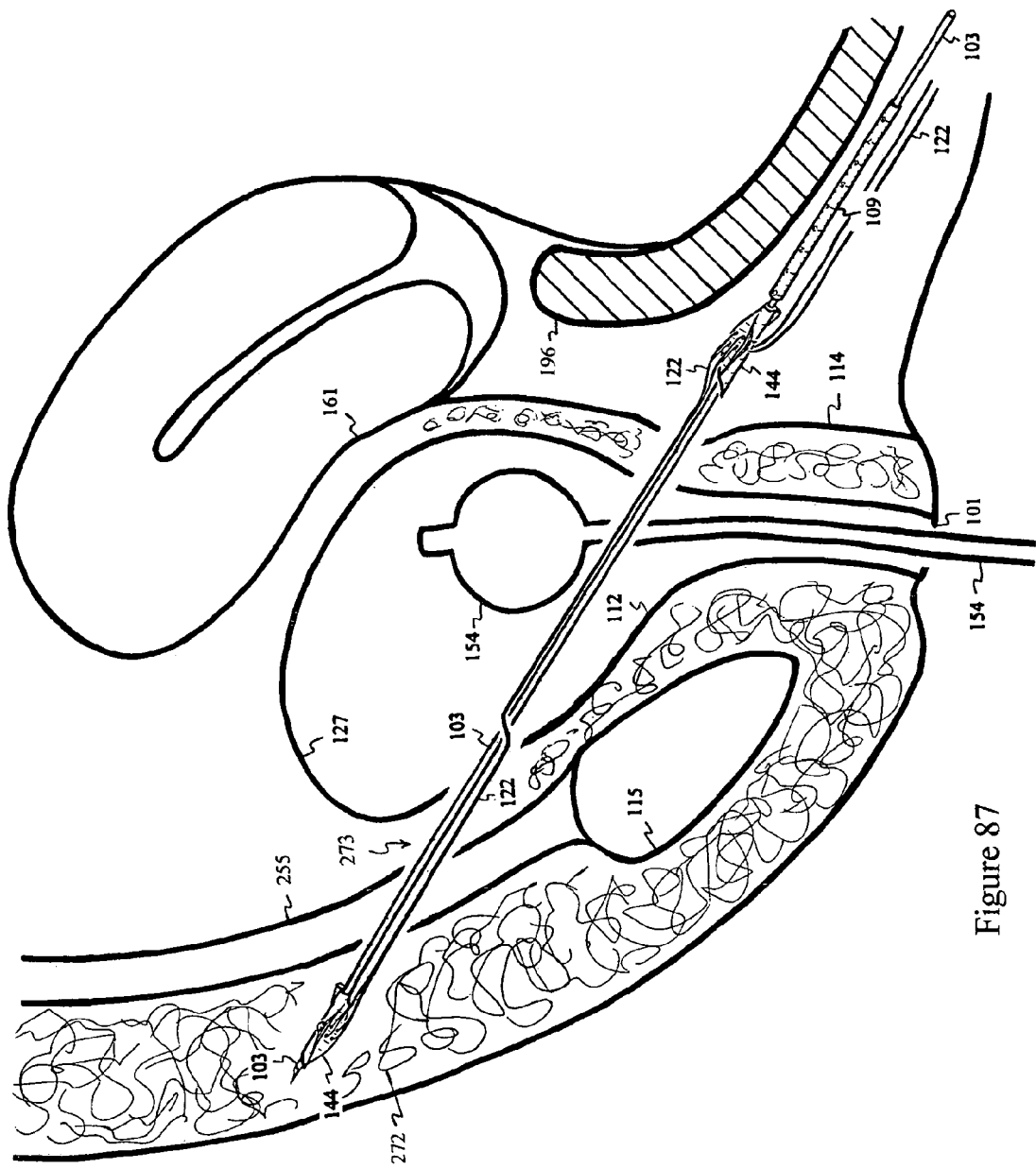
FIG. 87 depicts needle 103 insertion through the vaginal 114 wall, lateral to the urethra 101 into fascia 255 and adipose tissue 272.
Figure 88:
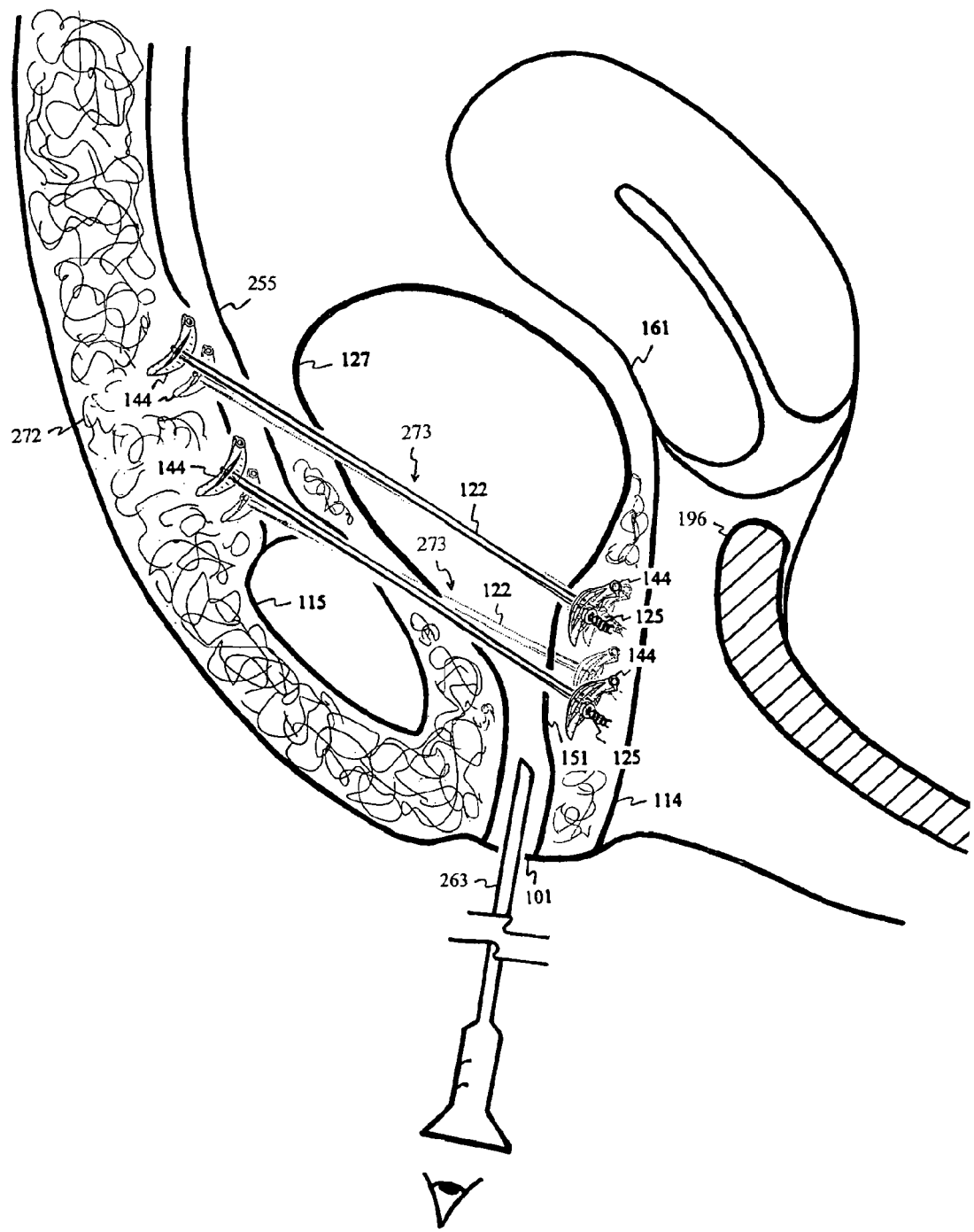
FIG. 88 indicates support of the posterior urethral wall 151 by the anchors 144 of the approximating devices 273.

As mentioned, the traditional surgical treatment for urinary incontinence is to provide backboard support to the urethral posterior wall 151 by pulling the vagina 114 forward with sutures 122. The sutures 122 are then fastened onto the fascia or ligament in the abdominal wall, as indicated in FIGS. 17 and 18. The approximating device 273 can provide similar backboard support to the posterior wall 151 without any incision 157. FIG. 87 depicts the vagina 114 is dilated with a retractor 196. The needle 103 is inserted through the anterior wall of the retracted vagina 114, lateral to the bladder neck 112, through the fascia 255 or ligament into adipose tissue 272 above the pubic symphysis 115. The distal anchor 144 is then deployed within the adipose tissue 272 and the proximal anchor 155 within the vaginal 114 wall with the suture-gripping device 264. The approximating device 273 is then tightened by pulling the suture 122 and pushing the plunger 109. The tightness of the plication can be seen through the urethra 101 with an endoscope 263. The suture 122 is then knotted 125 and cut, as shown in FIGS. 85 and 88. FIG. 88 shows a minimally invasive approach to supporting the posterior-urethral wall 151 of the urethra 101 by pulling the vaginal 114 wall forward with approximating devices 273. As mentioned, trauma from insertion of needles 103 and anchors 144 can lead to tissue adhesion, providing permanent posterior wall 151 support even after degradation of the suture 122, anchor 144 and gripping device 264.

Figure 89:
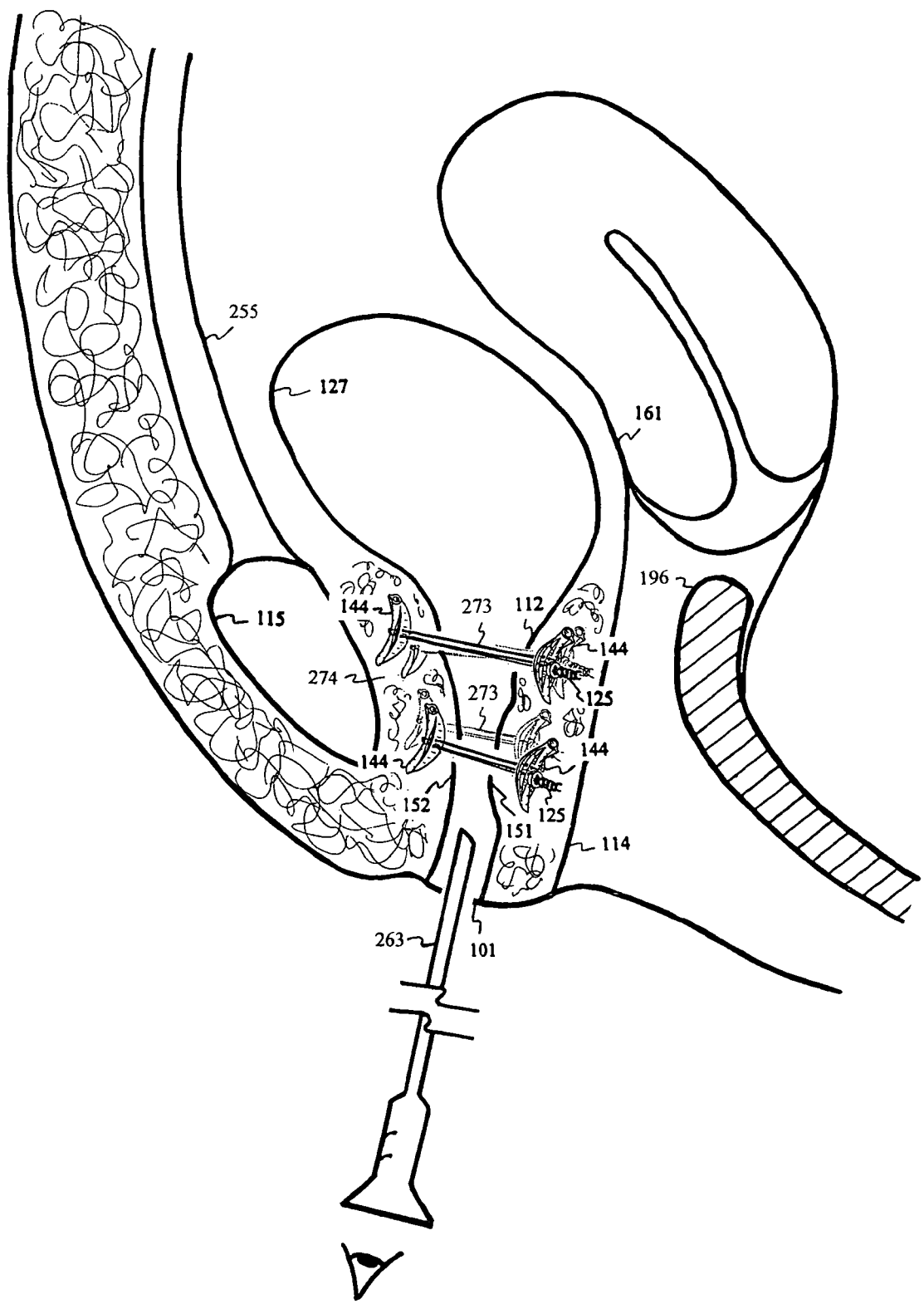
FIG. 89 also shows support of the posterior urethral wall 151 by tightening or restricting between fascia covering the anterior urethral wall 152 and the vaginal 114.

It may also be possible to tighten the bladder neck 112 and restrict the sphincteric region of the urethra 101 without involving the ligament or fascia 255 in the abdominal wall. The needle 103 can be inserted lateral to the bladder neck 112 or the urethra 101, into the retropubic space 274, area between the pubic symphysis 115 and bladder/urethra 127/101, to deliver the distal anchor 144. The proximal anchors 144 are deployed as mentioned within the vaginal 114 wall. As the approximating devices 273 are tightened, the bladder neck 112 as well as the urethra 101 are sandwiched between the anterior 152 fascia and the vagina 114, as shown in FIG. 89, to tighten the bladder neck 112 and treat sphincteric deficiency.

The most difficult step in installing the approximating device 273 is probably the guidance of the needle 103 safely and accurately into tissue. To maximize the benefit from the effort of needle 103 insertion, multiple pairs of approximating devices 273 can be loaded or passed along the needle 103, as shown in FIG. 90. With only a single needle 103 insertion, the approximating strength is greatly enhanced with multiple devices 273 installed, as shown in FIG. 91.

The dynamics of anchor 144 pivoting or rotation responding to suture 122 tension is especially significant within thin tissue 130. From observation within transparent gel wax, the initial movement of a crude prototype anchor 144 responding to suture 122 tension was in both pullout and lateral rotational directions. A similar result was obtained in meat. The suture 122 was not truly fastened until the prototype anchor 144 had rotated from the insertion position to fastening or perpendicular position. Before the fastened position was achieved, the suture 122 could be pulled with some resistance. The pivotal or rotational efficiency of the anchor 144 can probably be described by the pullout distance of the pulled suture 122. In an experiment using pork and the crude prototype anchor 144, the pullout distance was about one and half lengths of the prototype anchor 144 before the anchor 144 was secured. Within thin tissue, the anchor 144 would be pulled out before reaching the fastened position. With modifications to the crude prototype anchor 144, rotational efficiency can be significantly improved.

The needle 103 can also contain an inner and outer sleeves 220. The sleeves 220 are stacked over each other, and both sleeves 220 capable of sliding over the needle 103, as shown in FIG. 92. The lumen 104 of the distal anchor 144 fits over the distal portion of the needle 103, but too small to fit over the inner sleeve 220. The slightly larger lumen 104 of the proximal anchor 144 fits over the inner sleeve 220, but too small to fit over the outer sleeve 220. In essence, the inner sleeve 220 supports the distal anchor 144 and the outer sleeve 220 supports the proximal anchor 144, with both sleeves 220 and anchors 144 fit over the needle 103. Spearheading by the needle 103, the anchors 144 and sleeves 220 are punctured into tissue. Within a proper depth into the tissue, the inner sleeve 220 is held stationary while the needle 103 is partially withdrawn to disengage and deploy the distal anchor 144. Similarly, the outer sleeve 220 is held stationary while the needle 103 is fully withdrawn to deploy the proximal anchor 144.

The fin 134 can extend beyond the length of the body 275 and be made pointed to spearhead and expedite the rotation of the suture anchor 144, as shown in FIG. 93. The side view of the pointed and extended fin 134 is more evident in FIG. 94. The sharpened fin 134 helps lateral penetration into tissue 130. Extension of the fin 134 lengthens $L_1$ favors and expedites lateral rotation of the anchor 144. Even though $L_1$ is significantly lengthened, the suture holes 123 are still at or near the center of the platform 133 to prevent excessive rotation after reaching the fastened position.

Anchor 144 rotation begins with lateral tissue 130 penetration of the fin 134, followed by the proximal end of the body 275, then the platform 134 of the anchor 144. To ease tissue 130 penetration and expedite rotation, the proximal portion of the platform 133 is tapered and curved toward the fin 134, as shown in FIGS. 93 and 94. As the anchor 144 rotates, the curved platform 133 follows the fin 134 and smoothly lodges into the tissue 130. The tapered proximal end of the anchor 144 is supported by a shape-matching step 165 on the needle 103, as shown in FIG. 94. The shape-matching contact between the anchor 144 and the step 165 also helps to minimize spinning of the anchor 144 around the delivering needle 103.

Location of the elastic curvature of the anchor 144 can also affect the rotational efficiency. The curvature near the proximal end of the anchor 144 is more likely to have better rotational efficiency than the efficiency of the curvature situated near the distal end of the anchor 144.

A wide range of materials can be used to fabricate the suture anchor 144. Biocompatible polymers, such as polypropylene, polyethylene, poly-ether-ether-ketone, acetal resin, polysulfone and polycarbonate, are possible candidates. For biodegradable capability, the anchor 144 can be made with polylactate, polyglycolic, poly-lactide-co-glycolide, polycaprolactone, trimethylene carbonate or combinations of these materials. Many of these degradable polymers are in US FDA approved products. Other degradable polymers, such as polydioxanone, polyanhydride, trimethylene carbonate, poly-beta-hydroxybutyrate, polyhydroxyvalerate, poly-gama-ethyl-glutamate, poly-DTH-iminocarbonate, poly-bisphenol-A-iminocarbonate, poly-ortho-ester, polycyanoacrylate and polyphosphazene can also be used. Nickel-titanium alloy, spring-tempered stainless steel, titanium, stainless steel or other metallic material provides strength and durability.

The anchor 144 can also be coated with biocompatible polymers, such as polyurethane, polytetrafluoroethylene, silicon, ultra high molecular weight polyethylene or other material. For additional biological and surgical benefits, the anchor 144 can also be coated with lubricants, growth factors, nutrients, buffering agents, collagen, hydroxyapatite, analgesics, sealants, blood clotting agents, antibiotics, radiopaque or echogenic agents. All materials should be able to withstand sterilization by gamma, electron beam, autoclave, ETO, plasma or UV light to prevent infection.

The stepped needle 103 and sleeve 220 can be made with stainless steel, titanium, nickel titanium other metal or alloy. The stepped needle 103 and sleeve 220 can be coated with lubricant, blood clotting, radiopaque or echogenic agents. For hard-to-reach surgical sites, the stepped needle 103 can be made curved to gain accessibility for the surgeon. To accommodate the curvature of the stepped needle 103, the sleeve 220 can also be made with elastic material, such as nickel titanium, polypropylene, polyethylene or other flexible material. The stepped needle 103 and sleeve 220 can also be coated with lubricant, antibiotic, radiopaque or echogenic agents.

The suture 122 can be permanent or biodegradable, braided or monofilament. The suture 122 can also be metallic for strength and durability.

In summary, the anchor 144 is designed for partial thickness or full thickness suture 122 anchoring and is delivered with the stepped needle 103. Deployment of the anchor 144 can be as simple as inserting and withdrawing the stepped needle 103 in and from tissue. The sleeve 220 sliding over the stepped or a smooth needle 103 can be helpful in deploying the anchor 144 and manipulating tissue. The curvature of the anchor 144 promotes initial anchor 144 rotation within tissue when tension is applied to the suture 122. The fin 134 is designed to (1) dislodge the anchor 144, (2) enhance initial rotation of the anchor 144, and (3) stabilize the anchor 144 during rotation. The platform 133, especially fortified with bend stops 155, is designed to increase the anchoring strength within tissue. When multiple anchors 144 are delivered in series into tissue, as the suture 122 is pulled, the anchors 144 draw close to each other to plicate or approximate the pierced tissue.

It is to be understood that the present invention is by no means limited to the particular constructions disclosed herein and/or shown in the drawings, but also includes any other modification, changes or equivalents within the scope of the claims. Many features have been listed with particular configurations, curvatures, options, and embodiments. Any one or more of the features described may be added to or combined with any of the other embodiments or other standard devices to create alternate combinations and embodiments.

It should be clear to one skilled in the art that the current embodiments, materials, constructions, methods, tissues or incision sites are not the only uses for which the invention may be used. It has been foreseen that the anchor 144 and the stepped needle 103 can be applied in other surgical and non-surgical purposes. Different materials, constructions, methods or designs for the anchor 144, stepped needle 103 or the sleeve 220 can be substituted and used. Nothing in the preceding description should be taken to limit the scope of the present invention. The full scope of the invention is to be determined by the appended claims.

What is claimed is:

1. A suture anchor delivery device comprising:
   a penetrating member; and
   a suture anchor having a delivery configuration in a first shape and a deployment configuration in a second shape, the suture anchor comprising:
      a suture anchor body;
      a passage extending at least partially through the suture anchor body, the passage sized and configured to receive the penetrating member;
      at least one suture opening sized and configured to receive a suture, the at least one suture opening separate from the passage; and
      a guiding platform;
   wherein the suture anchor is carried on the penetrating member and wherein removing the penetrating member from the suture anchor body changes the shape of the suture anchor from the delivery configuration first shape to the deployment configuration second shape.

2. The suture anchor delivery device of claim 1, wherein the guiding platform is a generally flat surface.

3. The suture anchor delivery device of claim 1, wherein the guiding platform includes the at least one suture opening.

4. The suture anchor delivery device of claim 1, wherein the at least one suture opening is at a middle portion of the suture anchor.

5. The suture anchor delivery device of claim 1, wherein the guiding platform extends along at least a majority of a length of the suture anchor body.

6. The suture anchor delivery device of claim 1, wherein the guiding platform runs generally parallel to the passage of the suture anchor body.

7. The suture anchor delivery device of claim 1, wherein the guiding platform runs generally parallel to said passage of the suture anchor body when the suture anchor is in the delivery configuration.

8. The suture anchor delivery device of claim 1, wherein the guiding platform extends beyond the length of the suture anchor body.

9. The suture anchor delivery device of claim 1, wherein the guiding platform includes a penetrating portion.

10. The suture anchor delivery device of claim 1, wherein the guiding platform is configured to induce rotation of the suture anchor when the suture anchor is deployed in tissue.

11. An anchor delivery device comprising:
    an anchor having a delivery configuration in a first shape and a deployment configuration in a second shape, the anchor comprising a guiding fin and an anchor tube having a lumen;
    a penetrating member initially positioned within the anchor tube lumen for releasably carrying the anchor, wherein the penetrating member carries the anchor in the delivery configuration and in the first shape and releases the anchor to the deployment configuration and to the second shape; and
    a suture connected with the anchor.

12. The anchor delivery device of claim 11 wherein the guiding fin is configured to induce rotation of the anchor when the anchor is deployed in tissue.

13. The anchor delivery device of claim 11, wherein the guiding fin includes a penetrating portion.

14. The anchor delivery device of claim 11, wherein the suture passes through an opening on the guiding fin.

15. The anchor delivery device of claim 14, wherein the opening is at a middle portion of the guiding fin.

16. The anchor delivery device of claim 11, wherein the guiding fin extends along at least a majority of a length of the anchor tube.

17. A method of delivering a suture anchor, the suture anchor comprising a suture anchor body sized and configured to be carried externally to penetrating member, at least one suture opening sized and configured to receive a suture, and a guiding platform, comprising:
    advancing a penetrating member to a position past a tissue plane, wherein the penetrating member carries the suture anchor in a delivery configuration in a first shape;
    withdrawing the penetrating member from the position past the tissue plane, wherein withdrawing the penetrating member releases the suture anchor to a deployment configuration in a second shape; and
    applying tension to a suture connected to the suture anchor, wherein the suture anchor rotates.

18. The method of claim 17, wherein applying tension causes the suture to rotate by drawing the guiding platform against the tissue plane.

19. The method of claim 17, wherein applying tension engages an edge of the guiding platform with the tissue plane.

20. The method of claim 17, wherein the penetrating member carries the suture anchor from within a lumen of the suture anchor body.

* * * * *